United States Patent
Nukada et al.

(10) Patent No.: US 9,034,544 B2
(45) Date of Patent: May 19, 2015

(54) COMPOUND, CHARGE TRANSPORTING FILM, PHOTOELECTRIC CONVERSION DEVICE, AND ELECTROPHOTOGRAPHIC PHOTORECEPTOR USING THE COMPOUND, METHOD OF PRODUCING ELECTROPHOTOGRAPHIC PHOTORECEPTOR, PROCESS CARTRIDGE, AND IMAGE FORMING APPARATUS

(75) Inventors: Katsumi Nukada, Kanagawa (JP); Wataru Yamada, Kanagawa (JP); Tomoya Sasaki, Kanagawa (JP); Yuko Iwadate, Kanagawa (JP); Kenji Kajiwara, Kanagawa (JP)

(73) Assignee: FUJI XEROX CO., LTD., Tokyo (JP)

( * ) Notice: Subject to any disclaimer, the term of this patent is extended or adjusted under 35 U.S.C. 154(b) by 30 days.

(21) Appl. No.: 13/412,179

(22) Filed: Mar. 5, 2012

(65) Prior Publication Data
US 2013/0052572 A1 Feb. 28, 2013

(30) Foreign Application Priority Data

Aug. 22, 2011 (JP) .................. 2011-181010

(51) Int. Cl.
| | |
|---|---|
| G03G 5/047 | (2006.01) |
| C07C 217/76 | (2006.01) |
| C07C 251/86 | (2006.01) |
| G03G 15/00 | (2006.01) |
| G03G 5/05 | (2006.01) |

(Continued)

(52) U.S. Cl.
CPC ............ *C07C 217/76* (2013.01); *C07C 251/86* (2013.01); C07C 2101/14 (2013.01); C07C 2103/18 (2013.01); *G03G 15/75* (2013.01);

*G03G 5/0592* (2013.01); *G03G 5/0614* (2013.01); *G03G 5/14769* (2013.01); *G03G 5/14791* (2013.01)

(58) Field of Classification Search
USPC ......................... 430/58.7, 58.75, 66; 399/159
See application file for complete search history.

(56) References Cited

U.S. PATENT DOCUMENTS

| | | | |
|---|---|---|---|
| 5,411,827 | A | 5/1995 | Tamura et al. |
| 5,427,880 | A | 6/1995 | Tamura et al. |

(Continued)

FOREIGN PATENT DOCUMENTS

| | | |
|---|---|---|
| JP | A-62-251757 | 11/1987 |
| JP | A-05-040360 | 2/1993 |

(Continued)

OTHER PUBLICATIONS

Translation of JP 2000-147814 published May 2000.*

*Primary Examiner* — Peter Vajda
(74) *Attorney, Agent, or Firm* — Oliff PLC

(57) ABSTRACT

Provided is a compound represented by the following Formula (I):

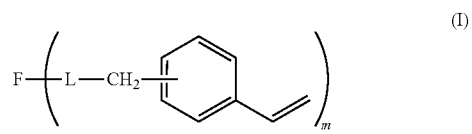

wherein in Formula (I), F represents a charge transporting skeleton, L represents a divalent linking group including a —$(CH_2)_n$—O— group, m represents an integer of from 1 to 8, and n represents an integer of from 3 to 6.

21 Claims, 19 Drawing Sheets

(51) Int. Cl.
*G03G 5/06* (2006.01)
*G03G 5/147* (2006.01)

(56) References Cited

U.S. PATENT DOCUMENTS

| | | | |
|---|---|---|---|
| 5,496,671 | A | 3/1996 | Tamura et al. |
| 2004/0043312 | A1 | 3/2004 | Kikuchi et al. |
| 2004/0248024 | A1 | 12/2004 | Suzuki et al. |
| 2004/0253527 | A1 | 12/2004 | Suzuki et al. |
| 2007/0122724 | A1 | 5/2007 | Suzuki et al. |
| 2007/0178400 | A1* | 8/2007 | Kikuchi et al. ............... 430/133 |
| 2008/0020305 | A1 | 1/2008 | Suzuki et al. |
| 2009/0297217 | A1* | 12/2009 | Iwanaga et al. ............... 399/111 |
| 2011/0294065 | A1* | 12/2011 | Hobo et al. ................... 430/115 |

FOREIGN PATENT DOCUMENTS

| | | | |
|---|---|---|---|
| JP | A-05-216249 | 8/1993 | |
| JP | A-05-323630 | 12/1993 | |
| JP | A-07-072640 | 3/1995 | |
| JP | A-07-146564 | 6/1995 | |
| JP | B2-2852464 | 11/1998 | |
| JP | A-11-052603 | 2/1999 | |
| JP | A-2000-019749 | 1/2000 | |
| JP | 2000-147814 * | 5/2000 | ............... G03G 5/06 |
| JP | A-2000-206715 | 7/2000 | |
| JP | A-2000-206717 | 7/2000 | |
| JP | A-2001-166509 | 6/2001 | |
| JP | A-2001-166510 | 6/2001 | |
| JP | A-2001-175016 | 6/2001 | |
| JP | A-2002-082469 | 3/2002 | |
| JP | B2-3287678 | 3/2002 | |
| JP | A-2004-012986 | 1/2004 | |
| JP | A-2004-302450 | 10/2004 | |
| JP | A-2006-084711 | 3/2006 | |
| JP | A-2007-086522 | 4/2007 | |

* cited by examiner

COMPOUND, CHARGE TRANSPORTING FILM, PHOTOELECTRIC CONVERSION DEVICE, AND ELECTROPHOTOGRAPHIC PHOTORECEPTOR USING THE COMPOUND, METHOD OF PRODUCING ELECTROPHOTOGRAPHIC PHOTORECEPTOR, PROCESS CARTRIDGE, AND IMAGE FORMING APPARATUS

CROSS-REFERENCE TO RELATED APPLICATIONS

This application is based on and claims priority under 35 USC 119 from Japanese Patent Application No. 2011-181010 filed Aug. 22, 2011.

BACKGROUND

1. Technical Field

The present invention relates to a reactive novel compound, a charge transporting film, a photoelectric conversion device, and an electrophotographic photoreceptor using the compound, a method of producing an electrophotographic photoreceptor, a process cartridge, and an image forming apparatus.

2. Related Art

An electrophotographic image forming apparatus has the following configuration and process in general.

That is, the surface of an electrophotographic photoreceptor is charged with a predetermined polarity and potential by a charger, an electrostatic latent image is formed by selectively erasing the surface of the charged electrophotographic photoreceptor by image exposure, the latent image is then developed as a toner image by attaching a toner to the electrostatic latent image by using a developing unit, and then an image which is formed by transferring the toner image to a transfer medium by using a transfer unit is discharged.

As the electrophotographic photoreceptor, electrophotographic photoreceptors (inorganic photoreceptors) using inorganic photoconductive materials such as selenium, a selenium-tellurium alloy, a selenium-arsenic alloy, and cadmium sulfide have been known in the related art. However, in recent years, organic photoreceptors using organic photoconductive materials that have great advantages in terms of low costs, manufacturability, and disposal property have been predominantly used, and there is a suggestion about improving strength of the electrophotographic photoreceptor by providing a protective layer on the surface of the electrophotographic photoreceptor.

SUMMARY

According to an aspect of the invention, there is provided a compound represented by the following Formula (I):

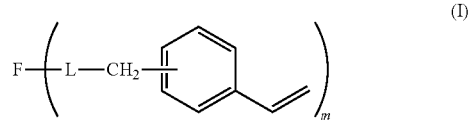

wherein in Formula (I), F represents a charge transporting skeleton, L represents a divalent linking group including a —(CH$_2$)$_n$—O— group, m represents an integer of from 1 to 8, and n represents an integer of from 3 to 6.

BRIEF DESCRIPTION OF THE DRAWINGS

Exemplary embodiments of the present invention will be described in detail based on the following figures, wherein.

DETAILED DESCRIPTION

Figure 1:
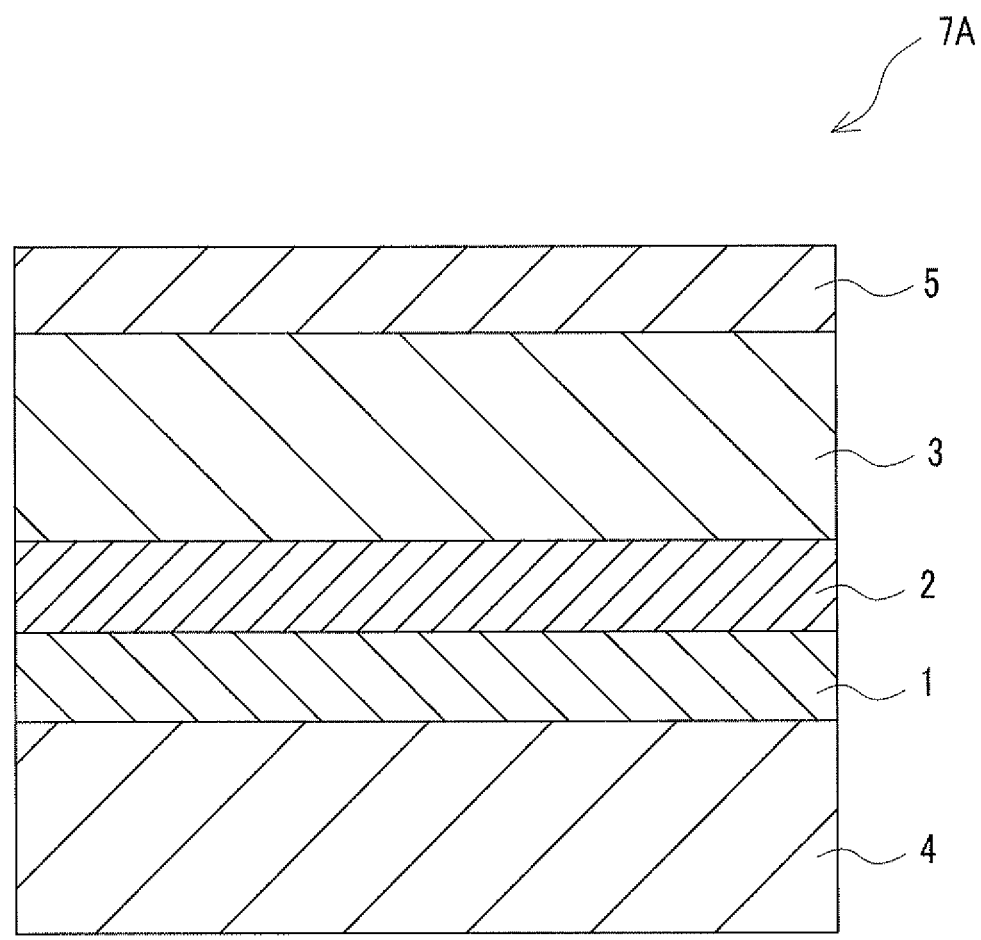
FIG. 1 is a schematic partial cross-sectional view showing an electrophotographic photoreceptor according to an exemplary embodiment.

Hereinafter, the exemplary embodiment of the invention will be described with appropriate reference to the attached drawings.

[Reactive Compound]

The novel compound according to the exemplary embodiment is a compound represented by the following Formula (I).

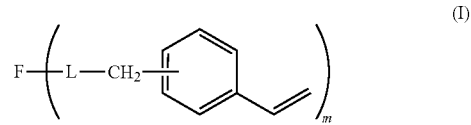

In Formula (I), F represents a charge transporting skeleton having an aromatic ring, L represents a divalent linking group that includes a —(CH$_2$)$_n$—O— group directly linked to the aromatic ring of F, m represents an integer of from 1 to 8, and n represents an integer of from 3 to 6. The compound is not limited as long as it satisfies this structural condition, but particularly, a compound in which m is 3 or greater is excellent in strength and electrical characteristics.

Hereinafter, the compound represented by Formula (I) or Formula (II) described later will be appropriately referred to as a specific charge transport material (a) for description.

If the compound having the structure represented by Formula (I) is used, a film having excellent electrical characteristics and high strength is obtained. Though not necessarily clear, the reason is considered to be as below.

That is, if the bulky charge transporting skeleton and a polymerization moiety (styryl group) are structurally close to each other, that is, are rigid, it is difficult for the polymerization moieties to move, and residual strain resulting from a curing reaction easily remains. Accordingly, the level of a HOMO (Highest Occupied Molecular Orbital) responsible for carrier transport is changed due to the strain of the charge transporting skeleton, and consequently, energy distribution easily broadens (energy disorder: σ is great). On the other hand, if established via a methylene group and an ether group, the molecular structure obtains flexibility, and a structure with small σ is easily obtained. Moreover, the dipole moment of a methylene group and an ether group is smaller than that of an ester group, an amide group, and the like, which also helps the reduction of σ, and accordingly, it is considered that the electrical characteristics become excellent. In addition, the addition of flexibility to the molecular structure causes reaction sites to more freely move, and the reaction rate also increases. Accordingly, it is assumed that a film having high strength is obtained.

For these reasons, a structure is desirable in which a linking chain rich in flexibility is mediated between the charge transporting skeleton and the polymerization moiety.

In the specific charge transport material (a) of such a desirable embodiment, the molecular weight of the molecule itself is increased by the curing reaction, the center of gravity does not easily move, and the degree of freedom of a styryl group is high. Accordingly, for example, as the uppermost surface layer of an electrophotographic photoreceptor, an uppermost surface layer obtained using the specific charge transport material (a) becomes excellent in electrical characteristics and has very high strength.

In the exemplary embodiment, the specific charge transport material (a) is desirably a compound represented by the following Formula (II) since the compound is excellent in a charge transport property.

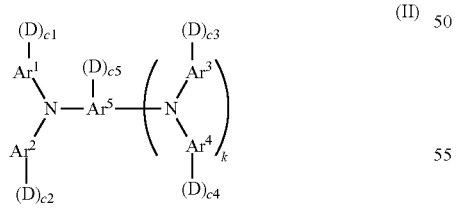

(II)

In Formula (II), each of $Ar^1$ to $Ar^4$ independently represents a substituted or unsubstituted aryl group, $Ar^5$ represents a substituted or unsubstituted aryl group or a substituted or unsubstituted arylene group, each of c1 to c5 independently represents an integer of from 0 to 2, and the sum of c1 to c5 is an integer of from 1 to 8. k represents 0 or 1. D is a group represented by the following Formula (III). In Formula (III), L represents a divalent linking group that includes a —$(CH_2)_n$—O— group directly linked to the aryl group of $Ar^1$ to $Ar^4$ and the aryl group or arylene group of $Ar^5$, and n represents an integer of from 3 to 6. The sum of c1 to c5 is desirably an integer of from 3 to 8.

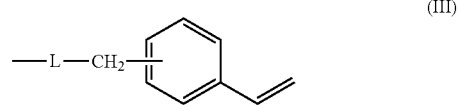

(III)

$Ar^1$ to $Ar^4$ are desirably any one of the following Formulae (1) to (7). The following Formulae (1) to (7) show "-(D)$_C$" that collectively represents "-(D)$_{C1}$" to "-(D)$_{C4}$" which may be linked to each of $Ar^1$ to $Ar^4$.

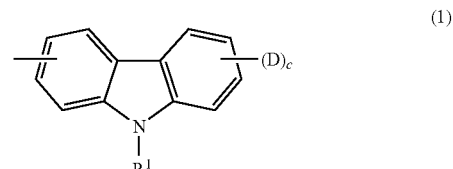

(1)

(2)

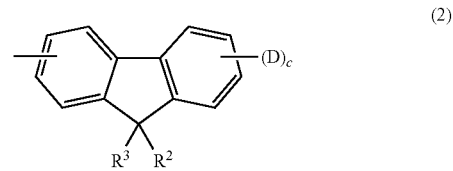

(3)

(4)

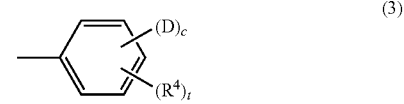

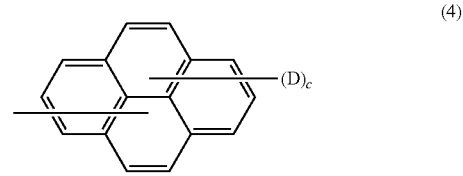

(5)

(6)

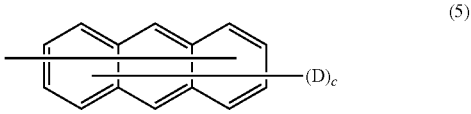

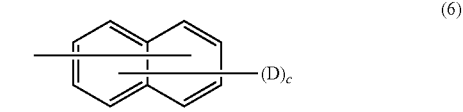

(7)

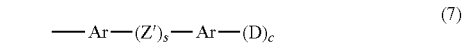

In the Formulae (1) to (7), represents one kind selected from a group consisting of a hydrogen atom, an alkyl group having from 1 to 4 carbon atoms, a phenyl group that is substituted with an alkyl group having from 1 to 4 carbon atoms or with an alkoxy group having from 1 to 4 carbon atoms, an unsubstituted phenyl group, and an aralkyl group having from 7 to 10 carbon atoms; each of $R^2$ to $R^4$ independently represents one kind selected from a group consisting of a hydrogen atom, an alkyl group having from 1 to 4 carbon atoms, an alkoxy group having from 1 to 4 carbon atoms, a phenyl group that is substituted with an alkoxy group having from 1 to 4 carbon atoms, an unsubstituted phenyl group, an aralkyl group having from 7 to 10 carbon atoms, and a halogen atom; Ar represents a substituted or unsubstituted arylene group; and D represents a group represented by the following Formula (III). In Formula (III), L represents a divalent linking group that includes a —(CH$_2$)$_n$—O— group directly linked to the aryl group of Ar$^1$ to Ar$^4$ and the aryl group or arylene group of Ar$^5$, and n represents an integer of from 3 to 6.

In Formula (3), t represents an integer of from 1 to 3.

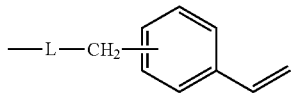
(III)

Herein, Ar in Formula (7) is desirably represented by the following Structural Formula (8) or (9).

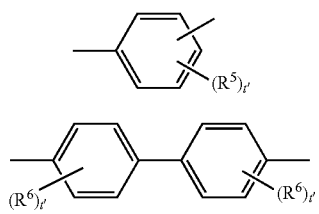
(8)

(9)

In the Formulae (8) and (9), each of R$^5$ and R$^6$ independently represents one kind selected from a group consisting of a hydrogen atom, an alkyl group having from 1 to 4 carbon atoms, an alkoxy group having from 1 to 4 carbon atoms, a phenyl group that is substituted with an alkoxy group having from 1 to 4 carbon atoms, an unsubstituted phenyl group, an aralkyl group having from 7 to 10 carbon atoms, and a halogen atom; and each t' represents an integer of from 0 to 3.

In Formula (7), Z' represents a divalent organic linking group, but Z' is desirably represented by any one of the following Formulae (10) to (17). Each s represents 0 or 1.

—(CH$_2$)$_q$— (10)

—(CH$_2$CH$_2$O)$_r$— (11)

(12)

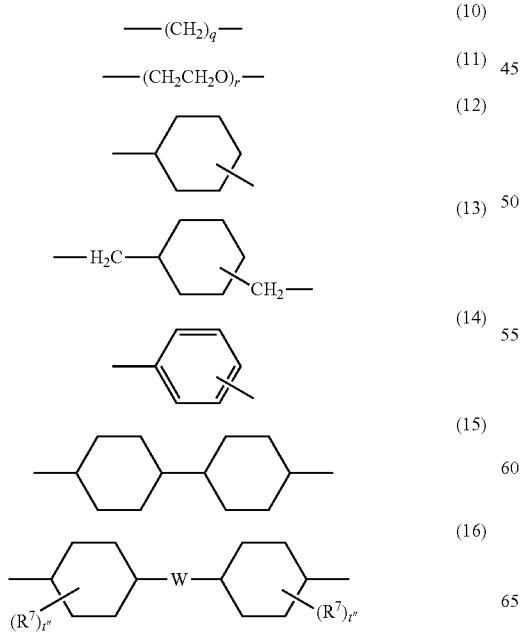
(13)

(14)

(15)

(16)

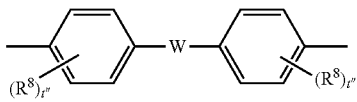
(17)

In the Formulae (10) to (17), each of R$^7$ and R$^8$ independently represents one kind selected from a group consisting of a hydrogen atom, an alkyl group having from 1 to 4 carbon atoms, an alkoxy group having from 1 to 4 carbon atoms, a phenyl group that is substituted with an alkoxy group having from 1 to 4 carbon atoms, an unsubstituted phenyl group, an aralkyl group having from 7 to 10 carbon atoms, and a halogen atom; W represents a divalent group; each of q and r independently represents an integer of from 1 to 10; and each t" represents an integer of from 0 to 3.

W in the Formulae (16) and (17) is desirably any one of divalent groups represented by the following (18) to (26). Here, in Formula (25), u represents an integer of from 0 to 3.

—CH$_2$— (18)

—C(CH$_3$)$_2$— (19)

—O— (20)

—S— (21)

—C(CF$_3$)$_2$— (22)

—Si(CH$_3$)$_2$— (23)

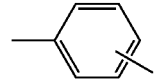
(24)

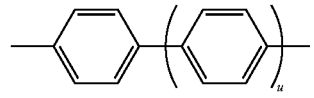
(25)

(26)

In Formula (II), when k is 0, Ar$^5$ is a substituted or unsubstituted aryl group, and examples of the aryl group include the same aryl group as exemplified in the description for Ar$^1$ to Ar$^4$. Moreover, when k is 1, Ar$^5$ is a substituted or unsubstituted arylene group, and examples of the arylene group include an arylene group obtained by removing one hydrogen atom at a predetermined position from the aryl group exemplified in the description for Ar$^1$ to Ar$^4$.

Hereinafter, specific examples of a charge transporting skeleton F, specific examples of the structure represented by Formula (III), and specific examples of the compound represented by Formula (I) will be shown. The following examples mean that a * portion of the example structure of Formula (III) is linked to a * portion described in the charge transporting skeleton exemplified below. For example, when a structure of the charge transporting skeleton: (1)-1 and a Formula (III) structure: (III)-1 are shown as a compound (I)-1, the following structure is shown.

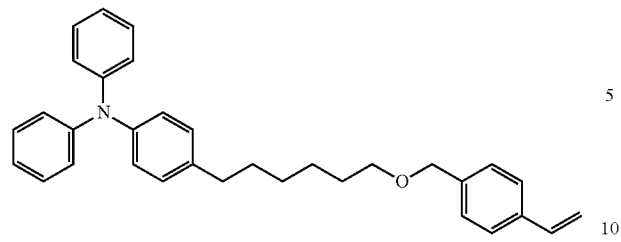
The compound represented by Formula (I) is not limited to the following examples.
Hereinafter, specific examples of the charge transporting skeleton F will be shown. As monofunctional skeletons, the following ones are exemplified.
(1)-1
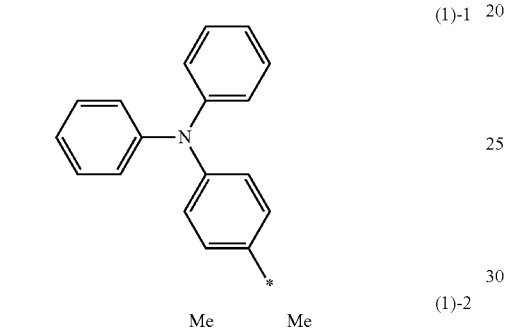
(1)-2
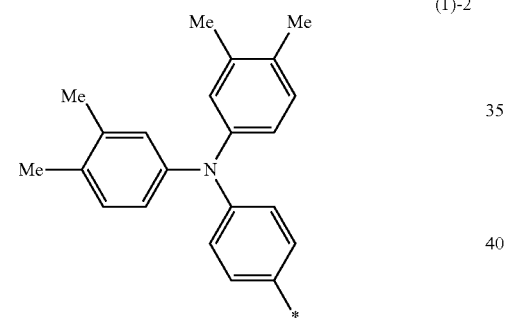
(1)-3
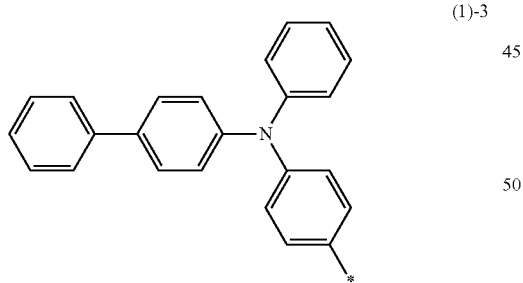
(1)-4
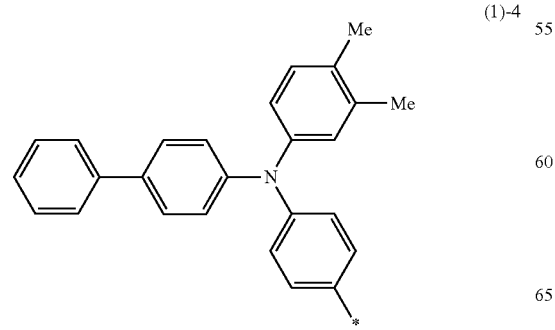
(1)-5
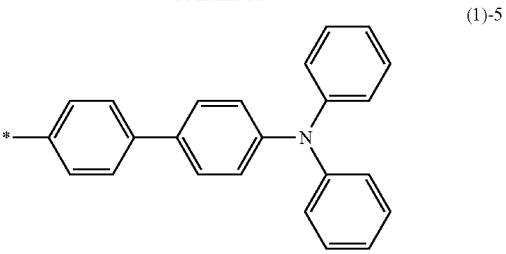
(1)-6
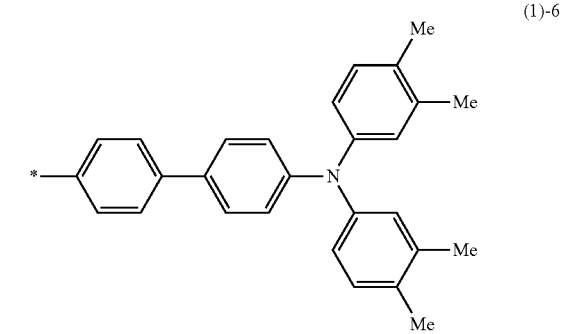
(1)-7
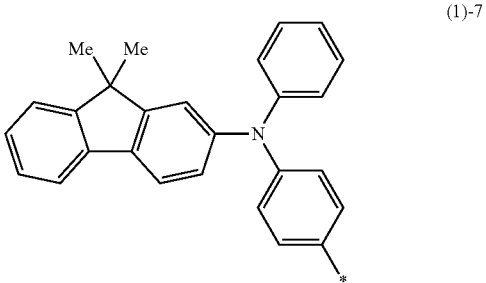
(1)-8
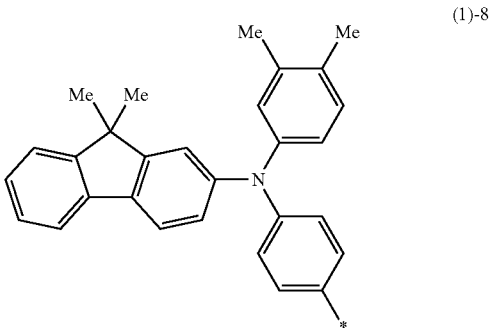
(1)-9
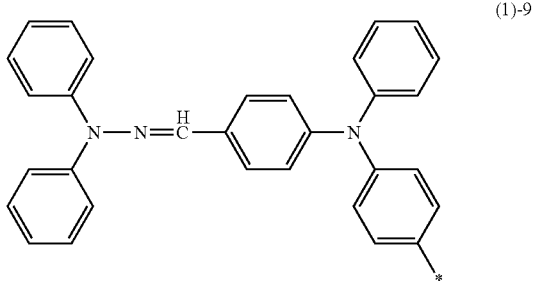

(1)-10
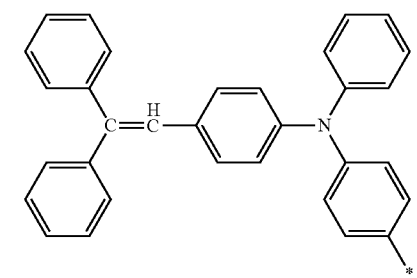
(1)-11
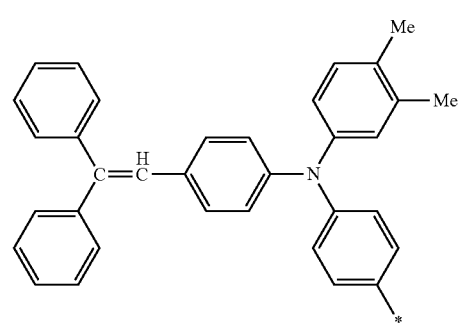
(1)-12
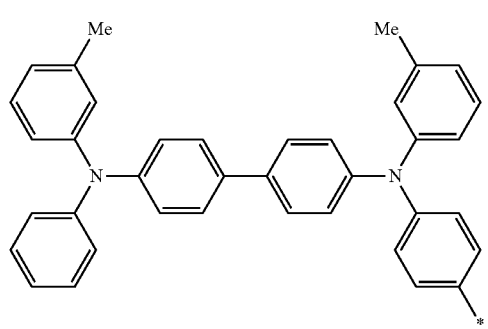
(1)-13
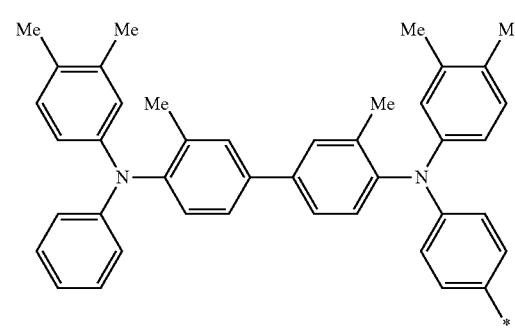
(1)-14
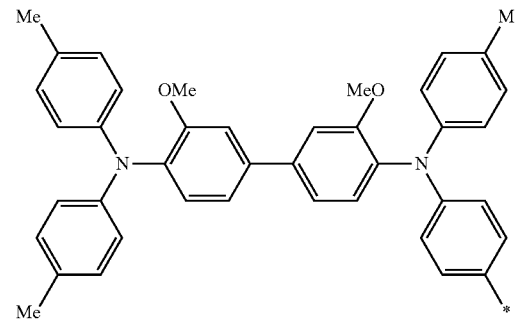
(1)-15
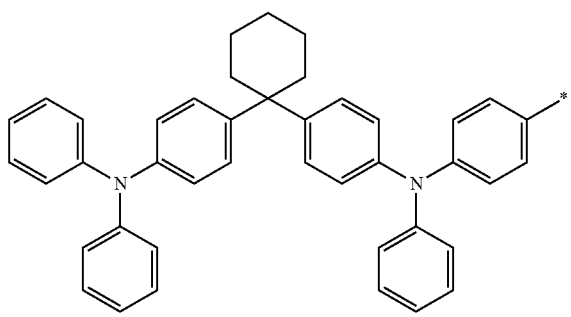
(1)-16
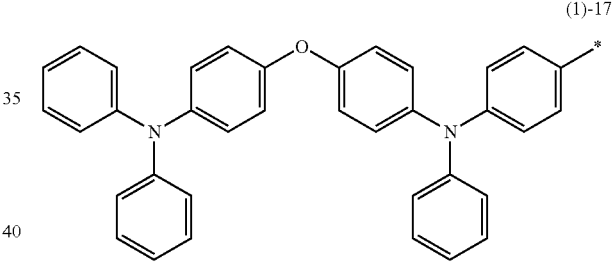
(1)-17
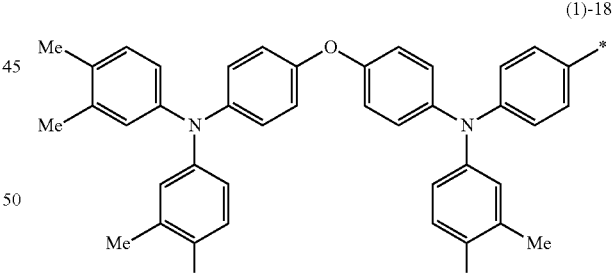
(1)-18
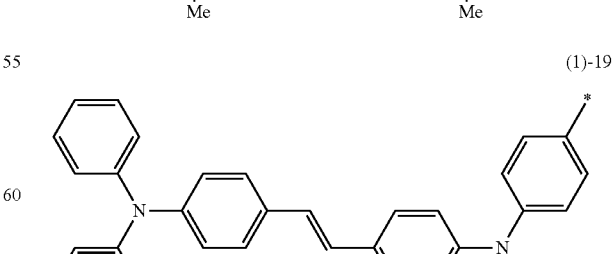
(1)-19

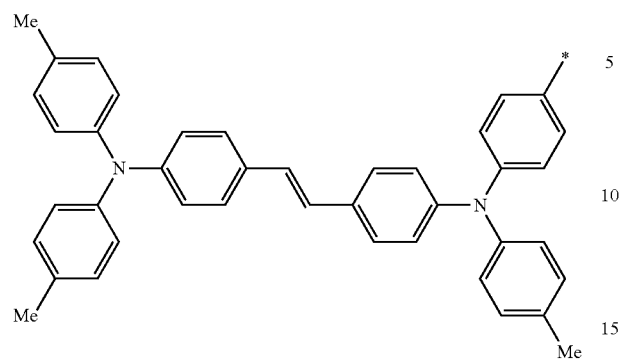
(1)-20
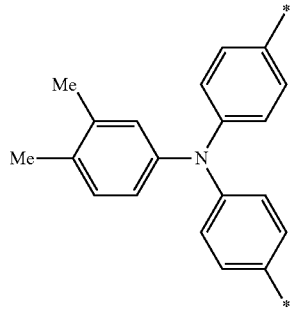
(2)-2
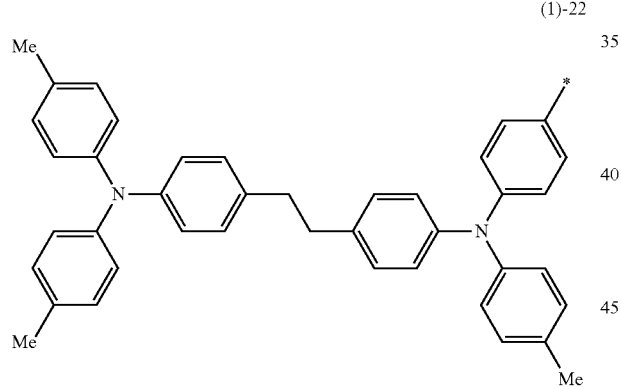
(1)-21
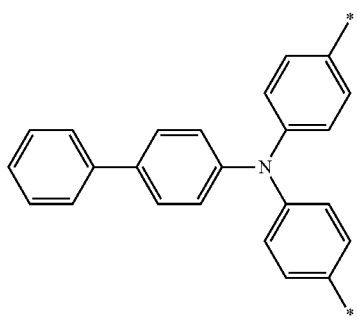
(2)-3
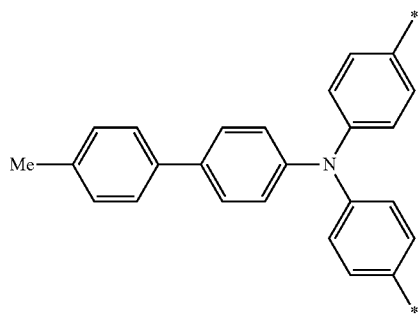
(2)-4
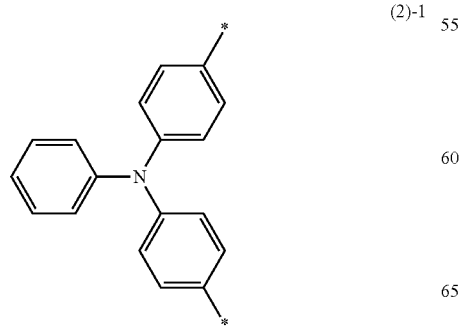
(1)-22
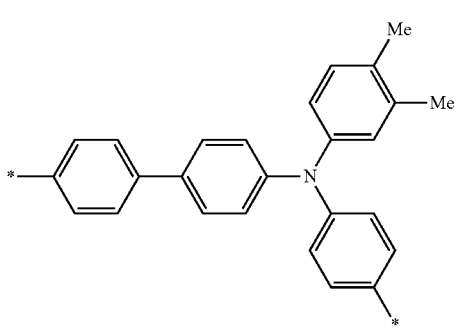
(2)-5
As bifunctional skeletons, the following ones are exemplified.
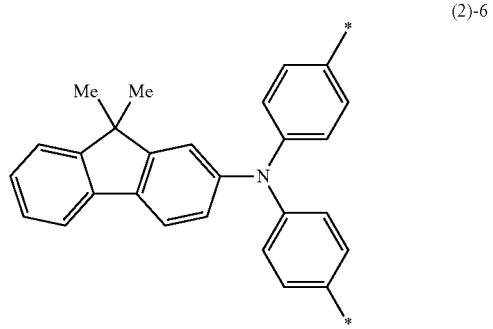
(2)-6
(2)-1

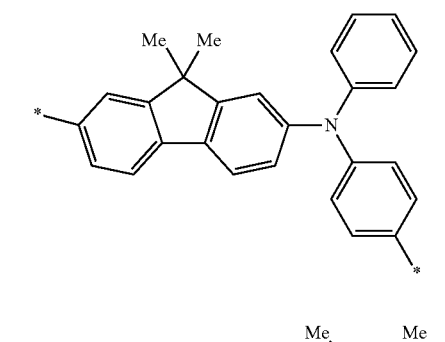
(2)-7
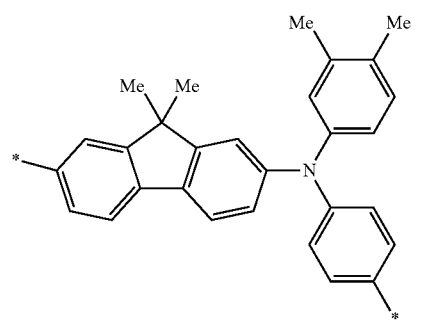
(2)-8
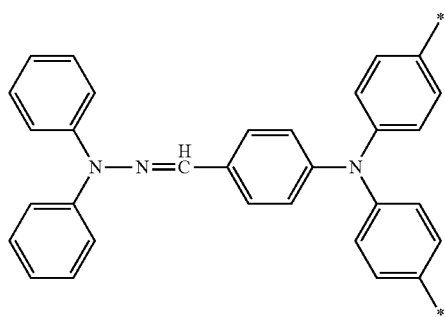
(2)-9
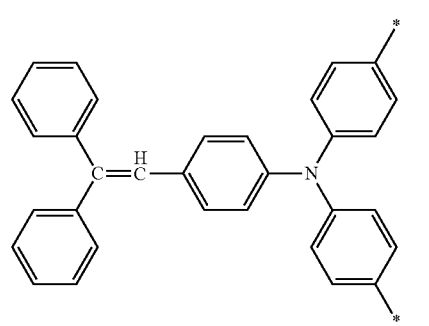
(2)-10
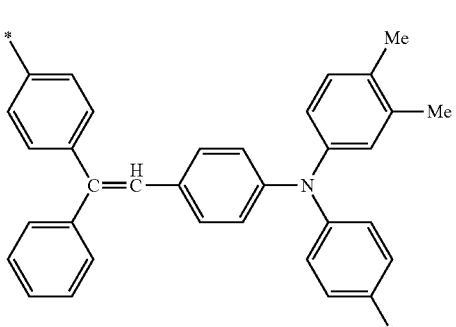
(2)-11
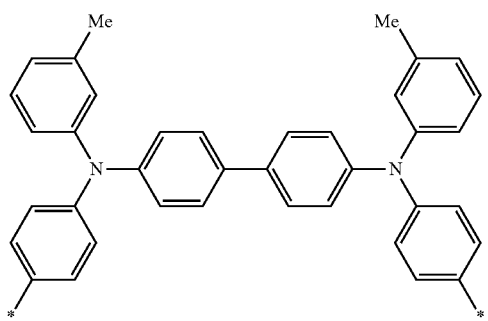
(2)-12
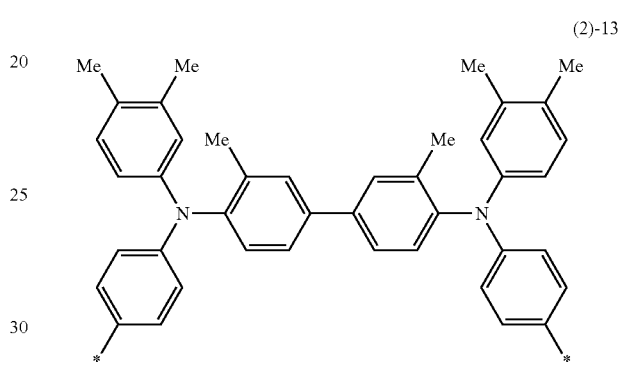
(2)-13
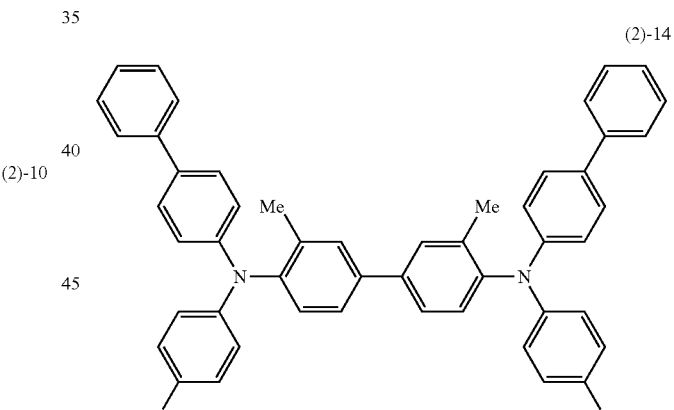
(2)-14
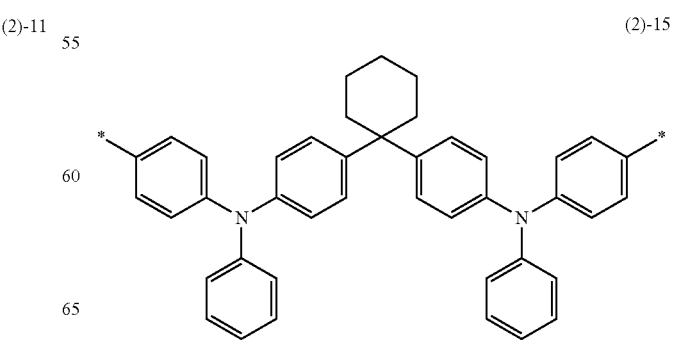
(2)-15

(2)-16
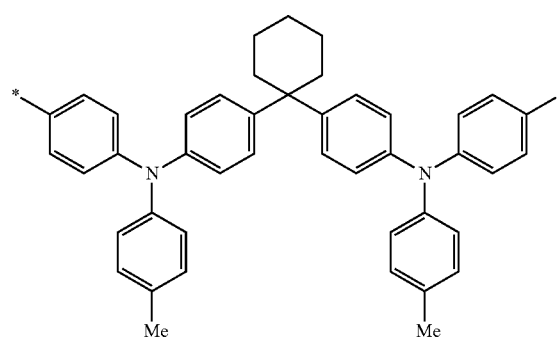
(2)-17
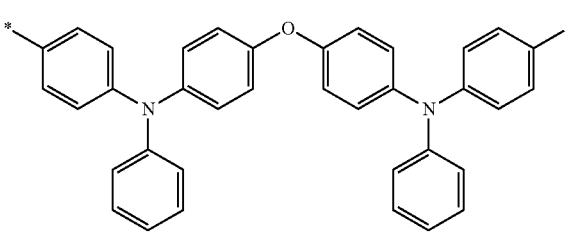
(2)-18
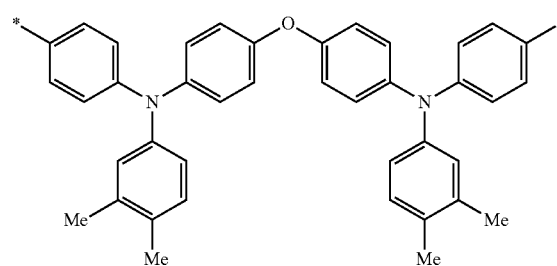
(2)-19
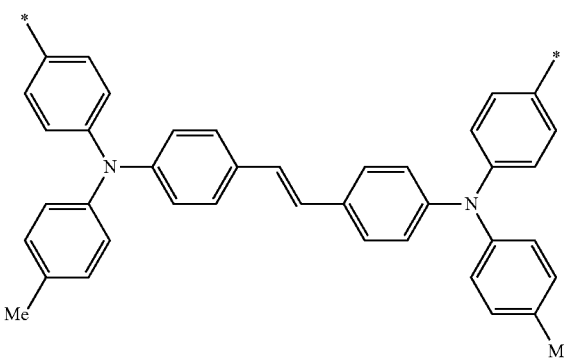
(2)-20
(2)-21
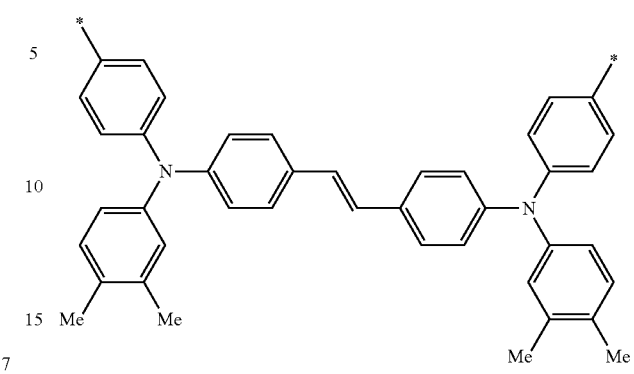
(2)-22
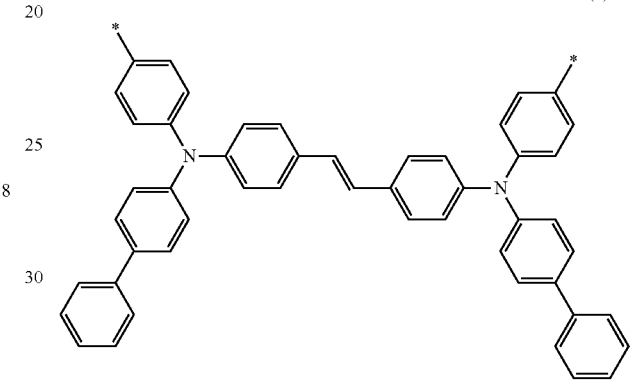
(2)-23
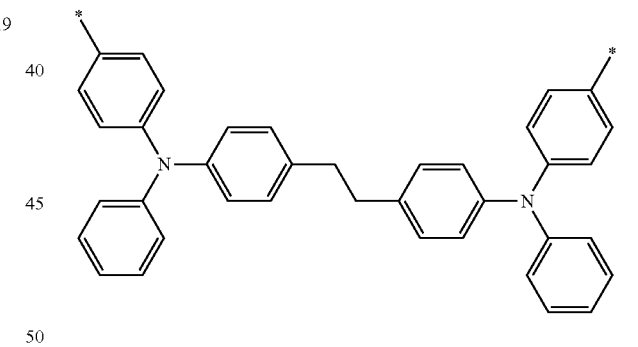
(2)-24
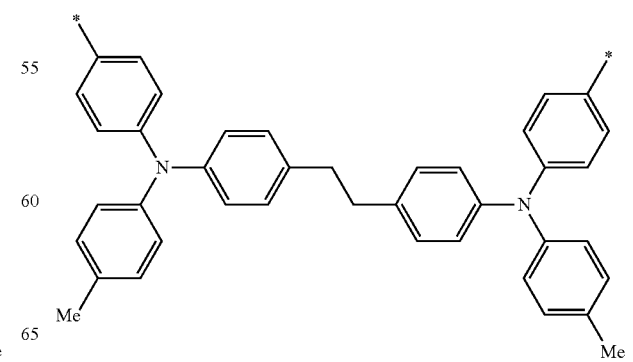

(2)-25
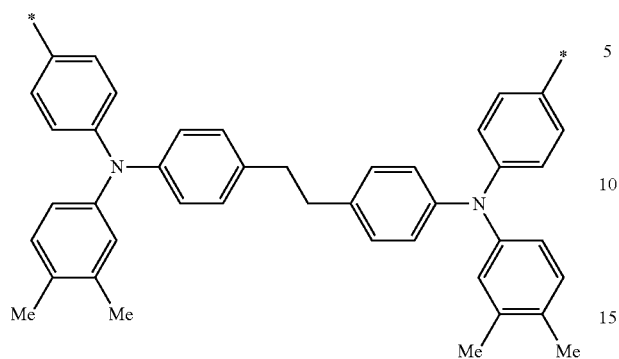
(2)-26
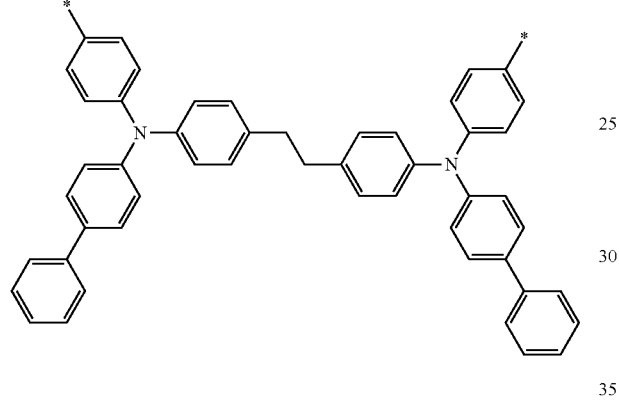
As trifunctional skeletons, the following ones are exemplified.
(3)-1
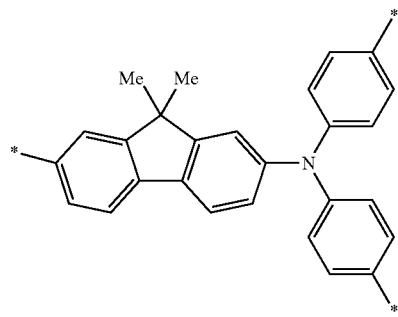
(3)-2
(3)-3
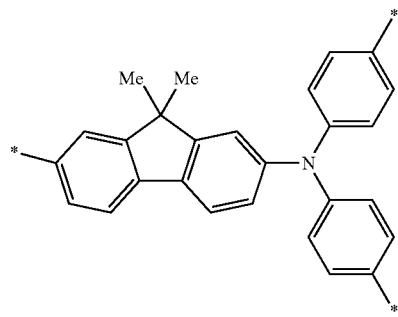
(3)-4
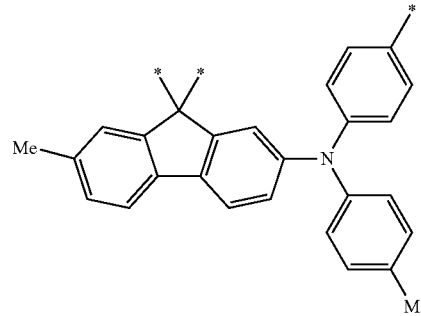
(3)-5
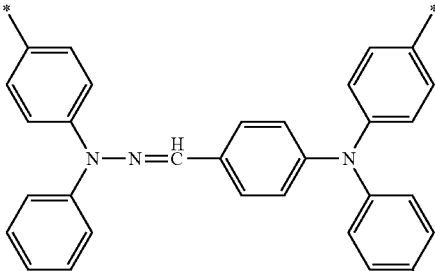
(3)-6
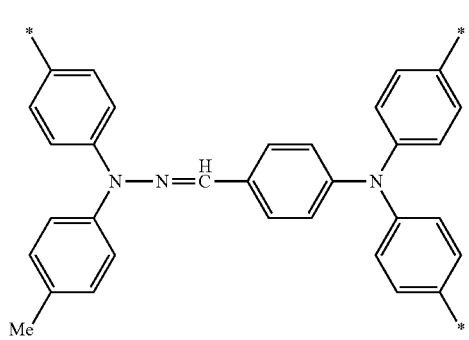
(3)-7
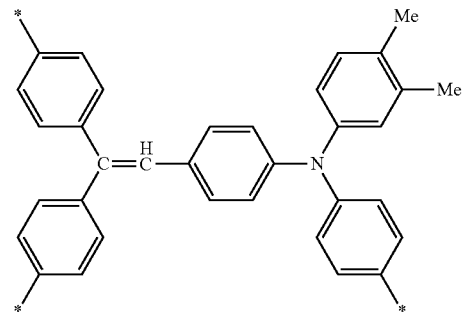

-continued
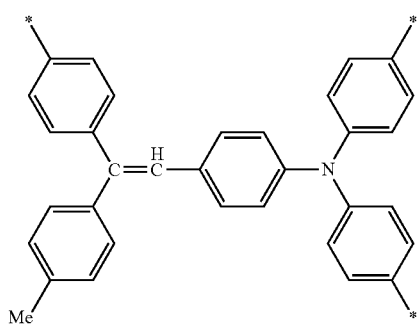
(3)-8
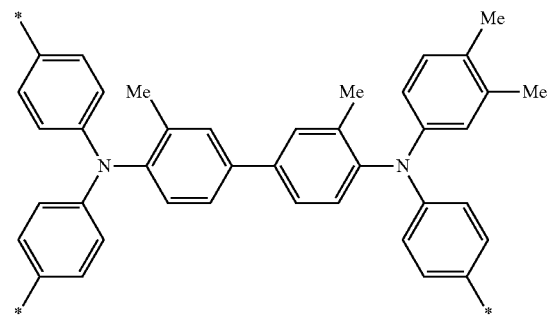
(3)-12
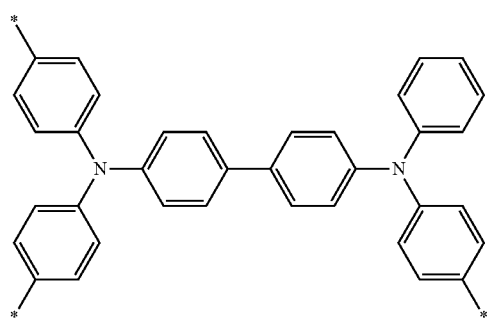
(3)-9
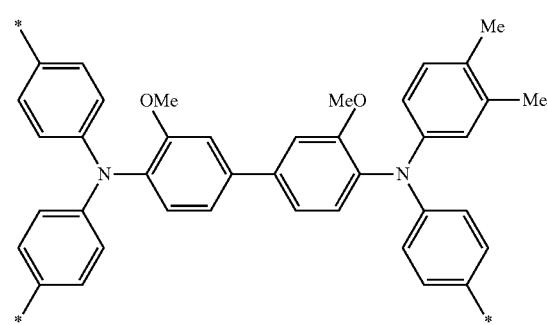
(3)-13
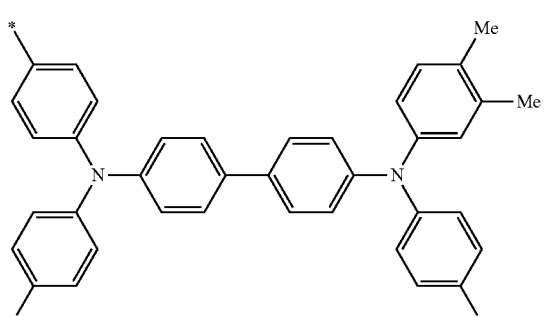
(3)-10
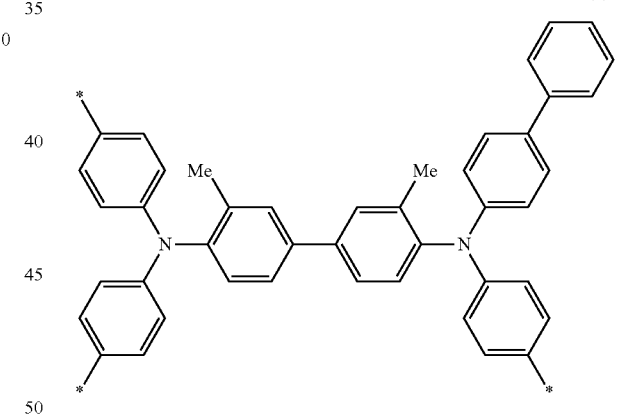
(3)-14
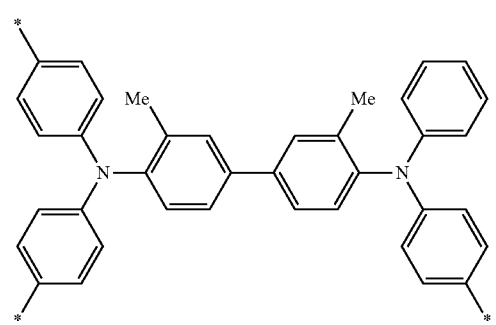
(3)-11
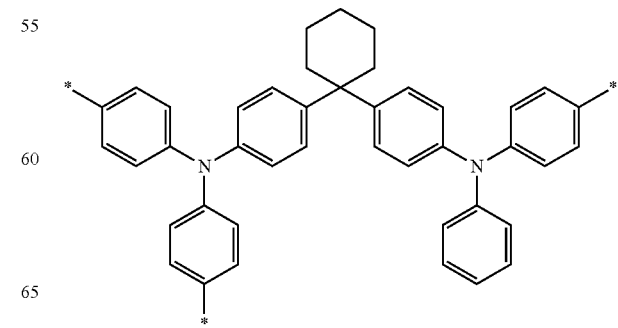
(3)-15

(3)-16
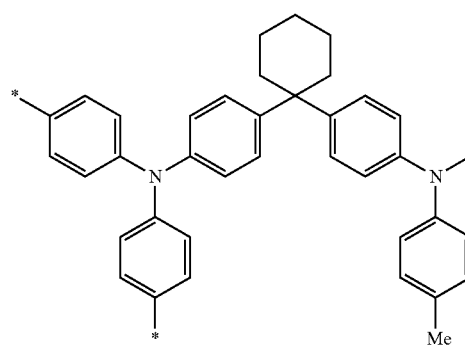
(3)-20
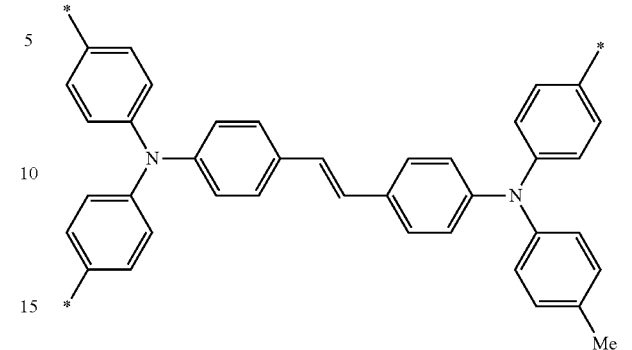
(3)-17
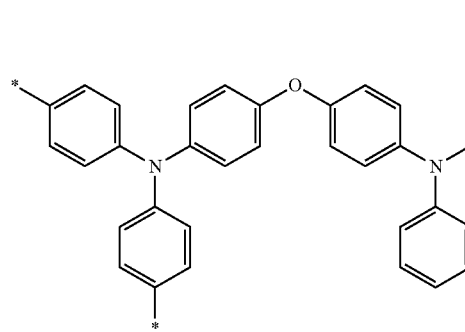
(3)-21
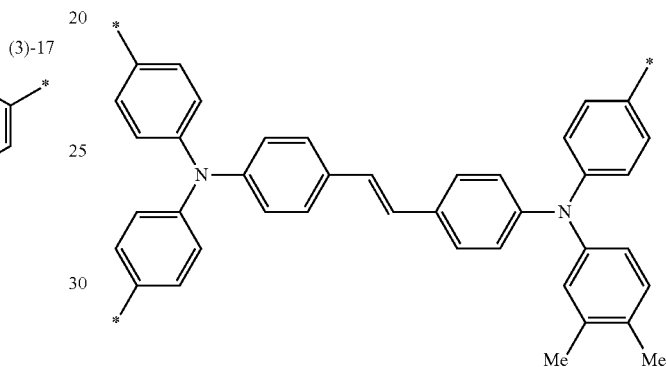
(3)-18
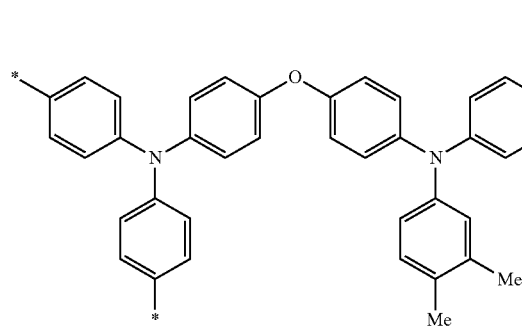
(3)-22
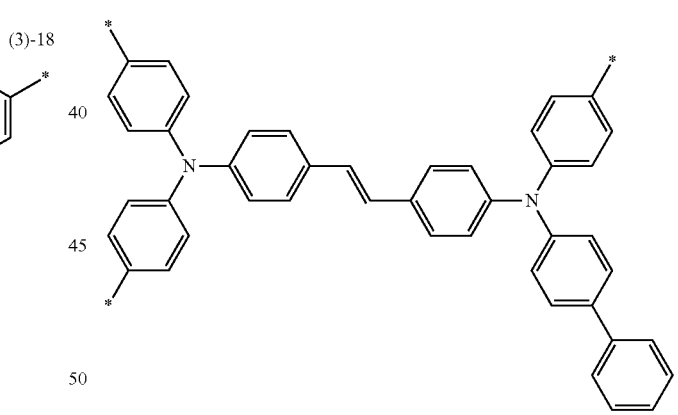
(3)-19
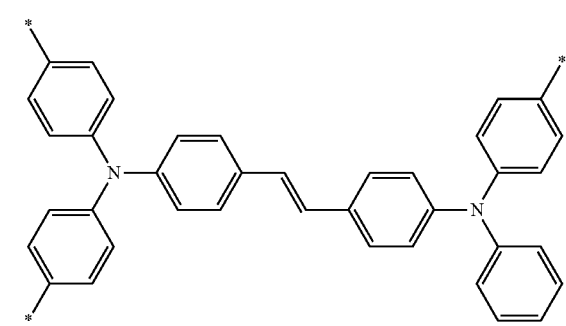
(3)-23
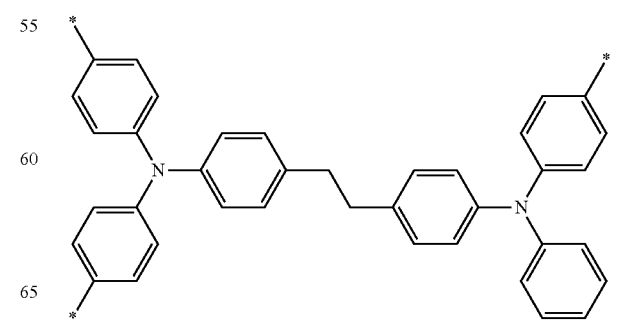

(3)-24
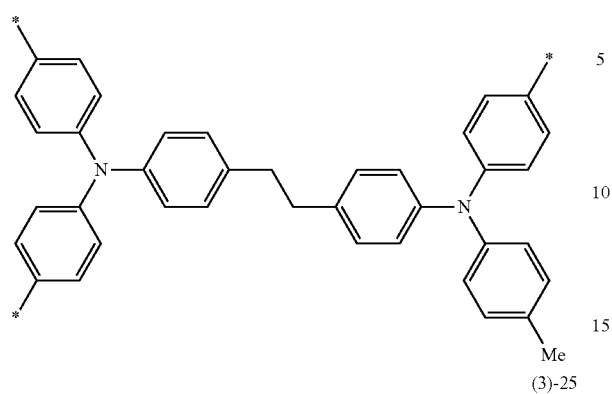
(3)-25
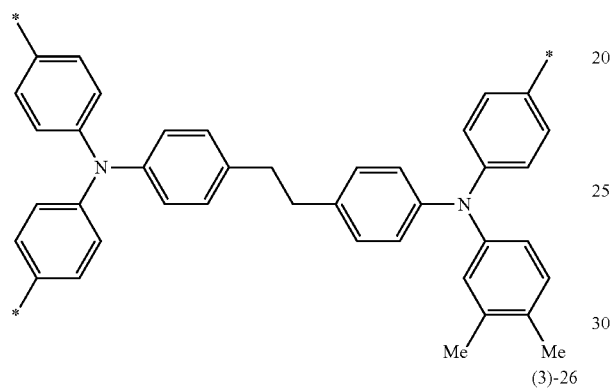
(3)-26
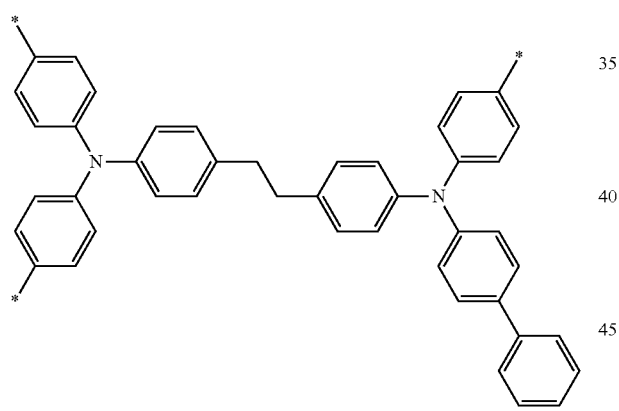
As tetrafunctional skeletons, the following ones are exemplified.
(4)-1
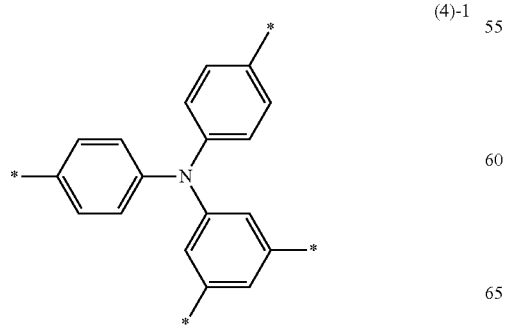
(4)-2
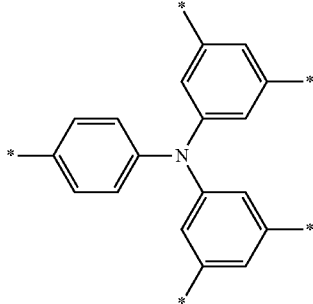
(4)-3
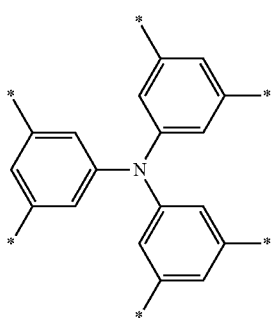
(4)-4
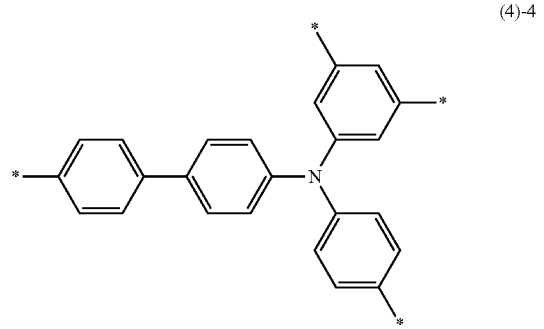
(4)-5
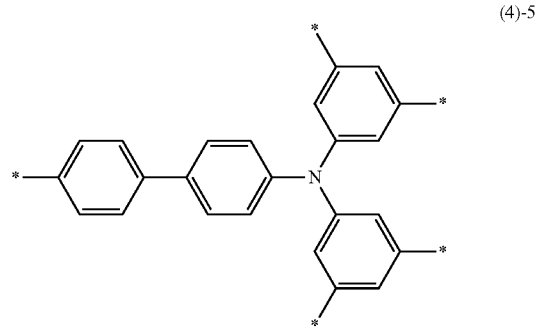
(4)-6
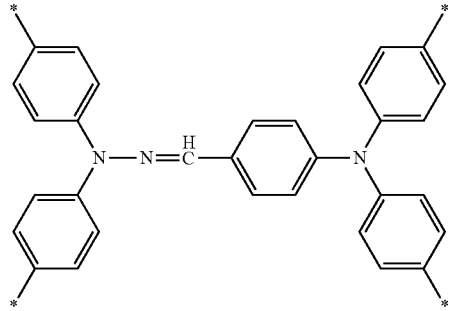

-continued
(4)-7
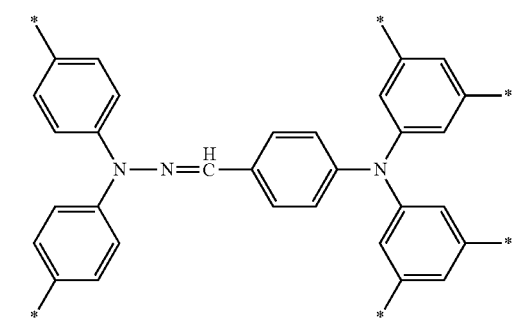
(4)-8
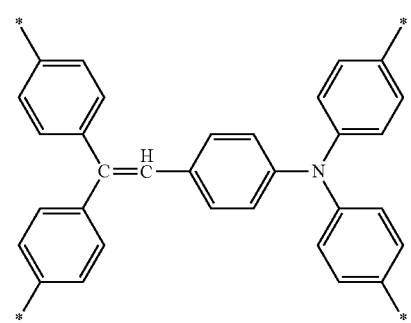
(4)-9
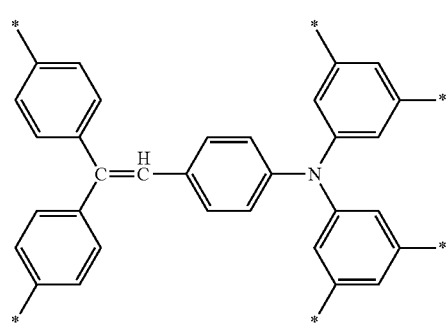
(4)-10
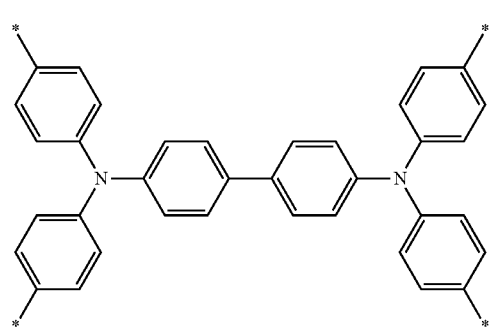
(4)-11
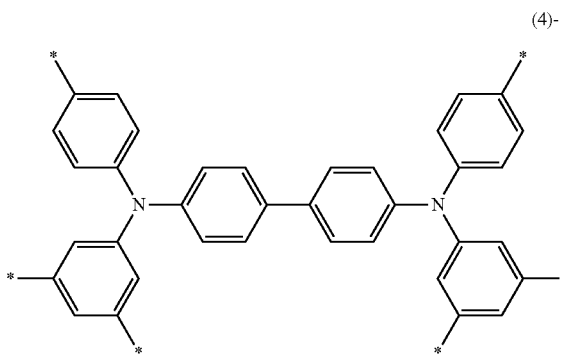
-continued
(4)-12
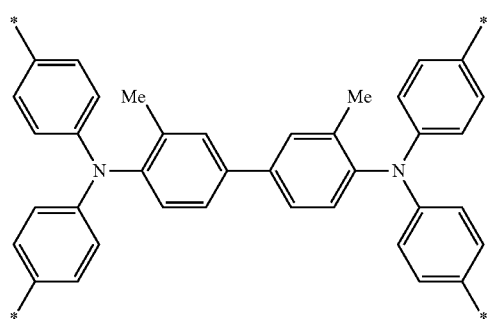
(4)-13
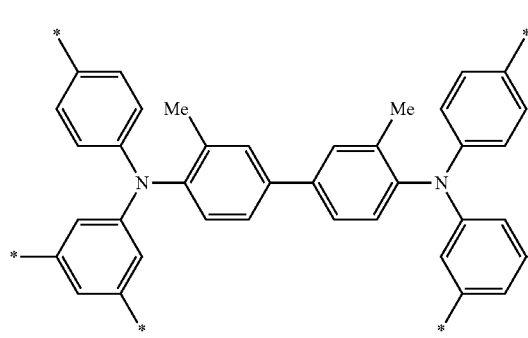
(4)-14
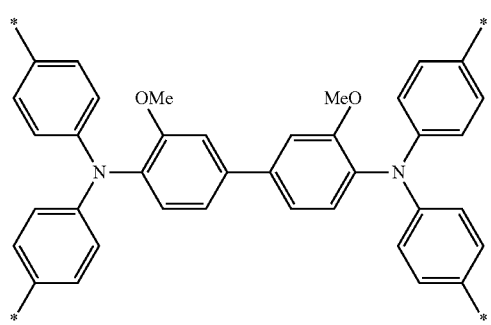
(4)-15
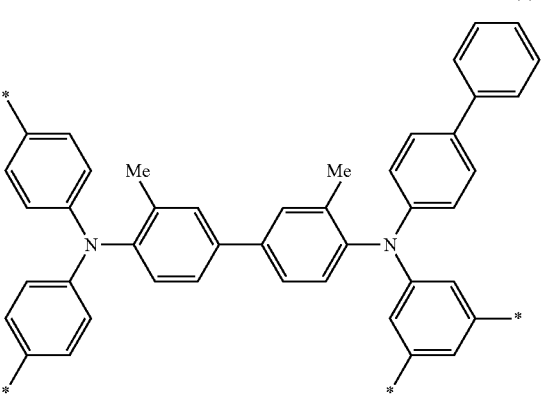

(4)-16
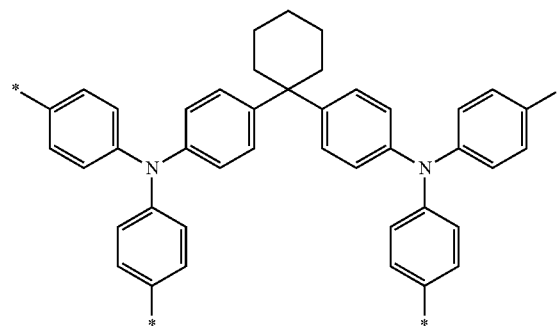
(4)-17
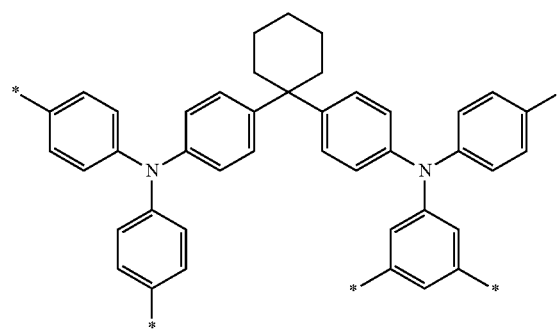
(4)-18
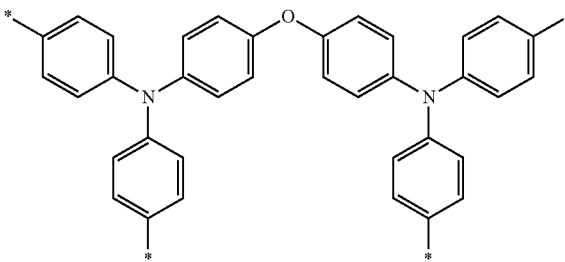
(4)-19
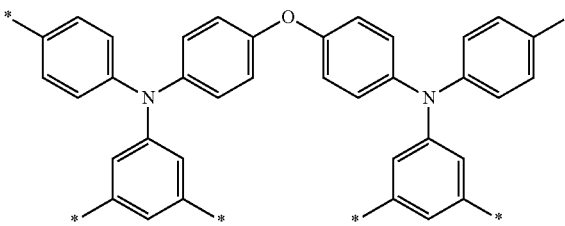
(4)-20
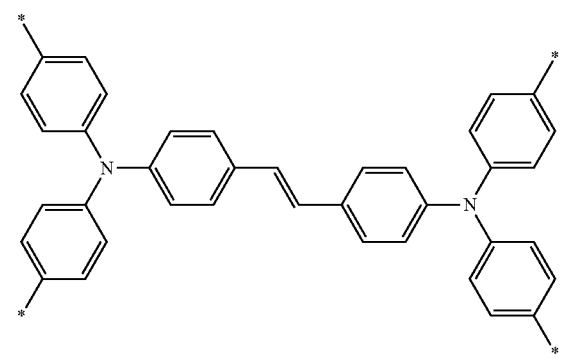
(4)-21
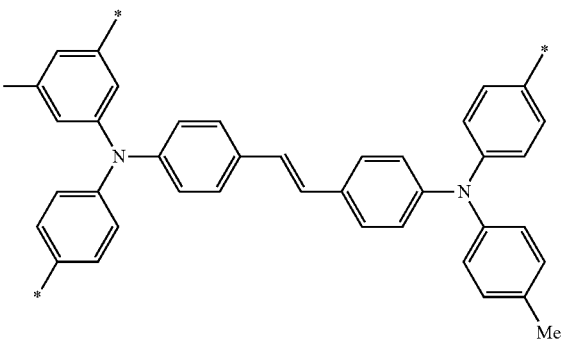
(4)-22
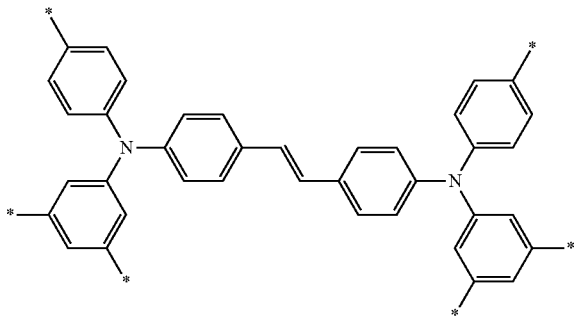
(4)-23
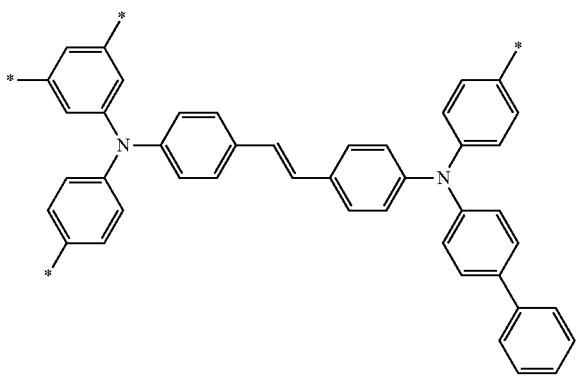
(4)-24
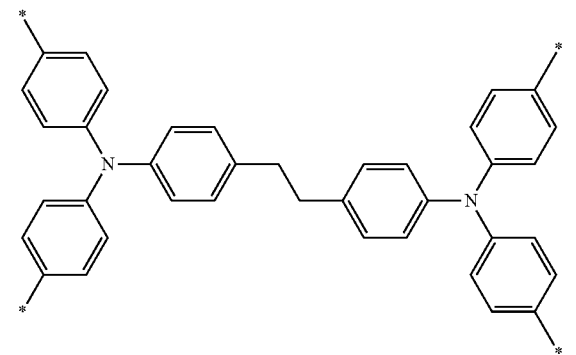

-continued (4)-25
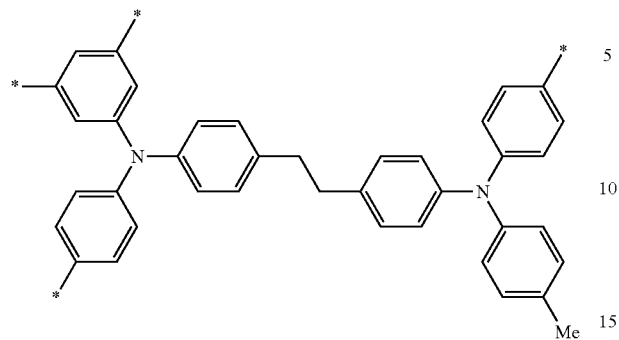

(4)-26
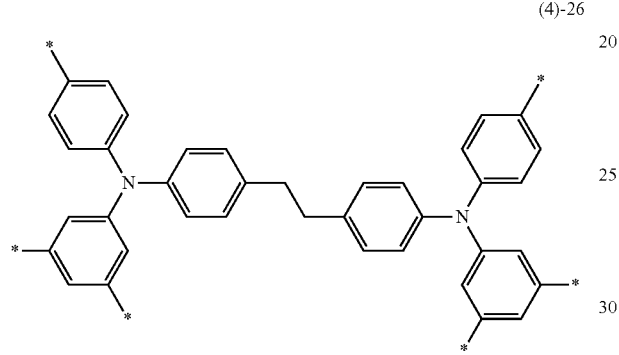

(4)-27
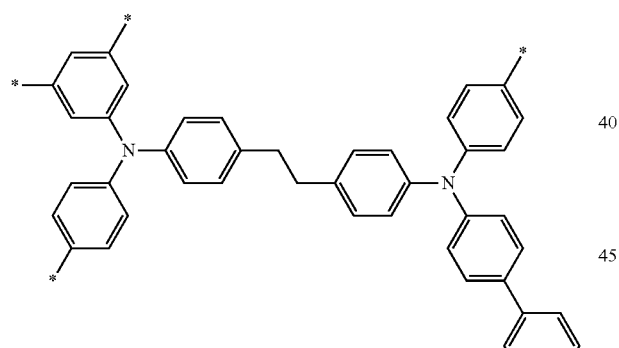

(4)-28
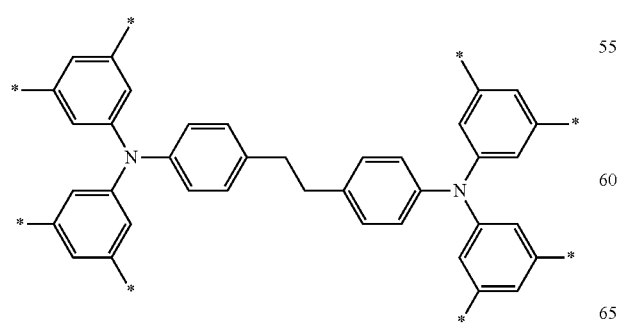

Specific examples of Formula (III) are shown below.

(III)-1
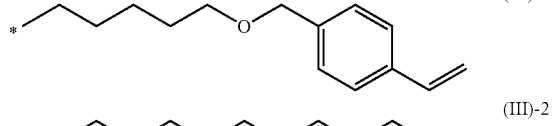

(III)-2
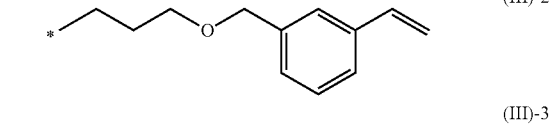

(III)-3
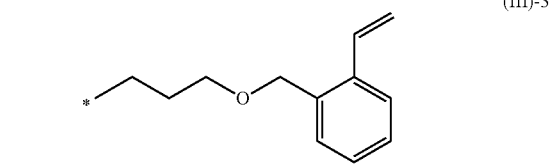

(III)-4
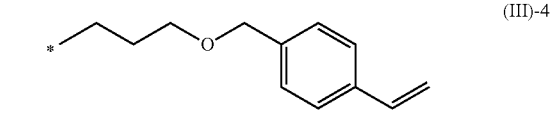

(III)-5
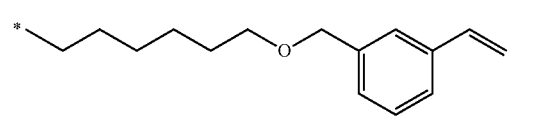

(III)-6
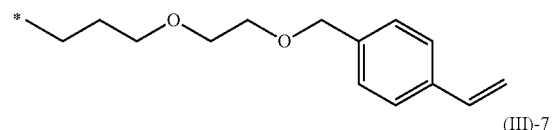

(III)-7
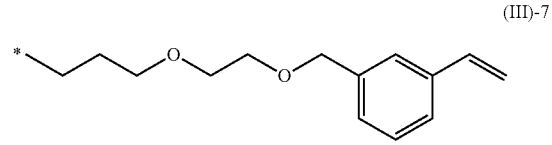

Hereinafter, specific examples of the compound represented by Formula (I) are shown in the following Tables 1 and 2, but the compound is not limited thereto.

TABLE 1

| Compound | Structure of Charge transporting skeleton | Structure of Formula (III) |
|---|---|---|
| (I)-1 | (1)-1 | (III)-1 |
| (I)-2 | (1)-1 | (III)-2 |
| (I)-3 | (1)-1 | (III)-4 |
| (I)-4 | (1)-2 | (III)-5 |
| (I)-5 | (1)-2 | (III)-7 |
| (I)-6 | (1)-4 | (III)-3 |
| (I)-7 | (1)-4 | (III)-5 |
| (I)-8 | (1)-5 | (III)-6 |
| (I)-9 | (1)-8 | (III)-4 |
| (I)-10 | (1)-16 | (III)-5 |
| (I)-11 | (1)-20 | (III)-1 |
| (I)-12 | (1)-22 | (III)-1 |
| (I)-13 | (2)-2 | (III)-1 |
| (I)-14 | (2)-2 | (III)-3 |
| (I)-15 | (2)-2 | (III)-4 |
| (I)-16 | (2)-6 | (III)-4 |
| (I)-17 | (2)-6 | (III)-5 |
| (I)-18 | (2)-6 | (III)-6 |
| (I)-19 | (2)-10 | (III)-4 |
| (I)-20 | (2)-10 | (III)-5 |
| (I)-21 | (2)-13 | (III)-1 |

TABLE 1-continued

| Compound | Structure of Charge transporting skeleton | Structure of Formula (III) |
|---|---|---|
| (I)-22 | (2)-13 | (III)-3 |
| (I)-23 | (2)-13 | (III)-4 |
| (I)-24 | (2)-13 | (III)-5 |
| (I)-25 | (2)-13 | (III)-6 |
| (I)-26 | (2)-16 | (III)-4 |
| (I)-27 | (2)-21 | (III)-5 |
| (I)-28 | (2)-25 | (III)-4 |
| (I)-29 | (2)-25 | (III)-5 |
| (I)-30 | (2)-25 | (III)-7 |

TABLE 2

| Compound | Structure of Charge transporting skeleton | Structure of Formula (III) |
|---|---|---|
| (I)-31 | (3)-1 | (III)-2 |
| (I)-32 | (3)-1 | (III)-7 |
| (I)-33 | (3)-5 | (III)-2 |
| (I)-34 | (3)-7 | (III)-4 |
| (I)-35 | (3)-7 | (III)-2 |
| (I)-36 | (3)-19 | (III)-4 |
| (I)-37 | (3)-26 | (III)-1 |
| (I)-38 | (3)-26 | (III)-3 |
| (I)-39 | (4)-3 | (III)-3 |
| (I)-40 | (4)-3 | (III)-4 |
| (I)-41 | (4)-8 | (III)-5 |
| (I)-42 | (4)-8 | (III)-6 |
| (I)-43 | (4)-12 | (III)-7 |
| (I)-44 | (4)-12 | (III)-4 |
| (I)-45 | (4)-12 | (III)-2 |
| (I)-46 | (4)-12 | (III)-11 |
| (I)-47 | (4)-16 | (III)-3 |
| (I)-48 | (4)-16 | (III)-4 |
| (I)-49 | (4)-20 | (III)-1 |
| (I)-50 | (4)-20 | (III)-4 |
| (I)-51 | (4)-20 | (III)-7 |
| (I)-52 | (4)-24 | (III)-4 |
| (I)-53 | (4)-24 | (III)-7 |
| (I)-54 | (4)-24 | (III)-3 |
| (I)-55 | (4)-24 | (III)-4 |
| (I)-56 | (4)-25 | (III)-1 |
| (I)-57 | (4)-26 | (III)-3 |
| (I)-58 | (4)-28 | (III)-4 |
| (I)-59 | (4)-28 | (III)-5 |
| (I)-60 | (4)-28 | (III)-6 |
| (I)-61 | (1)-2 | (III)-4 |
| (I)-62 | (1)-4 | (III)-4 |
| (I)-63 | (2)-3 | (III)-4 |
| (I)-64 | (2)-25 | (II)-2 + (III)-4 |

Examples of the use of the compound according to the exemplary embodiment include a charge transporting film that includes the compound represented by Formula (I) or the structure derived from the compound. For example, by curing a composition that contains the compound according to the exemplary embodiment, a charge transporting film having electrical characteristics and high strength is obtained.

In the exemplary embodiment, a photoelectric conversion device is provided which includes the charge transporting film obtained using the compound represented by Formula (I). The compound is useful as a charge transporting layer or a protective layer configuring the electrophotographic photoreceptor that includes the charge transporting film obtained using the compound according to the exemplary embodiment, or as a charge transporting layer of an organic electroluminescence element.

[Electrophotographic Photoreceptor]

The electrophotographic photoreceptor according to the exemplary embodiment includes a conductive substrate and a photosensitive layer provided on the conductive substrate. The uppermost surface layer of the electrophotographic photoreceptor includes the specific charge transport material (a) or a structure derived from the charge transport material (a), and is formed as a cured film of the composition containing the specific charge transport material (a).

In the electrophotographic photoreceptor according to the exemplary embodiment, due to the above-described configuration, the mechanical strength of the uppermost surface layer is high, and the electrical characteristics and image characteristics may remain stable even if the electrophotographic photoreceptor is repeatedly used over a long time.

The specific charge transport material (a) has a styryl group in the molecule thereof. Therefore, if the charge transport material (a) is used, a cured film having a high crosslink density is obtained, and an uppermost surface layer having a sufficient mechanical strength may be formed.

From the structure of the specific charge transport material (a), a highly viscous composition is obtained. Accordingly, volumetric shrinkage does not easily occur when the cured film using this composition is obtained, and an uppermost surface layer excellent in surface properties is obtained.

In addition, by using the specific charge transport material (a), the uppermost surface layer having a high crosslink density and sufficient mechanical strength may be formed as described above. Accordingly, it is not necessary to add polyfunctional monomers that do not have a charge transport property, and the thickness of the uppermost surface layer is increased without the deterioration of the electrical characteristics caused by the addition of the polyfunctional monomers. As a result, the life of the electrophotographic photoreceptor including such an uppermost surface layer is extended, and the electrophotographic photoreceptor may be tolerant of long-term use.

Particularly, when the electrophotographic photoreceptor is used over a long time, the surface of the electrophotographic photoreceptor is contaminated by the attachment of substances called discharge products generated by corona discharge or the attachment of toners, external additives, and the like, and image defects occurs in many cases. To avoid such phenomena, it is effective to use the electrophotographic photoreceptor while very slightly scraping off the contaminated layer of the surface. However, if the surface is scraped off more than necessary, the life of the electrophotographic photoreceptor is shortened. Therefore, ideally, the strength of the surface layer of the photoreceptor is controlled according to the usage conditions. To do this, unreactive charge transport materials, reactive charge transport materials differing in the number of functional groups and types, reactive/unreactive resins, reactive monomers or oligomers that do not have the charge transport property and differ in the number of functional groups and types, and the like are added, whereby the strength is adjusted.

Specifically, the cured films of the following embodiments are exemplified.

(1) An embodiment that reacts with the specific charge transport material (a) and further contains monomers or oligomers not having a charge transport property (2) An embodiment that further contains polymers not reacting with the specific charge transport material (a)

(3) An embodiment that further contains polymers reacting with the specific charge transport material (a)

(4) An embodiment that reacts with the specific charge transport material (a) and further contains a charge transport compound having a charge transport property The electrophotographic photoreceptor according to the exemplary embodiment has an uppermost surface layer including a composition containing at least one kind of the specific charge transport material (a) or a cured film of the composition. However, the uppermost surface layer may form the uppermost surface of the electrophotographic photoreceptor itself, and is provided as a layer functioning as a protective layer or functioning as a charge transporting layer.

When the uppermost surface layer is a layer functioning as a protective layer, in a layer below the protective layer, a photosensitive layer including a charge transporting layer and a charge generating layer or a single layer type photosensitive layer (charge generating/charge transporting layer) is provided.

When the uppermost surface layer functions as a protective layer, an embodiment is exemplified in which a photosensitive layer and a protective layer as the uppermost surface layer are provided on the conductive substrate, and the protective layer is configured with a composition containing at least one kind of the specific charge transport material (a) or a cured film of the composition.

On the other hand, when the uppermost surface layer functions as a charge transporting layer, an embodiment is exemplified in which a charge generating layer and a charge transporting layer as the uppermost surface layer are provided on the conductive substrate, and the charge transporting layer is configured with a composition containing at least one kind of the specific charge transport material (a) or a cured film of the composition.

Hereinafter, the electrophotographic photoreceptor according to the exemplary embodiment in a case where the uppermost surface layer functions as a protective layer will be described in detail with reference to drawings. In the drawings, the same or corresponding portions are marked with the same reference numerals, thereby omitting the repeated descriptions.

Figure 2:
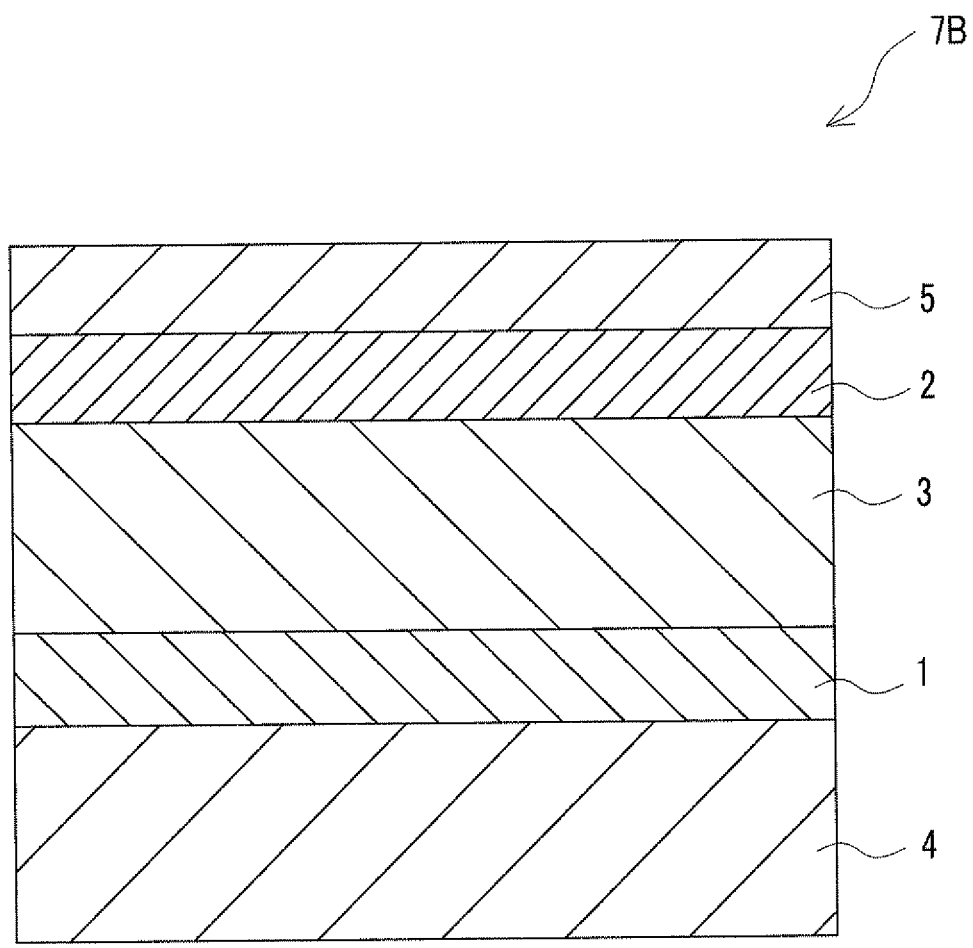
FIG. 2 is a schematic partial cross-sectional view showing the electrophotographic photoreceptor according to the exemplary embodiment.
Figure 3:
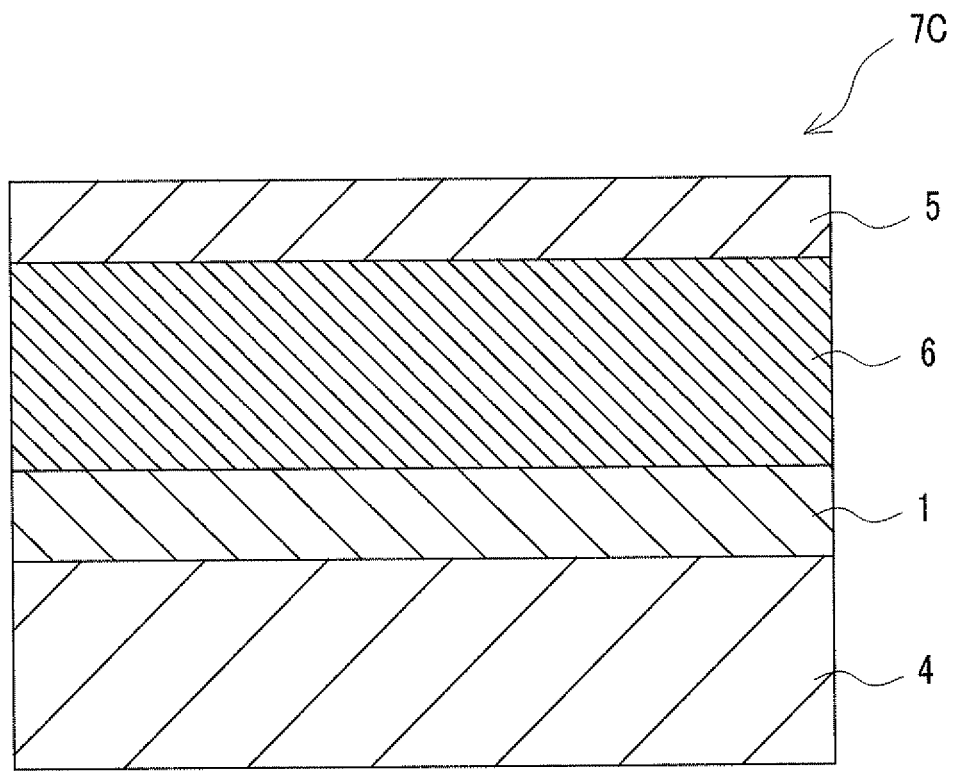
FIG. 3 is a schematic partial cross-sectional view showing the electrophotographic photoreceptor according to the exemplary embodiment.

FIG. 1 is a schematic cross-sectional view showing a suitable exemplary embodiment of the electrophotographic photoreceptor according to the exemplary embodiment. FIGS. 2 and 3 are respectively schematic cross-sectional views showing the electrophotographic photoreceptor according to another exemplary embodiment.

An electrophotographic photoreceptor 7A shown in FIG. 1 is a so-called functional separation type photoreceptor (or a layered type photoreceptor), and has a structure in which an undercoat layer 1 is provided on a conductive substrate 4, and a charge generating layer 2, a charge transporting layer 3, and a protective layer 5 are sequentially formed on the undercoat layer 1. In the electrophotographic photoreceptor 7A, a photosensitive layer is configured with the charge generating layer 2 and the charge transporting layer 3.

An electrophotographic photoreceptor 7B shown in FIG. 2 is a functional separation type photoreceptor in which the functions are divided into the charge generating layer 2 and the charge transporting layer 3 similarly to the electrophotographic photoreceptor 7A shown in FIG. 1. An electrophotographic photoreceptor 7C shown in FIG. 3 contains the charge generating material and the charge transporting material (single layer type photosensitive layer 6 (charge generating/charge transporting layer)) in the same layer.

The electrophotographic photoreceptor 7B shown in FIG. 2 has a structure in which the undercoat layer 1 is provided on the conductive substrate 4, and the charge transporting layer 3, the charge generating layer 2, and the protective layer 5 are sequentially formed on the undercoat layer 1. In the electrophotographic photoreceptor 7B, a photosensitive layer is configured with the charge transporting layer 3 and the charge generating layer 2.

In addition, the electrophotographic photoreceptor 7C shown in FIG. 3 has a structure in which the undercoat layer 1 is provided on the conductive substrate 4, and the single layer type photosensitive layer 6 and the protective layer 5 are sequentially formed on the undercoat layer 1.

In the electrophotographic photoreceptors 7A to 7C shown in FIGS. 1 to 3, the protective layer 5 becomes an uppermost surface layer disposed farthest away from the conductive substrate 4, and the uppermost surface layer is configured with the specific charge transport material (a) or a structure derived from the charge transport material (a). Herein, the "structure derived from the specific charge transport material (a)" refers to a polymer of the specific charge transport material (a), or a copolymer of the specific charge transport material (a) with another compound that has or does not have a charge transport property.

In the electrophotographic photoreceptors shown in FIGS. 1 to 3, the undercoat layer 1 may or may not be provided.

Hereinafter, the respective elements will be described based on the electrophotographic photoreceptor 7A shown in FIG. 1 as a representative example.

<Protective Layer>

First, the protective layer 5 as the uppermost surface layer of the electrophotographic photoreceptor 7A will be described.

The protective layer 5 is the uppermost surface layer of the electrophotographic photoreceptor 7A, and includes a composition that contains at least one kind of the specific charge transport material (a) or a cured film of the composition. The specific charge transport material (a) is as described above.

The compound represented by Formula (I) is synthesized in the following manner.

That is, the compound represented by Formula (I) is synthesized through esterification or the like performed using an alcohol as a precursor and the corresponding chloromethylstyrene.

The synthesis pathway of a compound (I)-44 according to the exemplary embodiment is shown below as an example.

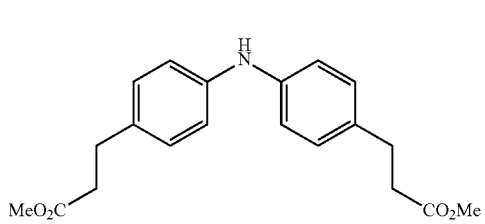 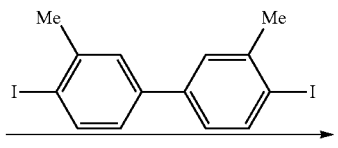

-continued

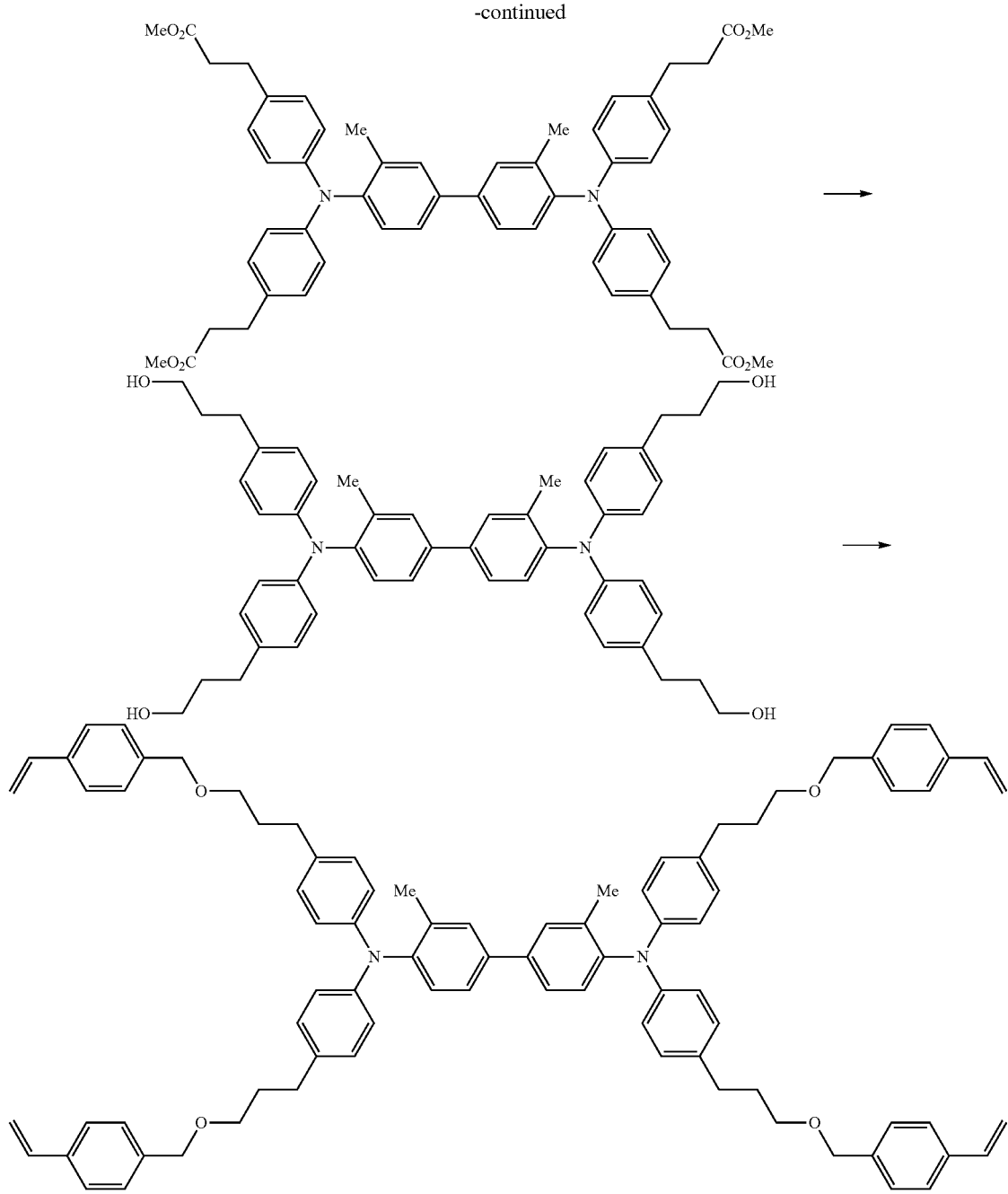

The total content of the specific charge transport material (a) is desirably from 30% by mass to 100% by mass, more desirably from 35% by mass to 100% by mass, and even more desirably from 40% by mass to 100% by mass, based on the composition (total solid contents amount) used for forming the protective layer (uppermost surface layer) 5.

In this range, the electrical characteristics of the cured film (uppermost surface layer) become excellent, and the thickness of the cured film increases.

(Other Charge Transport Materials)

The cured film configuring the protective layer (uppermost surface layer) 5 may optionally use a known charge transport material not having a reactive group and plural charge transport materials differing in the number and types of reactive groups, in addition to the specific charge transport material (a) described above. Herein, the reactive group refers to a radical-polymerizable functional group such as a vinyl group, an allyl group, a styryl group, an acryl group, or a methacryl group.

The known charge transport material not having a reactive group does not have a reactive group which does not conduct charge transport. Accordingly, for example, if this known charge transport material is used concurrently, the concentration of the charge transporting components is substantially increased, whereby the electrical characteristics of the cured film (uppermost surface layer) may be further improved. In addition, the known charge transport material not having a reactive group may help adjusting the strength of the cured film (uppermost surface layer). Moreover, having a charge transporting skeleton, the specific charge transport material (a) is highly compatible with the known charge transport material not having a reactive group. Consequently, the charge transport material in the related art that does not have a reactive group is doped, in order that the further improvement of the electrical characteristics is assured.

On the other hand, when the plural charge transport materials differing in the number and types of reactive groups are used concurrently, the crosslink density is adjusted without decreasing the amount of the charge transporting skeleton. Therefore, the strength of the cured film (uppermost surface layer) is adjusted while maintaining the electrical characteristics.

Hereinafter, the charge transport material that may be concurrently used with the specific charge transport material (a) will be described.

As the known charge transport material not having a reactive group, for example, materials are used which will be exemplified later as charge transport materials configuring the charge transporting layer 3. Among those materials, a material containing a triphenylamine skeleton is desirably used in view of mobility, compatibility, and the like.

Examples of the charge transport materials differing in the number and types of reactive groups include known materials obtained by introducing a radical-polymerizable functional group such as a vinyl group, an allyl group, a styryl group, an acryl group, or a methacryl group to charge transport materials. Among these, compounds having a triphenylamine skeleton and a styryl group, an acryl group, or a methacryl group in the same molecule is desirable in view of mobility, compatibility, and the like.

Other charge transport materials described so far are used desirably at from 0% by mass to 70% by mass, more desirably at from 0% by mass to 65% by mass, and even more desirably at from 0% by mass to 60% by mass, based on the specific charge transport material (a).

(Catalyst)

The composition containing the specific charge transport material (a) described above is cured by being polymerized with light, electron beams, or heat. For this polymerization and curing reaction, a curing catalyst (polymerization initiator) may not be used, but the reaction effectively proceeds if curing catalysts exemplified below are used.

Examples of the photocuring catalyst include an intramolecular cleavage type or a hydrogen abstraction type of photocuring catalyst.

Examples of the intramolecular cleavage type of curing catalyst include curing catalysts based on benzylketal, alkylphenone, aminoalkylphenone, phosphine oxide, titanocene, and oxime.

Specifically, examples of the benzylkatal-based curing catalyst include 2,2-dimethoxy-1,2-diphenylethan-1-one.

Examples of the alkylphenone-based photocuring catalyst include 1-hydroxy-cyclohexyl-phenyl-ketone, 2-hydroxy-2-methyl-1-phenyl-propan-1-one, 1-[4-(2-hydroxyethoxy)-phenyl]-2-hydroxy-2-methyl-1-propan-1-one, 2-hydroxy-1-{4-[4-(2-hydroxy-2-methyl-propionyl)-benzyl]phenyl}-2-methyl-propan-1-one, acetophenone, and 2-phenyl-2-(p-toluenesulfonyloxy)acetophenone.

Examples of the aminoalkylphenone-based curing catalyst include p-dimethylaminoacetophenone, p-dimethylamino-propiophenone, 2-methyl-1-(4-methylthiophenyl)-2-morpholinopropan-1-one, 2-benzyl-2-dimethylamino-1-(4-morpholinophenyl)-butanone-1,2-(dimethylamino)-2-[(4-methylphenyl)methyl]-1-[4-(4-morpholinyl)phenyl]-1-butanone, and the like.

Examples of the phosphine oxide-based curing catalyst include 2,4,6-trimethylbenzoyl-diphenyl-phosphine oxide, bis(2,4,6-trimethylbenzoyl)-phenylphosphine oxide, and the like.

Examples of the titanocene-based curing catalyst include bis(η5-2,4-cyclopentadiene-1-yl)-bis(2,6-difluoro-3-(1H-pyrrol-1-yl)-phenyl)titanium and the like.

Examples of the oxime-based curing catalyst include 1,2-octanedione, 1-[4-(phenylthio)-, 2-(O-benzoyloxime)], ethanone, 1-[9-ethyl-6-(2-methylbenzoyl)-9H-carbazole-3-yl]-, 1-(O-acetyloxime) and the like.

Examples of the hydrogen abstraction type of curing catalyst include curing catalysts based on benzophenone, thioxanthone, benzyl, Michler ketone, and the like.

Specific examples of the hydrogen abstraction type of curing catalyst based on benzophenone include 2-benzoyl benzoate, 2-chlorobenzophenone, 4,4'-dichlorobenzophenone, 4-benzoyl 4'-methyldiphenyl sulfide, p,p'-bisdiethylaminobenzophenone, and the like.

Examples of the hydrogen abstraction type of curing catalyst based on thioxanthone include 2,4-diethylthioxanthen-9-one, 2-chlorothioxanthone, 2-isopropylthioxanthone, and the like.

Examples of the hydrogen abstraction type of curing catalyst based on benzyl include benzyl, (±)-camphorquinone, p-anisil, and the like.

As the curing catalyst used for thermal curing, known thermal polymerization initiators may be used, and specifically, commercially available curing catalysts (thermal polymerization initiators) shown below are desirably used.

That is, examples of the commercially available products of the thermal polymerization initiator include azo-based initiators such as V-30, V-40, V-59, V-601, V-65, V-70, VF-096, Vam-110, and Vam-111 (manufactured by Wako Pure Chemical Industries, Ltd.); $OT_{AZO}$-15, $OT_{AZO}$-30, AIBN, AMBN, ADVN, and ACVA (manufactured by Otsuka Chemical Co., Ltd.); and the like.

In addition, the examples also include Pertetra A, Perhexa HC, Perhexa C, Perhexa V, Perhexa 22, Perhexa MC, Perbutyl H, Percumyl H, Percumyl P, Permenta H, Perocta H, Perbutyl C, Perbutyl D, Perhexyl D, Peroyl IB, Peroyl 355, Peroyl L, Peroyl SA, Nyper BW, Nyper BMT-K40/M, Peroyl IPP, Peroyl NPP, Peroyl TCP, Peroyl OPP, Peroyl SBP, Percumyl ND, Perocta ND, Perhexyl ND, Perbutyl ND, Perbutyl NHP, Perhexyl PV, Perbutyl PV, Perhexa 250, Perocta O, Perhexyl O, Perbutyl O, Perbutyl L, Perbutyl 355, Perhexyl I, Perbutyl I, Perbutyl E, Perhexa 25Z, Perbutyl A, Perhexyl Z, Perbutyl ZT, and Perbutyl Z (manufactured by NOF CORPORATION);

Kayaketal AM-C55, Trigonox 36-C75, Laurox, Perkadox L-W75, PerkadoxCH-50L, Trigonox TMBH, Kayacumene H, Kayabutyl H-70, Perkadox BC-FF, Kayahexa AD, Perkadox 14, Kayabutyl C, Kayabutyl D, Kayahexa YD-E85, Perkadox 12-XL25, Perkadox 12-EB20, Trigonox 22-N70, Trigonox 22-70E, Trigonox D-T50, Trigonox 423-C70, Kayaester CND-C70, Kayaester CND-W50, Trigonox 23-C70, Trigonox 23-W50N, Trigonox 257-C70, Kayaester P-70, Kayaester TMPO-70, Trigonox 121, Kayaester O, Kayaester HTP-65W, Kayaester AN, Trigonox 42, Trigonox F-C50, Kayabutyl B, Kayacarbon EH-C70, Kayacarbon EH-W60, Kayacarbon I-20, Kayacarbon BIC-75, Trigonox 117, and Kayalene 6-70 (manufactured by KAYAKU AKZO CO., LTD.);

Luperox 610, Luperox 188, Luperox 844, Luperox 259, Luperox 10, Luperox 701, Luperox 11, Luperox 26, Luperox 80 Luperox 7, Luperox 270, Luperox P, Luperox 546, Luperox 554, Luperox 575, Luperox TANPO, Luperox 555, Luperox 570, Luperox TAP, Luperox TBIC, Luperox TBEC, Luperox JW, Luperox TAIC, Luperox TAEC, Luperox DC, Luperox 101, Luperox F, Luperox D1, Luperox 130, Luperox 220, Luperox 230, Luperox 233, and Luperox 531 (manufactured by ARKEMA YOSHITOMI, LTD.); and the like.

These curing catalysts are added desirably in a range of from 0.2% by mass to 10% by mass, more desirably in a range of from 0.5% by mass to 8% by mass, and even more desirably in a range of from 0.7% by mass to 5% by mass, based on the total solid contents in the composition containing the specific charge transport material (a).

The composition containing the specific charge transport material (a) according to the exemplary embodiment may contain a reactive compound (b) that does not have a charge transport property. With the use of the specific charge transport material (a), the protective layer 5 (uppermost surface layer) that secures sufficient electrical characteristics and mechanical strength is obtained. Therefore, by concurrently using the reactive compound (b) that does not have a charge transport property, the mechanical strength of the protective layer 5 (uppermost surface layer) may be adjusted.

Herein, the words "does not have a charge transport property" means that carrier transport is not observed by a Time of Flight method.

Examples of the reactive compound include a monofunctional or polyfunctional polymerizable monomer, oligomer, and polymer, such as a monomer, oligomer, and polymer of acrylate or methacrylate.

Specific examples of the monofunctional monomer include isobutyl acrylate, t-butyl acrylate, isooctyl acrylate, lauryl acrylate, stearyl acrylate, isobornyl acrylate, cyclohexyl acrylate, 2-methoxyethyl acrylate, methoxy triethylene glycol acrylate, 2-ethoxyethyl acrylate, tetrahydrofurfuryl acrylate, benzyl acrylate, ethyl carbitol acrylate, phenoxyethyl acrylate, 2-hydroxy acrylate, 2-hydroxypropyl acrylate, 4-hydroxybutyl acrylate, methoxy polyethylene glycol acrylate, methoxy polyethylene glycol methacrylate, phenoxy polyethylene glycol acrylate, phenoxy polyethylene glycol methacrylate, hydroxyethyl o-phenylphenol acrylate, o-phenylphenol glycidyl ether acrylate, and the like.

Examples of the bifunctional monomer, oligomer, and polymer include diethylene glycol di(meth)acrylate, polyethylene glycol di(meth)acrylate, polypropylene glycol di(meth)acrylate, neopentyl glycol di(meth)acrylate, 1,6-hexanediol di(meth)acrylate, and the like.

Examples of the trifunctional monomer, oligomer, and polymer include trimethylolpropane tri(meth)acrylate, pentaerythritol tri(meth)acrylate, aliphatic tri(meth)acrylate, and the like.

Examples of the tetrafunctional monomer, oligomer, and polymer include pentaerythritol tetra(meth)acrylate, ditrimethylolpropane tetra(meth)acrylate, aliphatic tetra(meth)acrylate, and the like.

Examples of the pentafunctional or higher functional monomer, oligomer, and polymer include (meth)acrylates and the like having a polyester skeleton, a urethane skeleton, or a phosphazene skeleton, in addition to dipentaerythritol penta(meth)acrylate and dipentaerythritol hexa(meth)acrylate.

The monomer, oligomer, and polymer described above are used alone or as a mixture of two or more kinds thereof.

In addition, the monomer, oligomer, and polymer described above are used at 50% by mass or less, desirably at 40% by mass or less, and more desirably at 30% by mass or less, based on the total amount of the compound (the specific charge transport material and other charge transport materials) having the charge transport property in the composition that contains the specific charge transport material.

For the purposes of adjusting particle dispersibility and controlling viscosity, or for the purposes of adjusting the discharge gas resistance of the cured film (uppermost surface layer), mechanical strength, and damage resistance, reducing torque, controlling abrasion loss, and extending pot life, the composition containing the specific charge transport material (a) may be mixed with a polymer (c) unreactive with the specific charge transport material (a) or with a polymer (d) reactive with the specific charge transport material (a).

In the protective layer 5 (uppermost surface layer) that includes the cured film of the composition containing the specific charge transport material (a), the electrical characteristics and the mechanical strength are sufficiently secured. Accordingly, various polymers may be used as a binder resin. With the use of these polymers, the viscosity of the composition is improved, and the protective layer 5 (uppermost surface layer) having excellent surface properties is formed. Moreover, a gas-barrier property that prevents gas from being mixed into the uppermost surface layer is improved, and adhesiveness between the protective layer 5 and the underlayer may also be improved.

As the polymer (c) unreactive with the specific charge transport material (a), polymers that do not contain a radical-polymerizable unsaturated bond may be used, and examples of such polymers include known polymers such as a polycarbonate resin, a polyester resin, a polyarylate resin, a methacrylic resin, an acrylic resin, a polyvinyl chloride resin, a polyvinylidene chloride resin, and a polystyrene resin.

These polymers are used at 50% by mass or less, desirably at 40% by mass or less, and even more desirably at 30% by mass or less, based on the total amount of the compound (the specific charge transport material (a) and other charge transport materials) having a charge transport property in the composition containing the specific charge transport material (a).

As the polymer (d) reacting with the specific charge transport material (a), polymers that have radical-polymerizable unsaturated bond as a reactive group may be used, and examples of such polymers include polymers disclosed in Paragraphs [0026] to [0059] of JP-A-5-216249, Paragraphs [0027] to [0029] of JP-A-5-323630, Paragraphs [0089] to [0100] of JP-A-11-52603, Paragraphs [0107] to [0128] of JP-A-2000-264961, and the like, in addition to the polymers of acrylate or methacrylate described above.

For the purposes of adjusting film formability, flexibility, lubricity, adhesiveness, and the like, a coupling agent, a hard coating agent, and a fluorine-containing compound may be further added to the composition that contains the specific charge transport material (a). Specifically, as these additives, various silane coupling agents and commercially available silicone-based hard coating agents are used.

As the silane coupling agents, vinyl trichlorosilane, vinyl trimethoxysilane, vinyl triethoxysilane, γ-glycidoxypropyl methyl diethoxysilane, γ-glycidoxypropyl trimethoxysilane, γ-aminopropyl triethoxysilane, γ-aminopropyl trimethoxysilane, γ-aminopropyl methyl dimethoxysilane, N-β(aminoethyl) γ-aminopropyl triethoxysilane, tetramethoxysilane, methyl trimethoxysilane, dimethyl dimethoxysilane, and the like are used.

As the commercially available hard coating agent, KP-85, X-40-9740, and X-8239 (manufactured by ShinEtsu Silicones); AY42-440, AY42-441, and AY49-208 (manufactured by Dow Corning Toray); and the like are used.

In addition, in order to impart water repellency or the like, fluorine-containing compounds such as (tridecafluoro-1,1,2,2-tetrahydrooctyl)triethoxysilane, (3,3,3-trifluoropropyl)trimethoxysilane, 3-(heptafluoroisopropoxy)propyl triethoxysilane, 1H,1H,2H,2H-perfluoroalkyl triethoxysilane, 1H,1H,2H,2H-perfluorodecyl triethoxysilane, and 1H,1H, 2H,2H-perfluoroctyl triethoxysilane may also be added. Moreover, a reactive fluorine-containing compound and the like disclosed in JP-A-2001-166510 may be mixed in.

The silane coupling agent is used in an arbitrary amount, but the amount of the fluorine-containing compound is desirably 0.25 time or less of the compound not containing fluorine based on mass. If the amount used exceeds this amount, the formability of the crosslinked film becomes problematic in some cases.

For the purposes of adjusting the discharge gas resistance of the protective layer, mechanical strength, and damage resistance, reducing torque, controlling abrasion amount, and extending pot life, or for the purposes of adjusting particle dispersibility and controlling viscosity, a resin may be added to the protective layer (uppermost surface layer) 5.

For the purpose of preventing the deterioration of the protective layer caused by oxidizing gas such as ozone which is generated by a charger, it is desirable to add an antioxidant to the protective layer (uppermost surface layer) 5. If the mechanical strength of the photoreceptor surface increases, and the life of the photoreceptor is extended, the photoreceptor contacts the oxidizing gas for a long time. Accordingly, oxidation resistance stronger than that in the related art is required.

As the antioxidant, antioxidants based on hindered phenol or hindered amine are desirable, and known antioxidants such as an organic ion-based antioxidant, a phosphite-based antioxidant, a dithiocarbamic acid salt-based antioxidant, a thiourea-based antioxidant, and a benzimidazole-based antioxidant may also be used. The amount of the antioxidant added is desirably 20% by mass or less, and more desirably 10% by mass or less, based on the total solid contents in a coating liquid (composition) for forming the protective layer.

Examples of the hindered phenol-based antioxidant include "Irganox 1076", "Irganox 1010", "Irganox 1098", "Irganox 245", "Irganox 1330", "Irganox 3114", "3,5-di-t-butyl-4-hydroxybiphenyl", and the like.

Examples of the hindered amine-based antioxidant include "Sanol LS2626", "Sanol LS765", "Sanol LS770", "Sanol LS744", "Tinuvin 144", "Tinuvin622LD", "Mark LA57", "Mark LA67", "Mark LA62", "Mark LA68", and "Mark LA63"; examples of a thioether-based antioxidant include "Sumilizer TPS" and "Sumilizer TP-D"; and examples of the phosphite-based antioxidant include "Mark 2112", "Mark PEP-8", "Mark PEP-24G", "Mark PEP-36", "Mark 329K", "Mark HP-10", and the like.

For the purpose of reducing residual potential of the protective layer or improving the strength, various particles may be further added to the protective layer (uppermost surface layer) 5.

An example of the particles includes silicon-containing particles. The silicon-containing particles are particles containing silicon as a constituent element, and specific examples thereof include colloidal silica and silicone particles. The colloidal silica used as the silicon-containing particles is selected from those obtained by dispersing silica having an average particle size of from 1 nm to 100 nm and desirably of from 10 nm to 30 nm in an organic solvent such as an acidic or alkaline aqueous dispersion, an alcohol, a ketone, or an ester, and commercially available general colloidal silica may also be used.

The solid content of the colloidal silica in the protective layer 5 is not particularly limited. However, in view of film formability, electrical characteristics, and strength, the colloidal silica is used in a range of from 0.1% by mass to 50% by mass, and desirably in a range of from 0.1% by mass to 30% by mass, based on the total solid content of the protective layer 5.

The silicone particles used as the silicon-containing particles are selected from silicone resin particles, silicone rubber particles, and silica particles that are surface-treated with silicone, and commercially available general silicone particles are used as the silicone particles. These silicone particles are spherical, and the average particle size thereof is desirably from 1 nm to 500 nm, and more desirably from 10 nm to 100 nm. The silicone particles are small-size particles that are chemically inactive and have excellent dispersibility with a resin. Since the content of the silicone particles required for obtaining sufficient characteristics is small, the surface properties of the electrophotographic photoreceptor is improved without hindering a crosslinking reaction. That is, while these particles are incorporated in a strong crosslinked structure without variation, the lubricity and water repellency of the electrophotographic photoreceptor surface are improved, and excellent abrasion resistance and a contaminant-repelling property are maintained over a long time.

The content of the silicone particles in the protective layer 5 is desirably from 0.1% by mass to 30% by mass, and more desirably from 0.5% by mass to 10% by mass, based on the total solid contents of the protective layer 5.

Examples of other particles include fluorine-based particles such as tetrafluoroethylene, trifluoroethylene, hexafluoropropylene, vinyl fluoride, vinylidene fluoride; particles including a resin that is obtained by copolymerizing a fluororesin with a monomer having a hydroxyl group, as disclosed in "Proceedings of the 8$^{th}$ Polymer Material Forum, p. 89"; and semiconductive metallic oxides such as ZnO—$Al_2O_3$, $SnO_2$—$Sb_2O_3$, $In_2O_3$—$SnO_2$, $ZnO_2$—$TiO_2$, ZnO—$TiO_2$, MgO—$Al_2O_3$, FeO—$TiO_2$, $TiO_2$, $SnO_2$, $In_2O_3$, ZnO, and MgO.

The amount of other particles added is desirably from 0.1% by mass to 30% by mass, and more desirably from 0.5% by mass to 20% by mass, based on the total solid contents of the protective layer 5.

For the same purpose as described above, oil such as silicone oil may be added to the protective layer (uppermost surface layer) 5. Examples of the silicone oil include silicone oil such as dimethyl polysiloxane, diphenyl polysiloxane, or phenyl methyl siloxane; reactive silicone oil such as amino-modified polysiloxane, epoxy-modified polysiloxane, carboxyl-modified polysiloxane, carbinol-modified polysiloxane, methacryl-modified polysiloxane, mercapto-modified polysiloxane, or phenol-modified polysiloxane; cyclic dimethyl cyclosiloxanes such as hexamethyl cyclotrisiloxane, octamethyl cyclotetrasiloxane, decamethyl cyclopentasiloxane, and dodecamethyl cyclohexasiloxane; cyclic methylphenyl cyclosiloxanes such as 1,3,5-trimethyl-1,3,5-triphenyl cyclotrisiloxane, 1,3,5,7-tetramethyl-1,3,5,7-tetraphenyl cyclotetrasiloxane, and 1,3,5,7,9-pentamethyl-1,3,5,7,9-pentaphenyl cyclopentasiloxane; cyclic phenyl cyclosiloxanes such as hexaphenyl cyclotrisiloxane; fluorine-containing cyclosiloxanes such as (3,3,3-trifluoropropyl)methyl cyclotrisiloxane; hydrosilyl group-containing cyclosiloxanes such as a methyl hydrosiloxane mixture, pentamethyl cyclopentasiloxane, and phenyl hydrocyclosiloxane; vinyl group-containing cyclosiloxanes such as pentavinyl pentamethyl cyclopentasiloxane; and the like.

A metal, metallic oxide, carbon black, and the like may also be added to the protective layer (uppermost surface layer) 5. Examples of the metal include aluminum, zinc, copper, chromium, nickel, silver and stainless steel, or those obtained by vapor-depositing these metals onto the surface of plastic particles. Examples of the metallic oxide include zinc oxide, titanium oxide, tin oxide, antimony oxide, indium oxide, bismuth oxide, indium oxide doped with tin, tin oxide doped with antimony or tantalum, zirconium oxide doped with antimony, and the like. These metallic oxides may be used alone or in combination of two or more kinds thereof. When used in combination of two or more kinds thereof, the metallic oxide may be simply mixed, or may be used in the form of a solid solution or may be melted. The average particle size of the conductive particles is 0.3 μm or less, and particularly desirably 0.1 μm or less, in view of the transparency of the protective layer.

The composition containing the specific charge transport material (a), which is used for forming the protective layer 5, is desirably prepared as a coating liquid for forming a protective layer.

The coating liquid for forming a protective layer may be free of a solvent. If necessary, the coating liquid may be prepared using a single solvent or mixed solvent of solvents based on an aromatic compound such as toluene or xylene; ketones such as methyl ethyl ketone, methyl isobutyl ketone, or cyclohexanone; esters such as ethyl acetate or butyl acetate; ethers such as tetrahydrofuran or dioxane; cellosolve such as ethylene glycol monomethyl ether; and alcohols such as isopropyl alcohol or butanol; and the like.

When the coating liquid is obtained by reacting the components described above, the respective components may be simply mixed or dissolved. However, the components may be heated in a condition of desirably at from room temperature to 100° C., and more desirably at from 30° C. to 80° C., desirably for from 10 minutes to 100 hours, and more desirably for from 1 hour to 50 hours. At this time, it is also desirable to irradiate the components with ultrasonic waves.

In this manner, a partial reaction may proceed in the coating liquid, and the uniformity of the coating liquid is improved, whereby a uniform film that does not exhibit coating film defects is easily obtained.

The coating liquid for forming a protective layer that includes the composition containing the specific charge transport material (a) is coated on the charge transporting layer 3 forming the surface to be coated, by general methods such as blade coating, wire bar coating, spray coating, dip coating, bead coating, air knife coating, and curtain coating.

Thereafter, the obtained coating film is polymerized and cured with light, electron beams, heat, and the like.

Herein, when the coating film is polymerized and cured with light, a known light source such as a mercury lamp, a metal halide, or the like is used.

In addition, when the coating film is polymerized and cured with heat, the heating condition is desirably at 50° C. or higher. If the temperature is equal to or lower than this, the life of the cured film is likely to be shortened. Particularly, the heating temperature is desirably from 100° C. to 170° C., in respect of the reaction rate, strength, and electrical characteristics of the prepared photoreceptor.

When the coating film is polymerized and cured with electron beams, an electron beam emitting device is used. Moreover, to speed up the reaction, heating may be performed together.

During the polymerization and curing reaction described above, in order to conduct a chain reaction without deactivating radicals generated by the light, electron beams, and heat, the reaction is performed in a vacuum or inert gas atmosphere with an oxygen level as low as desirably 10% or less, more desirably 5% or less, even more desirably 2% or less, and most desirably 500 ppm or less.

In the exemplary embodiment, as described above, a method of causing radical polymerization by heating, irradiating light, electron beams, and the like is used as the curing method of the coating film. However, if the reaction proceeds too rapidly, the structure of the coating film is not easily relaxed due to crosslinking, and variations and wrinkles are easily caused in the film. Therefore, it is desirable to use thermal curing in which the radical is generated relatively slowly. Particularly, the specific charge transport material (a) has a styryl methylene group, and if the styryl methylene group is combined with the thermal curing, the structural relaxation of the coating film is promoted, and the protective layer 5 (uppermost surface layer) that has excellent surface properties and high uniformity is obtained.

On the other hand, when the coating film is cured with light or electron beams, the reaction rate is high. Therefore, the molecular movement is easily frozen in a short time, and functional groups easily remain. In addition, since the crosslinking reaction is caused before the structural relaxation occurs, a film having great residual strain is obtained, and the film is prone to have insufficient surface coating film uniformity and internal compositional uniformity.

So far, an example of the functional separation type photosensitive layer has been described with reference to the electrophotographic photoreceptor 7A shown in FIG. 1. However, in the case of the single layer type photosensitive layer 6 (charge generating/charge transporting layer) of the electrophotographic photoreceptor 7C shown in FIG. 3, the following embodiment is desirable.

That is, the content of the charge generating material in the single layer type photosensitive layer 6 is from 10% by mass to 85% by mass, and desirably from 20% by mass to 50% by mass. In addition, the content of the charge transport material is desirably from 5% by mass to 50% by mass. The method of forming the single layer type photosensitive layer 6 (charge generating/charge transporting layer) is the same as that of the charge generating layer 2 or charge transporting layer 3. The film thickness of the single layer type photosensitive layer (charge generating/charge transporting layer) 6 is desirably from 5 μm to 50 μm, and more desirably from 10 μm to 40 μm.

In the exemplary embodiment described above, an embodiment was described in which the uppermost surface layer including the cured film of the composition that contains the specific charge transport material (a) is the protective layer 5. However, if the layers are configured without the protective layer 5, the charge transporting layer positioned at the uppermost surface in the layer configuration becomes the uppermost surface layer.

When the uppermost surface layer is the charge transporting layer, the thickness of this layer is desirably from 7 μm to 60 μm, and more desirably from 8 μm to 55 μm.

<Conductive Substrate)

Examples of the conductive substrate 4 include a metal plate, a metal drum, and a metal belt configured with metals such as aluminum, copper, zinc, stainless steel, chromium, nickel, molybdenum, vanadium, indium, gold, and platinum, or an alloy thereof. Examples of the conductive substrate 4 also include paper, plastic film, belt and the like onto which a conductive compound such as a conductive polymer or indium oxide, a metal such as aluminum, palladium, or gold or an alloy thereof is coated, vapor-deposited, or laminated.

Herein, the word "conductive" means that volume resistivity is less than $10^{13}$ Ωcm.

When the electrophotographic photoreceptor 7A is used for a laser printer, in order to prevent interference fringes caused when laser beams are emitted, the surface of the conductive substrate 4 is desirably made into a rough surface having a center line average roughness Ra of from 0.04 µm to 0.5 µm. If Ra is less than 0.04 µm, an interference-preventing effect tends to be insufficient since the surface almost becomes a mirror surface, and if Ra exceeds 0.5 µm, image quality tends to be dull even if a coat is formed. In addition, when non-interference light is used as a light source, it is not particularly necessary to roughen the surface to prevent the interference fringes, and defects caused by the unevenness on the surface of the conductive substrate 4 are prevented. Therefore, the use of the non-interference light is suitable for further extending the life of the photoreceptor.

As a method of roughening the surface, wet honing in which an abrading agent is suspended in water and sprayed onto a supporter, centerless grinding in which grinding is continuously performed while a supporter is pressed on a spinning grindstone, anodization, or the like is desirable.

As another method of roughening the surface, a method is also desirably used in which conductive or semi-conductive powder is dispersed in a resin so as to form a layer on the surface of a supporter, and the surface is roughened using the particles dispersed in the layer, without roughening the surface of the conductive substrate 4.

Herein, in the surface roughening performed by anodization, anodization is conducted in an electrolyte solution by using aluminum as an anode, thereby forming an oxide film on the surface of aluminum. Examples of the electrolyte solution include a sulfuric acid solution, an oxalic acid solution, and the like. However, since the porous anodized oxide film formed by anodization is chemically active as it is, this film is easily contaminated, and shows great fluctuation in resistance depending on environment. Therefore, it is desirable to perform sealing in which the fine porous of the anodized oxide film is blocked by volume expansion caused by a hydration reaction in steam under pressure or in boiling water (a metal salt such as nickel may be added), thereby changing the film into a more stabilized hydrated oxide.

The thickness of the anodized oxide film is desirably from 0.3 µm to 15 µm. If the film thickness is less than 0.3 µm, barrier properties against injection tend to be lacked, and the effects tend to be insufficient. On the other hand, when the film thickness exceeds 15 µm, the increase in residual potential resulting from repeated use tends to be caused.

The conductive substrate 4 may also be treated with an aqueous acidic solution or boehmite. The treatment using an acidic treatment liquid containing phosphoric acid, chromic acid, and hydrofluoric acid is performed in the following manner. First, the acidic treatment liquid is prepared. As a mixing ratio between the phosphoric acid, chromic acid, and hydrofluoric acid in the acidic treatment liquid, the phosphoric acid is in a range of from 10% by mass to 11% by mass, the chromic acid is in a range of from 3% by mass to 5% by mass, and the hydrofluoric acid is in a range of from 0.5% by mass to 2% by mass. The concentration of all these acids is desirably from 13.5% by mass to 18% by mass. The treatment temperature is desirably from 42° C. to 48° C., but if the treatment temperature is kept high, a thicker coat is formed more rapidly, compared to a case where the treatment temperature is lower than the above range. The film thickness of the coat is desirably from 0.3 µm to 15 µm. If the film thickness is less than 0.3 µm, barrier properties against injection tend to be lacked, and the effects tend to be insufficient. On the other hand, when the film thickness exceeds 15 µm, the increase in residual potential resulting from repeated use tends to be caused.

In the boehmite treatment, the conductive substrate 4 is dipped in ultrapure water at from 90° C. to 100° C. for from 5 minutes to 60 minutes, or brought into contact with heated steam at from 90° C. to 120° C. for from 5 minutes to 60 minutes. The film thickness of the coat is desirably from 0.1 µm to 5 µm. The obtained resultant may be anodized using an electrolyte solution having low coat solubility compared to other electrolytes, such as adipic acid, boric acid, a boric acid salt, a phosphoric acid salt, a phthalic acid salt, a maleic acid salt, a benzoic acid salt, a tartaric acid salt, and a citric acid salt.

<Undercoat Layer>

The undercoat layer 1 is configured by containing inorganic particles in a binder resin, for example.

As the inorganic particles, particles having volume resistance (volume resistivity) of from $10^2$ Ω·cm to $10^{11}$ Ω·cm are desirably used. This is because the undercoat layer 1 needs to obtain resistance suitable for acquiring leak resistance and a carrier blocking property. If the resistance value of the inorganic particles is lower than the lower limit of the above range, there is a concern that sufficient leak resistance will not be obtained, and if the resistance value is higher than the upper limit of the range, there is a concern that the residual potential will increase.

Among the inorganic particles, as the inorganic particles having the resistance value described above, in organic particles (conductive metallic oxide) of tin oxide, titanium oxide, zinc oxide, zirconium oxide, and the like are desirably used, and particularly, zinc oxide is desirably used.

The inorganic particles may also be surface-treated, and two or more kinds of particles such as particles differing in types of the surface treatment or particles differing in the particle size may be used as a mixture.

The volume average particle size of the inorganic particles is desirably in a range of from 50 nm to 2000 nm (desirably from 60 nm to 1000 nm).

In addition, as the inorganic particles, particles having a specific surface area of 10 $m^2/g$ or more measured by a BET method are desirably used. The particles having a specific surface area less than 10 $m^2/g$ easily result in deterioration in chargeability, and excellent electrophotographic characteristics tend not to be easily obtained.

If the undercoat layer further contains an acceptor compound together with the inorganic particles, an undercoat layer that is excellent in long-term stability of the electrical characteristics and the carrier blocking property is obtained.

As the acceptor compound, any compound may be used as long as desired characteristics are obtained from the compound, but charge transporting substances including a quinone-based compound such as chloranil or bromanil; a tetracyanoquinodimethane-based compound; a fluorenone compound such as 2,4,7-trinitrofluorenone or 2,4,5,7-tetranitro-9-fluorenone; an oxadiazole-based compound such as 2-(4-biphenyl)-5-(4-t-butylphenyl)-1,3,4-oxadiazole, 2,5-bis(4-naphthyl)-1,3,4-oxadiazole, or 2,5-bis(4-diethylaminophenyl)1,3,4-oxadiazole; a xanthone-based compound; a thiophene compound; and a diphenoquinone compound such as 3,3',5,5'-tetra-t-butyl diphenoquinone are desirable. Particularly, compounds having an anthraquinone structure are desirable. In addition, acceptor compounds having an anthraquinone structure such as a hydroxyanthraquinone-based compound, an aminoanthraquinone-based compound, and an aminohydroxyanthraquinone-based compound are desirably used, and specific examples thereof include anthraquinone, alizarin, quinizarin, anthrarufin, purpurin, and a derivative thereof.

The content of these acceptor compounds may be arbitrarily set as long as the content is in a range in which desired characteristics are obtained, but desirably, the acceptor compound is contained in a range of from 0.01% by mass to 20% by mass, based on the inorganic particles. In addition, in view of preventing charge accumulation and aggregation of the inorganic particles, the acceptor compound is desirably contained at from 0.05% by mass to 10% by mass, based on the inorganic particles. The aggregation of the inorganic particles has a tendency to cause not only variations in forming a conduction path and the aggravation of a maintenance property such as increase in residual potential in repeated use, but also image defects such as black dots.

The acceptor compound may be simply added to a coating liquid for forming an undercoat layer, or may be attached onto the surface of the inorganic particles in advance.

Examples of a method of attaching the acceptor compound onto the surface of the inorganic particles include a dry method or a wet method.

When the surface treatment is performed by the dry method, while the inorganic particles are stirred with a mixer or the like having a strong shearing force, the acceptor compound is added dropwise thereto as it is or after dissolved in an organic solvent, and the resultant is sprayed together with dry air or nitrogen gas, whereby the surface is treated while suppressing variations. The addition or spraying is performed desirably at a temperature equal to or lower than the boiling point of the solvent. If spraying is performed at a temperature equal to or higher than the boiling point of the solvent, there is a defect that the solvent evaporates before being stirred for preventing occurrence of variation, and the acceptor compound is locally solidified. Consequently, it is difficult to perform the treatment without variation, which is thus not desirable. After the addition or spraying, baking may be performed at 100° C. or a higher temperature. The baking is performed in an arbitrary range of temperature and time, so long as desired electrophotographic characteristics are obtained in the range.

As the wet method, the inorganic particles are dispersed in a solvent by stirring, ultrasonic waves, a sand mill, an attritor, a ball mill, or the like, and the acceptor compound is added thereto. Subsequently, the resultant is stirred or dispersed, and then the solvent is removed, whereby the surface is treated without variations. As a method of removing the solvent, the solvent is removed by filtering or distillation. After the solvent is removed, baking may be performed at 100° C. or a higher temperature. The baking is performed in an arbitrary range of temperature and time, so long as desired electrophotographic characteristics are obtained in the range. In the wet method, inorganic particles-containing moisture is removed before a surface treatment agent is added, and for example, a method of removing the moisture while stirring and heating the moisture in the solvent used for the surface treatment, or a method of removing the moisture by causing azeotropy of the solvent and moisture may be used.

The inorganic particles may be surface-treated before the acceptor compound is imparted. As the surface treatment agent, any agent may be used as long as desired characteristics are obtained by the agent, and such agent is selected from known materials. Examples of the surface treatment agent include a silane coupling agent, a titanate-based coupling agent, an aluminum-based coupling agent, a surfactant, and the like. Particularly, a silane coupling agent is desirably used since excellent electrical characteristics are obtained by this agent. Moreover, a silane coupling having an amino group is desirably used since this agent provides the excellent blocking property to the undercoat layer 1.

As the silane coupling agent having an amino group, any agent may be used so long as desired electrical characteristics are obtained by the agent. Specific examples thereof include γ-aminopropyl triethoxysilane, N-β-(aminoethyl)-γ-aminopropyl trimethoxysilane, N-β-(aminoethyl)-γ-aminopropylmethyl dimethoxysilane, N,N-bis(β-hydroxyethyl)-γ-aminopropyl triethoxysilane, and the like, but the agent is not limited thereto.

The silane coupling agent may be used as a mixture of two or more kinds thereof. Examples of the silane coupling agent that may be used concurrently with the silane coupling agent having an amino group include vinyl trimethoxysilane, γ-methacryloxypropyl-tris(β-methoxyethoxy)silane, β-(3,4-epoxycyclohexyl)ethyl trimethoxysilane, γ-glycidoxypropyl trimethoxysilane, vinyl triacetoxysilane, γ-mercaptopropyl trimethoxysilane, γ-aminopropyl triethoxysilane, N-β-(aminoethyl)-γ-aminopropyl trimethoxysilane, N-β-(aminoethyl)-γ-aminopropylmethyl dimethoxysilane, N,N-bis(β-hydroxyethyl)-γ-aminopropyl triethoxysilane, γ-chloropropyl trimethoxysilane, and the like, but the silane coupling agent is not limited thereto.

Any method may be used as the surface treatment method using those surface treatment agents as long as the method is a known method, but it is desirable to use the dry method or wet method. Moreover, imparting the acceptor compound and surface treatment performed using the surface treatment agent such as a silane coupling agent may be conducted at the same time.

The amount of the silane coupling agent based on the inorganic particles in the undercoat layer 1 may be arbitrarily set so long as desired electrophotographic characteristics are obtained in the amount. However, the amount is desirably from 0.5% by mass to 10% by mass based on the inorganic particles, in view of the improvement of the dispersibility.

The undercoat layer 1 may further contain a binder resin.

As the binder resin contained in the undercoat layer 1, any known resin may be used as long as an excellent film is formed, and desired characteristics are obtained by the binder resin. For example, known polymeric resin compounds such as an acetal resin including polyvinyl butyral, a polyvinyl alcohol resin, casein, a polyamide resin, a cellulose resin, gelatin, a polyurethane resin, a polyester resin, a methacrylic resin, an acrylic resin, a polyvinyl chloride resin, a polyvinyl acetate resin, a vinyl chloride-vinyl acetate-maleic anhydride resin, a silicone resin, silicone-alkyd resin, a phenol resin, a phenol-formaldehyde resin, a melamine resin, and a urethane resin, a charge transporting resin having a charge transporting group, a conductive resin such as polyaniline, and the like are used. Among these, a resin insoluble in a coating solvent of the upper layer is desirably used, and particularly, a phenol resin, a phenol-formaldehyde resin, a melamine resin, and a urethane resin, an epoxy resin, and the like are desirably used. When these resins are used in combination of two or more kinds thereof, the mixing ratio is set according to necessity.

The proportion between the inorganic particles (metallic oxide to which an acceptor property has been imparted) in which the acceptor compound has been imparted to the particle surface and the binder resin, or between the inorganic particles and the binder resin in the coating liquid for forming an undercoat layer is arbitrarily set within a range in which the desired characteristics of the electrophotographic photoreceptor are obtained.

Various additives may be added to the undercoat layer 1 to improve electrical characteristics, environmental stability, and image quality.

As the additives, known materials such as a polycyclic condensed type or azo-based electron transporting pigment, a zirconium chelate compound, a titanium chelate compound, an aluminum chelate compound, a titanium alkoxide compound, an organic titanium compound, a silane coupling agent are used. Though used for surface treatment of the inorganic particles as described above, the silane coupling agent may also be further added to the coating liquid for forming an undercoat layer as an additive.

Specific examples of the silane coupling agent as an additive include vinyl trimethoxysilane, γ-methacryloxypropyl-tris(β-methoxyethoxy)silane, β-(3,4-epoxycyclohexyl)ethyl trimethoxysilane, γ-glycidoxypropyl trimethoxysilane, vinyl triacetoxysilane, γ-mercaptopropyl trimethoxysilane, γ-aminopropyl triethoxysilane, N-β-(aminoethyl)-γ-aminopropyl trimethoxysilane, N-β-(aminoethyl)-γ-aminopropylmethyl dimethoxysilane, N,N-bis(β-hydroxyethyl)-γ-aminopropyl triethoxysilane, γ-chloropropyl trimethoxysilane, and the like.

Examples of the zirconium chelate compound include zirconium butoxide, zirconium acetoethyl acetate, zirconium triethanolamine, acetylacetonate zirconium butoxide, acetoethyl acetate zirconium butoxide, zirconium acetate, zirconium oxalate, zirconium lactate, zirconium phosphonate, zirconium octanoate, zirconium naphthenate, zirconium laurate, zirconium stearate, zirconium isostearate, methacrylate zirconium butoxide, stearate zirconium butoxide, isostearate zirconium butoxide, and the like.

Examples of the titanium chelate compound include tetraisopropyl titanate, tetra-n-butyl titanate, a butyl titanate dimer, tetra(2-ethylhexyl)titanate, titanium acetylacetonate, polytitanium acetylacetonate, titanium octyleneglycolate, a titanium lactate ammonium salt, titanium lactate, titanium lactate ethyl ester, titanium ethanol aminate, polyhydroxy titanium stearate, and the like.

Examples of the aluminum chelate compound include aluminum isopropylate, monobutoxyaluminum diisopropylate, aluminum butyrate, ethyl acetoacetate aluminum diisopropylate, aluminum tris(ethylacetoacetate), and the like.

These compounds may be used alone, or as a mixture or a polycondensate of plural compounds.

The solvent for preparing the coating liquid for forming an undercoat layer is arbitrarily selected from known organic solvents based on, for example, alcohols, aromatic compounds, halogenated hydrocarbons, ketones, ketone alcohols, ethers, esters, and the like.

Specifically, as the solvent, general organic solvents such as methanol, ethanol, n-propanol, iso-propanol, n-butanol, benzyl alcohol, methyl cellosolve, ethyl cellosolve, acetone, methyl ethyl ketone, cyclohexanone, methyl acetate, ethyl acetate, n-butyl acetate, dioxane, tetrahydrofuran, methylene chloride, chloroform, chlorobenzene, and toluene are used, for example.

These solvents may be used alone or as a mixture of two or more kinds thereof. When the solvents are mixed, any solvent may be used as long as the solvent is able to dissolve the binder resin as a mixed solvent.

As the method of dispersing the inorganic particles in preparing the coating liquid for forming an undercoat layer, known methods such as methods using a roll mill, a ball mill, a vibration ball mill, an attritor, a sand mill, a colloid mill, or a paint shaker are used, As the coating method used for providing the undercoat layer 1, a general method such as blade coating, wire bar coating, spray coating, dip coating, bead coating, air knife coating, or curtain coating is used.

By using the coating liquid for forming an undercoat layer obtained in this manner, the undercoat layer 1 is formed on the conductive substrate.

The undercoat layer 1 desirably has a Vickers' hardness of 35 or more.

The thickness of the undercoat layer 1 is arbitrarily set as long as the desired characteristics are obtained in the thickness, but the thickness is desirably 15 μm or more, and more desirably from 15 μm to 50 μm.

When the thickness of the undercoat layer 1 is less than 15 μm, sufficient leak resistance is not obtained in some cases. If the thickness is equal to or greater than 50 μm, the residual potential easily remains in a case of long-term use, so image density abnormality is easily caused.

In order to prevent a moire image, the surface roughness (ten-point average roughness) of the undercoat layer 1 is adjusted to from ¼ n (n is a refractive index of the upper layer) to ½λ of a wavelength λ of a laser used for exposure.

For the purpose of adjusting the surface roughness, particles of a resin or the like may be added to the undercoat layer. As the resin particles, silicone resin particles, crosslinked methyl polymethacrylic resin particles, and the like are used.

Moreover, the surface of the undercoat layer may be polished to adjust the surface roughness.

As the polishing method, buffing, sand blasting, wet honing, grinding, and the like are used.

By drying the coating liquid for forming an undercoat layer described above that has been coated onto the conductive substrate 4, the undercoat layer 1 is obtained. The drying is generally performed at a temperature at which a film is formed by the evaporation of the solvent.

<Charge Generating Layer>

The charge generating layer 2 contains the charge generating material and the binder resin.

Examples of the charge generating material include an azo pigment such as bisazo or trisazo, a condensed cyclic aromatic pigment such as dibromoanthanthrone, a perylene pigment, a pyrrolopyrrole pigment, a phthalocyanine pigment, zinc oxide, trigonal selenium, and the like. Among these, in order to respond to laser exposure of a near-infrared region, metallic and non-metallic phthalocyanine pigments are desirably used as the charge generating material. Particularly, hydroxy gallium phthalocyanine disclosed in JP-A-5-263007 and JP-A-5-279591, chlorogallium phthalocyanine disclosed JP-A-5-98181, dichlorotin phthalocyanine disclosed in JP-A-5-140472 and JP-A-5-140473, and titanyl phthalocyanine disclosed in JP-A-4-189873 are more desirable. In addition, in order to respond to the laser exposure of a near-ultraviolet region, a condensed cyclic aromatic pigment such as dibromoanthanthrone, a thioindigo-based pigment, a porphyrazine compound, zinc oxide, trigonal selenium, bisazo pigments disclosed in JP-A-2004-78147 and JP-A-2005-181992, and the like are more desirably used as the charge generating material.

The binder resin used for the charge generating layer 2 is selected from a wide range of insulating resins. Moreover, the binder resin may be selected from organic photoconductive polymers such as poly-N-vinylcarbazole, polyvinylanthracene, polyvinylpyrene, and polysilane. Examples of desirable binder resins include a polyvinyl butyral resin, a polyarylate resin (a polycondensate of bisphenols and aromatic divalent carboxylic acid or the like), a polycarbonate resin, a polyester resin, a phenoxy resin, a vinyl chloride-vinyl acetate copolymer, a polyamide resin, an acrylic resin, a polyacrylamide resin, a polyvinyl pyridine resin, a cellulose resin, a urethane resin, an epoxy resin, casein, a polyvinyl alcohol resin, a polyvinyl pyrrolidone resin, and the like. These binder resins may be used alone or as a mixture of two or more kinds thereof. The mixing ratio between the charge generating material and the binder resin is desirably in a range of from 10:1 to 1:10, in terms of a mass ratio. Herein, the word "insulating" means that the volume resistivity is $10^{13}$ Ωcm or greater.

The charge generating layer 2 is formed using the coating liquid for forming a charge generating layer obtained by dispersing the charge generating material and the binder resin in a solvent.

Examples of the solvent used for the dispersion include methanol, ethanol, n-propanol, n-butanol, benzyl alcohol, methyl cellosolve, ethyl cellosolve, acetone, methyl ethyl ketone, cyclohexanone, methyl acetate, n-butyl acetate, dioxanone, tetrahydrofuran, methylene chloride, chloroform, chlorobenzene, toluene, and the like. These solvents may be used alone or as a mixture of two or more kinds thereof.

As the method of dispersing the charge generating material and the binder resin in a solvent, general methods such as a ball mill dispersing, attritor dispersing, sand mill dispersing, and the like are used. By these dispersing methods, the change of the charge generating material into a crystalline type caused by the dispersion is prevented.

During the dispersion, it is effective to adjust the average particle size of the charge generating material to 0.5 µm or less, desirably 0.3 µm or less, and more desirably 0.15 µm or less.

In forming the charge generating layer 2, general methods such as blade coating, wire bar coating, spray coating, dip coating, bead coating, air knife coating, and curtain coating are used.

The film thickness of the charge generating layer 2 obtained in this manner is desirably from 0.1 µm to 5.0 µm, and more desirably from 0.2 µm to 2.0 µm.

<Charge Transporting Layer>

The charge transporting layer 3 is formed by containing the charge transport material and the binder resin, or containing a polymeric charge transport material.

Examples of the charge transport material include an electron transporting compound including quinone-based compounds such as p-benzoquinone, chloranil, bromanil and anthraquinone, a tetracyanoquinodimethane-based compound, a fluorenone compound such as 2,4,7-trinitrofluorenone, a xanthone-based compound, a benzophenone-based compound, a cyanovinyl-based compound, and an ethylene-based compound; and hole-transporting compounds such as a triarylamine-based compound, a benzidine-based compound, an arylalkane-based compound, an aryl-substituted ethylene-based compound, a stilbene-based compound, an anthracene-based compound, and a hydrazone-based compound. These charge transport materials may be used alone or as a mixture of two or more kinds thereof, but are not limited to above materials.

As the charge transport material, a triarylamine derivative represented by the following Structural Formula (a-1), and a benzidine derivative represented by the following Structural Formula (a-2) are desirable, in view of the charge mobility.

(a-1)

In Structural Formula (a-1), each of $Ar^6$, $Ar^7$, and $Ar^8$ independently represents a substituted or unsubstituted aryl group, $-C_6H_4-C)(R^{10})=C(R^{11})(R^{12})$ or $-C_6H_4-CH=CH-CH=C(R^{13})(R^{14})$; and each of $R^{10}$ to $R^{14}$ independently represents a hydrogen atom, a substituted or unsubstituted alkyl group, or a substituted or unsubstituted aryl group.

Herein, examples of a substituent of each group described above include a halogen atom, an alkyl group having from 1 to 5 carbon atoms, an alkoxy group having from 1 to 5 carbon atoms, or a substituted amino group substituted with an alkyl group having from 1 to 3 carbon atoms.

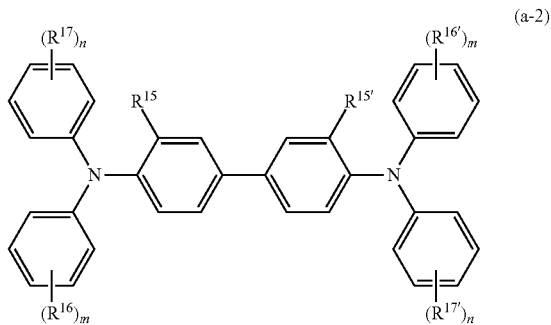
(a-2)

In Structural Formula (a-2), each of $R^{15}$ and $R^{15'}$ independently represents a hydrogen atom, a halogen atom, an alkyl group having from 1 to 5 carbon atoms, or an alkoxy group having from 1 to 5 carbon atoms. Each of $R^{16}$, $R^{16'}$, $R^{17}$, and $R^{17'}$ independently represents a hydrogen atom, a halogen atom, an alkyl group having from 1 to 5 carbon atoms, an alkoxy group having from 1 to 5 carbon atoms, an amino group substituted with an alkyl group having from 1 to 2 carbon atoms, a substituted or unsubstituted aryl group, $-C(R^{18})=C(R^{19})(R^{20})$, or $-CH=CH-CH=C(R^{21})(R^{22})$; and each of $R^{18}$ to $R^{22}$ independently represents a hydrogen atom, a substituted or unsubstituted alkyl group or a substituted or unsubstituted aryl group. Each of m and n independently represents an integer of from 0 to 2.

Herein, among the triarylamine derivative represented by Structural Formula (a-1) and the benzidine derivative represented by Structural Formula (a-2), a triarylamine derivative having "$-C_6H_4-CH=CH-CH=C(R^{13})(R^{14})$" and a benzidine derivative having "$-CH=CH-CH=C(R^{21})(R^{22})$" are particularly desirable since these derivatives are excellent in terms of charge mobility, adhesiveness with respect to the protective layer, a ghost image (hereinafter, referred to as a "ghost" in some cases) which is created since the history of the prior image is left, and the like.

Examples of the binder resin used for the charge transporting layer 3 include a polycarbonate resin, a polyester resin, a polyarylate resin, a methacrylic resin, an acrylic resin, a polyvinyl chloride resin, a polyvinylidene chloride resin, a polystyrene resin, a polyvinyl acetate resin, a styrene-butadiene copolymer, a vinylidene chloride-acrylonitrile copolymer, a vinyl chloride-vinyl acetate copolymer, a vinyl chloride-vinyl acetate-maleic anhydride copolymer, a silicone resin, a silicone-alkyd resin, a phenol-formaldehyde resin, a styrene-alkyd resin, a poly-N-vinyl carbozole, polysilane, and the like. Among these, the polycarbonate resin and the polyarylate resin are desirable since these resins are excellent in the charge transport property and the compatibility with the charge transport material.

These resins are used alone or as a mixture of two or more kinds thereof. The mixing ratio between the charge transport material and the binder resin is desirably from 10:1 to 1:5 in terms of a mass ratio.

Particularly, on the charge transporting layer 3, the protective layer (uppermost surface layer) including the cured film of the composition that contains the specific charge transport material (a) is provided. Accordingly, the viscosity average molecular weight of the binder resin used for the charge transporting layer 3 is desirably 40000 or more, more desirably 50000 or more, and even more desirably 55000 or more. If the binder resin having such a molecular weight is used for the charge transporting layer adjacent to the protective layer, adhesiveness, cracking resistance in forming the protective layer (uppermost surface layer), and the like become excellent, which is thus desirable.

The upper limit of the viscosity average molecular weight of the binder resin used for the charge transporting layer 3 is desirably 100000, in view of the uniformity (liquid dripping) of the coating film.

Herein, the viscosity average molecular weight of the binder resin in the exemplary embodiment is a value that is measured by a capillary viscometer.

In addition, for the same reason as described above, when the uppermost surface layer is the charge transporting layer, the viscosity average molecular weight of the binder resin included in the layer below the charge transporting layer is desirably in the above-described range.

A polymeric charge transport material may be used as the charge transport material. As the polymeric charge transport material, known materials having the charge transport property such as poly-N-vinylcarbozole, polysilane, and the like are used. Particularly, the polyester-based polymeric charge transport material disclosed in JP-A-8-176293 and JP-A-8-208820 is particularly desirable since this material has a higher charge transport property compared to other materials. The polymeric charge transport material may become a film as it is, but it may be mixed with the binder resin to form a film.

The charge transporting layer 3 is formed using a coating liquid for forming a charge transporting layer that contains the above-described constituent materials.

As the solvent used for the coating liquid for forming a charge transporting layer, general organic solvents including aromatic hydrocarbons such as benzene, toluene, xylene, and chlorobenzene; ketones such as acetone and 2-butanone; halogenated aliphatic hydrocarbons such as methylene chloride, chloroform, and ethylene chloride; and cyclic or linear ethers such as tetrahydrofuran and ethyl ether are used alone or as a mixture of two or more kinds thereof. As the method of dispersing the respective constituent materials, known methods are used.

As the method of coating the coating liquid for forming a charge transporting layer onto the charge generating layer 2, general methods such as blade coating, wire bar coating, spray coating, dip coating, bead coating, air knife coating, and curtain coating are used.

The film thickness of the charge transporting layer 3 is desirably from 5 μm to 50 μm, and more desirably from 10 μm to 30 μm.

[Image Forming Apparatus/Process Cartridge]

Figure 4:
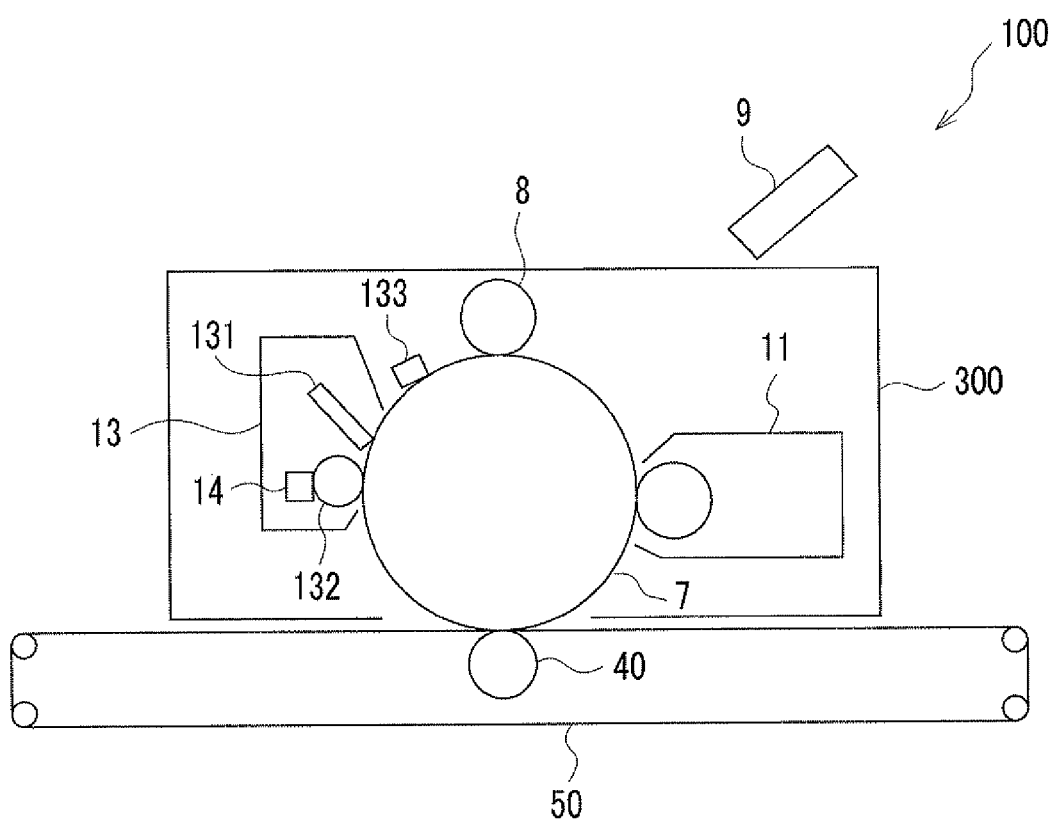
FIG. 4 is a schematic configuration view showing an image forming apparatus according to the exemplary embodiment.

FIG. 4 is a schematic configuration view showing an image forming apparatus 100 according to a first exemplary embodiment.

The image forming apparatus 100 shown in FIG. 4 includes a process cartridge 300 provided with an electrophotographic photoreceptor 7, an exposure device (electrostatic latent image forming unit) 9, a transfer device (transfer unit) 40, and an intermediate transfer member 50. In the image forming apparatus 100, the exposure device 9 is disposed in a position for exposing the electrophotographic photoreceptor 7 through an opening portion of the process cartridge 300, the transfer device 40 is disposed in a position where the transfer device 40 faces the electrophotographic photoreceptor 7 across the intermediate transfer member 50, and the intermediate transfer member 50 is disposed while a portion thereof is in contact with the electrophotographic photoreceptor 7.

The process cartridge 300 in FIG. 4 integrally supports the electrophotographic photoreceptor 7, a charger (charging unit) 8, a developing device (developing unit) 11, and a cleaning device 13 inside a housing. The cleaning device 13 includes a cleaning blade (cleaning member), and a cleaning blade 131 is disposed so as to contact the surface of the electrophotographic photoreceptor 7. The cleaning member is not limited to the embodiment of cleaning blade 131. The cleaning member may be a conductive or insulating fiber-like member, or this fibrous member may be used alone or used concurrently with a blade.

FIG. 4 shows an example that includes fibrous member 132 (roll shape) supplying a lubricant 14 to the surface of the photoreceptor 7 as the cleaning device 13, and uses a fibrous member 133 (flat brush shape) assisting cleaning, but these members are optionally used.

As the charger 8, for example, a contact type charger using a conductive or semiconductive charging roll, a charging brush, a charging film, a charging rubber blade, a charging tube, or the like is used. In addition, known chargers such as a non-contact type of roll charger, a scorotron charger using corona discharge, and a corotron charger may also be used.

Though not shown in the drawing, a photoreceptor heating member for increasing the temperature of the electrophotographic photoreceptor 7 and reducing a relative temperature is provided around the electrophotographic photoreceptor 7 so as to heighten the image stability.

Examples of the exposure device 9 include an optical system instrument or the like that exposes a desired image with light such as a semiconductor laser beam, LED light, or liquid crystal shutter light on the surface of the electrophotographic photoreceptor 7. As the wavelength of a light source, wavelengths in a spectrophotometric region of the photoreceptor are used. As the wavelength of the semiconductor laser, near infrared having an oscillation wavelength near 780 nm is used in most cases. However, the wavelength is not limited thereto, and lasers such as a laser having an oscillation wavelength of about 600 nm and a blue laser having an oscillation wavelength near 400 nm to 450 nm may also be used. In addition, in order to form color images, a surface-emitting type of laser beam source which realizes multi-beam output is also effective.

As the developing device 11, for example, a general developing device may be used which performs developing by bringing or not brining a magnetic or non-magnetic single-component or two-component developer or the like into contact with the photoreceptor. The developing device is not limited as long as it has the function described above, and is selected according to purposes. For example, a known developing device or the like is used which has a function of attaching the single-component or two-component developer to the photoreceptor 7 by using a brush, a roll, or the like. Among these, a developing device that uses a developing roll holding the developer on the surface thereof is desirable.

Hereinafter, a toner used for the developing device 11 will be described.

The average shape factor ($ML^2/A \times \pi/4 \times 100$, ML herein represents a maximum length of the toner particles, and A represents a projected area of the toner particles) of the toner is desirably from 100 to 150, and more desirably from 100 to 140. The volume average particle size of the toner is desirably from 2 µm to 12 µm, more desirably from 3 µm to 12 µm, and even more desirably from 3 µm to 9 µm. If the toner satisfying the above-described average shape factor and volume average particle size is used, images having a higher developing property, transfer property, and image quality are obtained, compared to other toners.

The toner is not particularly limited in terms of the production method, as long as the toner is within a range that satisfies the average shape factor and volume average particle size described above. For example, a toner is used which is produced by a kneading and pulverizing method that kneads, pulverizes, and classifies a mixture of a binder resin, a colorant, a release agent, and optionally a charge-controlling agent; a method that changes the shape of the particles obtained by the kneading and pulverizing method by using mechanical impact or heat energy; an emulsion polymerization aggregation method in which polymerizable monomers of a binder resin are emulsion-polymerized to form a dispersion, the dispersion is mixed with a dispersion of a colorant, a release agent, and optionally a charge-controlling agent or the like, followed by aggregation and heat melting, thereby obtaining toner particles; a suspension polymerization method in which polymerizable monomers for obtaining a binder resin, and a solution of a colorant, a release agent, and optionally a charge-controlling agent or the like are suspended in an aqueous solvent, followed by polymerization; a dissolution suspension method in which a binder resin, a colorant, a release agent, and optionally a solution of a charge-controlling agent are suspended in an aqueous solvent to produce particles; or the like.

In addition, a known method such as a method of forming a core shell structure by further attaching aggregated particles to the toner as a core obtained by the above-described method and performing heat melting may also be used. As the method of producing a toner, the suspension polymerization method producing a toner by using an aqueous solvent, the emulsion polymerization aggregation method, and the dissolution suspension method are desirable, and particularly, the emulsion polymerization aggregation method is desirable, in view of controlling shape and particle size distribution.

The toner base particles contain a binder resin, a colorant, and a release agent, and further contain silica or the charge-controlling agent if necessary.

Examples of the binder resin used for the toner base particles include homopolymers or copolymers of styrenes such as styrene and chlorostyrene; monoolefins such as ethylene, propylene, butylene, and isoprene; vinyl esters such as vinyl acetate, vinyl propionate, vinyl benzoate, and vinyl butyrate; α-methylene aliphatic monocarboxylic acid esters such as methyl acrylate, ethyl acrylate, butyl acrylate, dodecyl acrylate, octyl acrylate, phenyl acrylate, methyl methacrylate, ethyl methacrylate, butyl methacrylate, and dodecyl methacrylate; vinyl ethers such as vinyl methyl ether, vinyl ethyl ether, and vinyl butyl ether; vinyl ketones such as vinyl methyl ketone, vinyl hexyl ketone, and vinyl isopropenyl ketone; and polyester resins obtained by copolymerizing dicarboxylic acids with diols; and the like.

Particularly, examples of typical binder resins include polystyrene, a styrene-alkyl acrylate copolymer, a styrene-alkyl methacrylate copolymer, a styrene-acrylonitrile copolymer, a styrene-butadiene copolymer, a styrene-maleic anhydride copolymer, polyethylene, polypropylene, a polyester resin, and the like. The examples further include polyurethane, an epoxy resin, a silicone resin, polyimide, modified rosin, a paraffin wax, and the like.

Examples of typical colorants include magnetic powder of magnetite, ferrite, and the like, carbon black, aniline blue, calcoil blue, chrome yellow, ultramarine blue, DuPont oil red, quinoline yellow, methylene blue chloride, phthalocyanine blue, malachite green oxalate, lamp black, rose bengal, C. I. pigment red 48:1, C. I. pigment red 122, C. I. pigment red 57:1, C. I. pigment yellow 97, C. I. pigment yellow 17, C. I. pigment blue 15:1, C. I. pigment blue 15:3, and the like.

Examples of typical release agents include low-molecular weight polyethylene, low-molecular weight polypropylene, Fischer-Tropsch wax, montan wax, carnauba wax, rice wax, candelilla wax, and the like.

As the charge-controlling agent, known agents are used, and an azo-based metal complex compound, a metal complex compound of salicylic acid, and a resin type charge-controlling agent containing a polar group may be used. When the toner is produced by a wet production method, it is desirable to use a material that is not easily dissolved in water so as to control ionic strength and reduce waste water contamination. In addition, the toner may be either a magnetic toner containing a magnetic material or a non-magnetic toner not containing a magnetic material.

The toner used for the developing device 11 is produced by mixing the toner base particles with the external additives described above by using a Henschel mixer or a V blender. When the toner base particles are produced through a wet method, the particles may be externally added through the wet method.

Lubricant particles may be added to the toner used for the developing device 11. As the lubricant particles, solid lubricants such as graphite, molybdenum disulfide, talc, fatty acid, and a fatty acid metal salt; low-molecular weight polyolefins such as polypropylene, polyethylene, and polybutene; silicones having a softening point by heating; aliphatic amides such as oleic acid amide, erucic acid amide, ricinoleic acid amide, and stearic acid amide; plant waxes such as carnauba wax, rice wax, candelilla wax, Japanese wax, and jojoba oil; animal wax such as beeswax; mineral and petroleum waxes such as montan wax, ozokerite, ceresin, a paraffin wax, a micro-crystalline wax, and Fischer-Tropsch wax; and a modified product thereof are used. These may be used alone or in combination of two or more kinds thereof. Here, the volume average particle size thereof is desirably in a range of from 0.1 to 10 µm, and the uniform particle size may be obtained by pulverizing particles having the chemical structure described above. The amount of the lubricant particles added to the toner is desirably in a range of from 0.05% by mass to 2.0% by mass, and more desirably in a range of from 0.1% by mass to 1.5% by mass.

Inorganic particles, organic particles, complex particles which are obtained by attaching inorganic particles to the organic particles, and the like may be added to the toner used for the developing device 11, so as to remove extraneous substances or deteriorated substances on the surface of the electrophotographic photoreceptor, for example.

As the inorganic particles, various inorganic oxides, nitrides, and borides such as silica, alumina, titania, zirconia, barium titanate, aluminum titanate, strontium titanate, magnesium titanate, zinc oxide, chromium oxide, cerium oxide, antimony oxide, tungsten oxide, tin oxide, tellurium oxide, manganese oxide, boron oxide, silicon carbide, boron carbide, titanium carbide, silicon nitride, titanium nitride, and boron nitride are suitably used.

The inorganic particles may be treated with titanium coupling agents such as tetrabutyl titanate, tetraoctyl titanate, isopropyl triisostearoyl titanate, isopropyl tridecyl benzenesulfonyl titanate, and bis(dioctylpyrophosphate)oxyacetate titanate; and silane coupling agents such as γ-(2-aminoethyl) aminopropyl trimethoxysilane, γ-(2-aminoethyl)aminopropyl methyl dimethoxysilane, γ-methacryloxypropyl trimethoxysilane, an N-β-(N-vinylbenzylaminoethyl)γ-aminopropyl trimethoxysilane hydrochloric acid salt, hexamethyldisilazane, methyl trimethoxysilane, butyl trimethoxysilane, isobutyl trimethoxysilane, hexyl trimethoxysilane, octyl trimethoxysilane, decyl trimethoxysilane, dodecyl trimethoxysilane, phenyl trimethoxysilane, o-methylphenyl trimethoxysilane, and p-methylphenyl trimethoxysilane. In addition, inorganic particles treated to be hydrophobic by using higher fatty acid metal salts such as silicone oil, aluminum stearate, zinc stearate, and calcium stearate are also desirably used.

As the organic particles, particles of fluorocarbons in which fluorine binds to graphite, a polytetrafluoroethylene resin (PTFE), a fluorinated perfluoroalkoxy resin (PFA), a tetrafluoroethylene-pentafluoropropylene copolymer (FEP), ethylene-tetrafluoroethylene copolymer (ETFE), polychlorotrifluoroethylene (PCTFE), vinylidene fluoride (PVDF), vinyl fluoride (PVF), and the like are used.

The size of the particles used is desirably from 5 nm to 1000 nm, more desirably from 5 nm to 800 nm, and even more desirably from 5 nm to 700 nm, in terms of a volume average particle size. If the volume average particle size is less than the lower limit described above, a polishing ability tends to deteriorate. On the other hand, if the volume average particle size exceeds the upper limit described above, the surface of the electrophotographic photoreceptor tends to be easily damaged. The sum of the added amount of particles and lubricant particles described above is desirably 0.6% by mass or more.

As other inorganic oxides added to the toner, small size inorganic oxides having a primary particle size of 40 nm or less are used, in view of powder fluidity, charge control, and the like. It is desirable to further add inorganic oxides larger than the above oxides so as to reduce an adhesive force or to control charge. Known oxides may be used for the inorganic oxide particles, but for precise charge control, it is desirable to concurrently use silica and titanium oxide. If the small sized inorganic particles are surface-treated, dispersibility is improved, and an effect of improving powder fluidity is enhanced. In addition, adding carbonate such as calcium carbonate or magnesium carbonate or inorganic mineral such as hydrotalcite is also desirable for removing discharge products.

The color toner for electrophotography is used by being mixed with a carrier, and as the carrier, iron powder, glass beads, ferrite powder, nickel power, or a substance obtained by coating a resin onto the surface of the carrier is used. The mixing ratio between the color toner and the carrier is set arbitrarily.

Examples of the transfer device 40 include known transfer chargers such as a contact-type transfer charger using a belt, a roll, a film, a rubber blade, or the like, a scorotron transfer charger using corona discharge, and a corotron transfer charger.

As the intermediate transfer member 50, semiconductivity-imparted polyimide, polyamideimide, polycarbonate, polyarylate, polyester, or rubber, which is shaped like a belt (intermediate transfer belt), is used. In addition, as an embodiment of the intermediate transfer member 50, a drum-like member is used in addition to the belt-like member.

The image forming apparatus 100 may include, for example, an optical erasing device that performs optical erasing on the photoreceptor 7.

Figure 5:
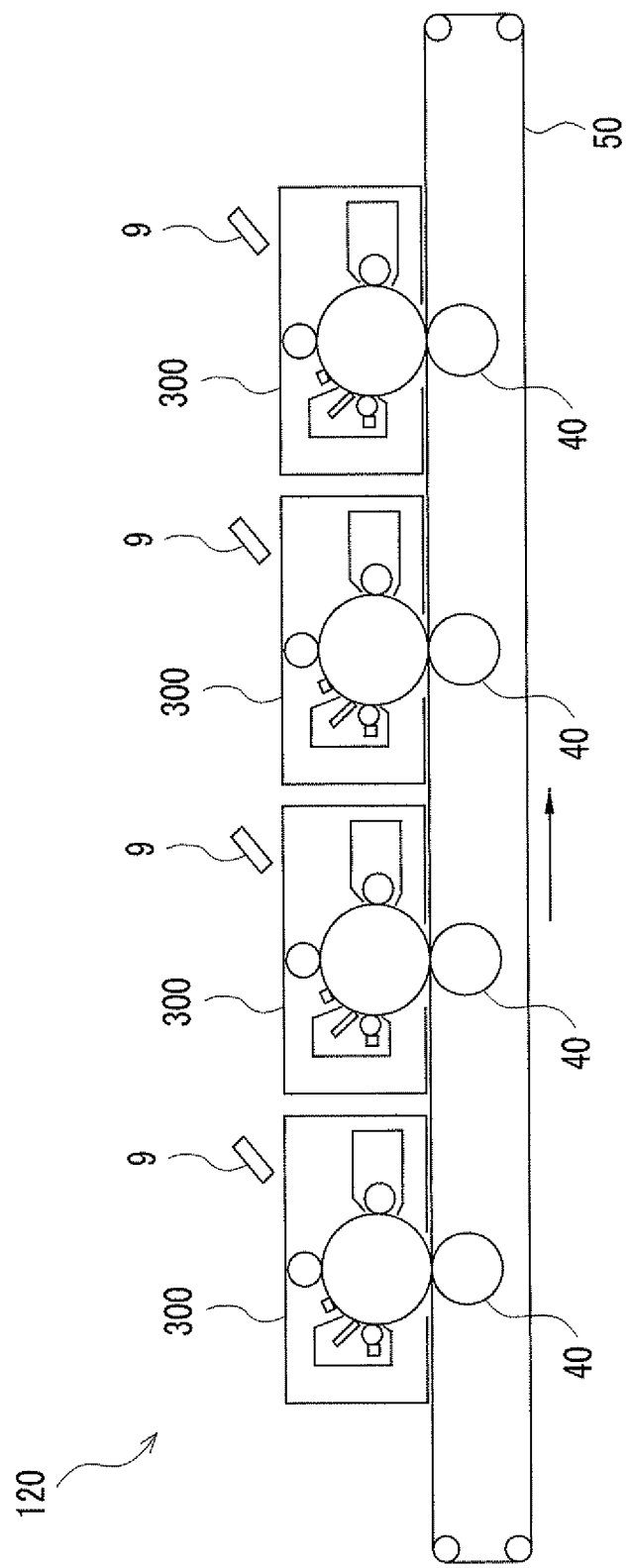
FIG. 5 is a schematic configuration view showing an image forming apparatus according to another exemplary embodiment.

FIG. 5 is a schematic cross-sectional view showing an image forming apparatus 120 according to another exemplary embodiment.

The image forming apparatus 120 shown in FIG. 5 is a tandem type color image forming apparatus on which four process cartridges 300 are mounted.

The image forming apparatus 120 has a configuration in which the four process cartridges 300 are arranged on the intermediate transfer member 50 in parallel, and one electrophotographic photoreceptor is used for a color. The image forming apparatus 120 has the same configuration as that of the image forming apparatus 100, except that the image forming apparatus 120 employs a tandem method.

When the electrophotographic photoreceptor of the exemplary embodiment of the invention is used for the tandem type image forming apparatus, since the electrical characteristics of four photoreceptors are stable, images excellent in color balance are obtained for a longer time.

In the image forming apparatus (process cartridge) according to the exemplary embodiment, the developing device (developing unit) desirably has a developing roll which is a developer holder moving (rotating) in the opposite direction to the movement direction (rotation direction) of the electrophotographic photoreceptor. Herein, the developing roll includes a cylindrical developing sleeve holding a developer on the surface thereof. Examples of the developing device include those having a configuration that includes a regulation member regulating the amount of a developer supplied to the developing sleeve. When the developing roll of the developing device moves (rotates) in the opposite direction to the rotation direction of the electrophotographic photoreceptor, the surface of the electrophotographic photoreceptor is rubbed against the toner remaining between the developing roll and the electrophotographic photoreceptor. Moreover, when the residual toner on the electrophotographic photoreceptor is cleaned, for example, the pushing pressure of a blade or the like is increased so as to improve the cleaning property of the toner having approximately a spherical shape, and consequently, the surface of the electrophotographic photoreceptor is rubbed strongly.

Due to the rubbing, the electrophotographic photoreceptor known in the related art is severely damaged, and abrasion, damage, filming of toner, or the like easily occurs, which leads to image deterioration. However, by forming the surface of the electrophotographic photoreceptor that has an increased concentration of the crosslinked substance of the specific charge transport material (particularly, a material that contains a high level or increased number of reactive functional groups and may produce a cured film having a high crosslink density) of the exemplary embodiment of the invention and is made into a thick film to obtain excellent electrical characteristics, it is possible to maintain high image quality for a long time. It is considered that the deposition of the discharge product is suppressed for a very long time.

In the image forming apparatus of the exemplary embodiment, the interval between the developing sleeve and the photoreceptor is set to desirably from 200 μm to 600 μm, and more desirably from 300 μm to 500 μm, in view of suppressing the deposition of the discharge product for a longer time. From the same point of view, the interval between the developing sleeve and a regulation blade as the above-described regulation member regulating the amount of a developer is set to desirably from 300 μm to 1000 μm, and more desirably from 400 μm to 750 μm.

In addition, in view of suppressing the deposition of the discharge product for a longer time, the absolute value of the movement speed of the developing roll surface is set to desirably from 1.5 times to 2.5 times, and more desirably from 1.7 times to 2.0 times the absolute value (process speed) of the movement speed of the photoreceptor surface.

In the image forming apparatus (process cartridge) according to the exemplary embodiment, the developing device (developing unit) desirably includes a developer holder having a magnetic material and develops electrostatic latent images with a two-component developer containing a magnetic carrier and a toner. In this configuration, compared to the case of the single-component developer, particularly, the non-magnetic single-component developer, more excellent image quality is obtained in a color image, a higher level of high image quality is realized, and the life of the apparatus is further extended.

In the image forming apparatus (process cartridge) according to the exemplary embodiment, an image forming apparatus using a dry developer was described. However, the image forming apparatus (process cartridge) may use a liquid developer. Particularly, in the image forming apparatus (process cartridge) using a liquid developer, due to the liquid components in the liquid developer, the uppermost surface layer of the electrophotographic photoreceptor is, for example, swollen, whereby the uppermost surface layer is easily cracked or receives cleaning damage by cleaning. However, such problems are improved by using the electrophotographic photoreceptor according to the exemplary embodiment, and consequently, stabilized images are obtained for a long time.

Figure 10:
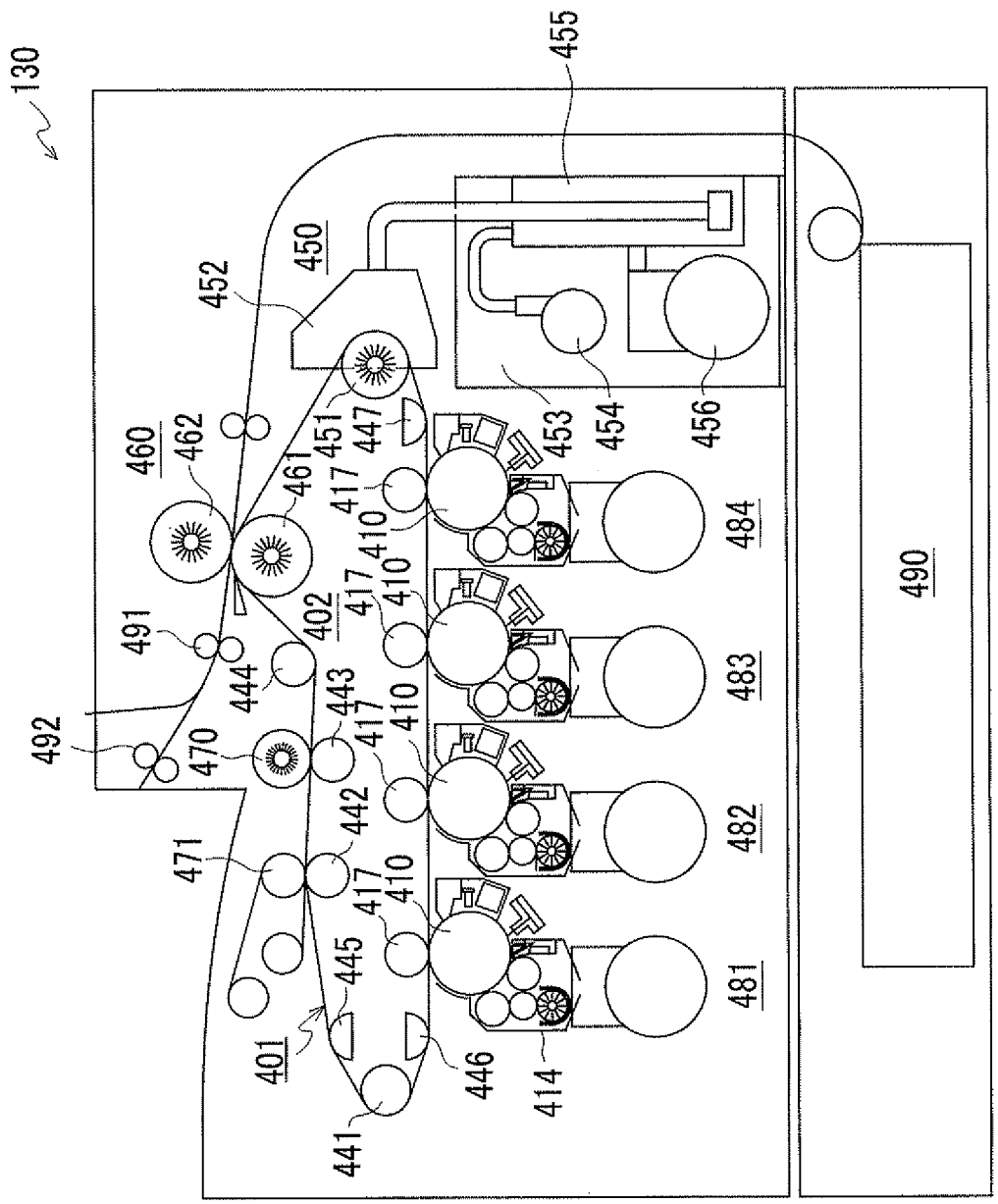
FIG. 10 is a schematic configuration view showing an image forming apparatus according to another exemplary embodiment.
Figure 11:
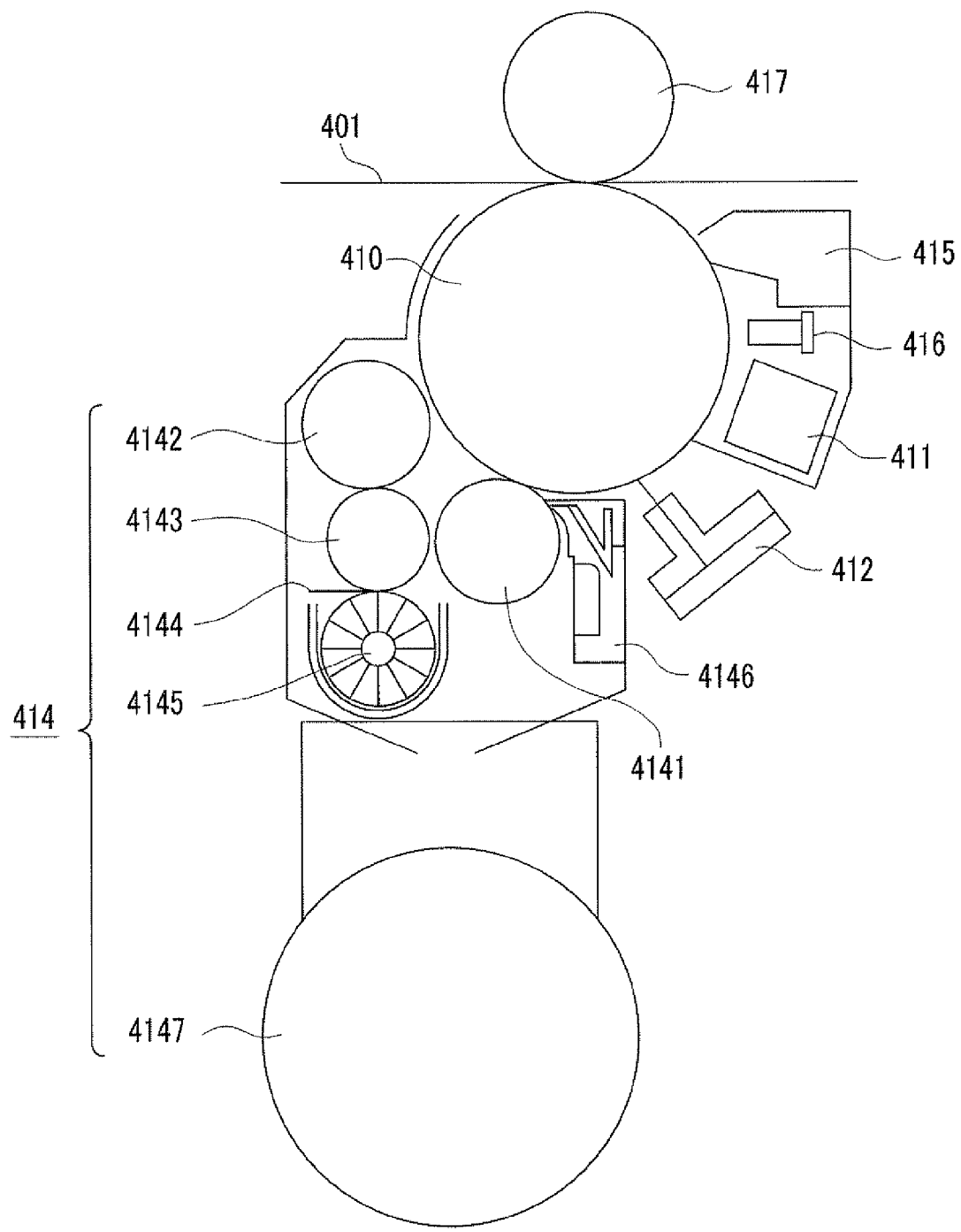
FIG. 11 is a schematic configuration view showing a developing device in the image forming apparatus shown in FIG. 10.

FIG. 10 is a schematic configuration view showing an image forming apparatus according to the other embodiment, and FIG. 11 is a schematic configuration view showing an image forming unit in the image forming apparatus shown in FIG. 10.

An image forming apparatus 130 shown in FIG. 10 is mainly configured with a belt-like intermediate transfer member 401, image forming units 481, 482, 483, and 484 for each color, a heating portion 450 (an example of a layer forming unit), and a transfer and fixing portion 460.

As shown in FIG. 11, the image forming unit 481 is configured with an electrophotographic photoreceptor 410, a charger 411 that charges the electrophotographic photoreceptor 410, an LED array head 412 (an example of an electrostatic latent image forming unit) that performs image exposure for forming an electrostatic latent image on the surface of the charged electrophotographic photoreceptor 410 according to image information, a developing device 414 that develops the electrostatic latent image formed on the electrophotographic photoreceptor 410 by using a liquid developer, a cleaner 415 that cleans the photoreceptor surface, an eraser 416, and a transfer roll 417 (an example of a primary transfer unit) that faces the electrophotographic photoreceptor 410 across the belt-like intermediate transfer member 401 and is applied with transfer bias for transferring the developed image which has been formed on the electrophotographic photoreceptor 410 and developed by the liquid developer to the belt-like intermediate transfer member 401.

As shown in FIG. 11, in the developing device 414, a developing roll 4141, a liquid draining roll 4142, a developer cleaning roll 4143, a developer cleaning blade 4144, a developer cleaning brush 4145, a circulating pump (not shown), a liquid developer supplying path 4146, and a developer cartridge 4147 are provided.

As the liquid developer used herein, a liquid developer in which particles having a heat melting and fixing type of resin such as polyester or polystyrene as a main component are dispersed, or a liquid developer to be a layer (which will be referred to as "to be a film", hereinafter) by removing a surplus dispersion medium (carrier liquid) and increasing the proportion of the solid contents in the liquid developer is used. Specific materials to be a film are described in detail in U.S. Pat. No. 5,650,253 (Column 10, Line 8 to Column 13, Line 14) and U.S. Pat. No. 5,698,616.

The developer to be a film refers to a liquid developer in which micro-substances (such as a micro-toner) having a glass transition point (temperature) lower than room temperature are dispersed in a carrier liquid. Generally, the substances do not contact each other and do not aggregate. However, when the carrier liquid is removed, only the substances remain, and if the substances are attached as a film shape, they bind to each other at room temperature, thereby forming a film. The substance is obtained by mixing ethyl alcohol with methyl methacrylate, and the glass transition temperature is set by the mixing ratio thereof.

Other image forming units 482, 483, and 484 also have the same configuration. In the developing units of the respective image forming units, different colors (yellow, magenta, cyan, and black) of liquid developers are contained. In addition, in the respective image forming units 481, 482, 483, and 484, the electrophotographic photoreceptor, the developing device, and the like are formed into a cartridge.

In the above configuration, examples of the material of the belt-like intermediate transfer member 401 include a PET film (polyethylene terephthalate film) coated with silicon rubber or a fluororesin, a polyimide film, and the like.

The electrophotographic photoreceptor 410 contacts the belt-like intermediate transfer member 401 through the upper surface thereof, and moves at the same speed as the belt-like intermediate transfer member 401.

As the charger 411, for example, a corona charger is used. The electrophotographic photoreceptors 410 in the image forming unit 481, 482, 483, and 484 have the same circumferential length. In addition, the interval between the respective transfer rolls 417 arranged is configured so as to be the same as the circumferential length of the electrophotographic photoreceptor 410 or to be an integer multiple of the circumferential length.

The heating portion 450 is configured with a heating roll 451 that is disposed so as to rotate while contacting the inner surface of the belt-like intermediate transfer member 401, a storage chamber 452 that is disposed so as to face the heating roll 451 and surround the outer surface of the belt-like intermediate transfer member 401, and a carrier liquid recovering portion 453 that recovers vapor of the carrier liquid and the carrier liquid from the storage chamber 452. On the carrier liquid recovering portion 453, a suction blade 454 that sucks the vapor of the carrier liquid in the storage chamber 452, a condensing portion 455 that liquefies the vapor of the carrier liquid, and a recovering cartridge 456 that recovers the carrier liquid from the condensing portion 455 are mounted.

The transferring and fixing portion 460 (an example of a secondary transfer unit) is configured with a transfer supporting roll 461 that rotatably supports the belt-like intermediate transfer member 401, and a transferring and fixing roll 462 that rotates while pushing a recording medium passing through the transferring and fixing unit 460 to the belt-like intermediate transfer member 401 side, and also includes a heating element in the inside thereof.

In addition, a cleaning roll 470 and a cleaning web 471 that clean the top of the belt-like intermediate transfer member 401 before a color image is formed on the belt-like intermediate transfer member 401, supporting rolls 441 to 444 that support the rotation driving of the belt-like intermediate transfer member 401, and supporting shoes 445 to 447 are provided.

The belt-like intermediate transfer member 401 configures an intermediate member unit 402 with transfer rolls 417 of image forming units for each color, the heating roll 451, the transfer supporting roll 461, the supporting rolls 441 to 444, the supporting shoes 445 to 447, the cleaning roll 470, and a cleaning web 471. The belt-like intermediate transfer member 401 is configured such that the vicinity of the supporting roll 441 integrally moves up and down based on vicinity of the heating roll 451 as a supporting point.

Hereinafter, the operation of the image forming apparatus using the liquid developer shown in FIG. 10 will be described.

First, in the image forming unit 481, the LED array head 412 performs the image exposure on the electrophotographic photoreceptor 410 of which the surface has been charged by the charger 411, according to yellow image information, whereby an electrostatic latent image is formed. This electrostatic latent image is developed with a yellow liquid developer by the developing device 414.

Herein, the development is performed through the following steps. The yellow liquid developer passes through the liquid developer supplying path 4146 by the circulation pump from the developer cartridge 4147, and is supplied to the vicinity of a place where the developing roll 4141 and the electrophotographic photoreceptor 410 approach. Due to a development field formed between the electrostatic latent image on the electrophotographic photoreceptor 410 and the developing roll 4141, coloring solid contents with charges in the supplied liquid developer move to the electrostatic latent image side to be an image on the electrophotographic photoreceptor 410.

Subsequently, the liquid draining roll 4142 removes the carrier liquid from the top of the electrophotographic photoreceptor 410 so as to yield a proportion of the carrier liquid required for the next transferring. On the surface of the electrophotographic photoreceptor 410 having passed through the developing device 414 in this manner, a yellow image developed by the yellow liquid developer is formed.

In the developing device 414, the developer cleaning roll 4143 removes the liquid developer remaining on the developing roll 4141 after developing operation and the liquid developer attached to a squeeze roll due to a squeeze operation, and the developer cleaning blade 4144 and the developer cleaning brush 4145 clean the developer cleaning roll 4143. In this manner, developing operation is stably performed all the time. The configuration and operations of the developing device is described in detail in JP-A-11-249444.

For the developing roll 4141, the level of solid contents ratio in the liquid developer is automatically controlled by at least one of the developing device 414 and the developer cartridge 4147 such that a liquid developer containing a constant ratio of a solid contents is supplied.

The developed yellow image formed on the electrophotographic photoreceptor 410 contacts the belt-like intermediate transfer member 401 through the upper surface thereof by the rotation of the electrophotographic photoreceptor 410. The image is then transferred to the belt-like intermediate transfer member 401 by contact electrostatic transfer, by the transfer roll 417 that is pressed on the electrophotographic photoreceptor 410 while facing the electrophotographic photoreceptor 410 across the belt-like intermediate transfer member 401 and is applied with the transfer bias.

From the electrophotographic photoreceptor 410 having completed the contact electrostatic transfer, the liquid developer remaining after the transfer is removed by the cleaner 415, and the electricity of electrophotographic photoreceptor 410 is erased by the eraser 416 so that the electrophotographic photoreceptor 410 is used for the next image formation.

The same operation is performed in the image forming units 482, 483, and 484. The circumferential length of the electrophotographic photoreceptors 410 used in the respective image forming units is the same. In addition, the developed images of each color formed on the respective photoreceptors are sequentially and electrostatically transferred onto the belt-like intermediate transfer member 401, by the transfer rolls arranged in the interval that is as long as the circumferential length of the photoreceptor or is the integer multiple of the circumferential length. Accordingly, the respective developed images of yellow, magenta, cyan, and black, which are formed on the respective electrophotographic photoreceptors 410 in consideration of the overlapped position on the belt-like intermediate transfer member 401, are sequentially transferred onto the belt-like intermediate transfer member 401 by contact electrostatic transfer with a high accuracy, while overlapping with each other without misalignment, even if eccentricity occurs in the electrophotographic photoreceptor 410. In this manner, on the belt-like intermediate transfer member 401 having passed through the image forming unit 484, an image developed by liquid developer of each color is formed.

In the heating portion 450, the developed image formed on the belt-like intermediate transfer member 401 is heated by the heating roller 451 from the back surface of the belt-like intermediate transfer member 401. As a result, the carrier liquid as the dispersion medium is almost completely evaporated, and an image of a film is formed. This is because if the liquid developer is a developer in which particles having heat melting and fixing type resin as a main component are dispersed, the dispersed particles become a film by being melted through the removal of the surplus dispersion medium and heating by the heating roll 451. Alternatively, this is because the liquid developer is a developer that becomes a film by increasing the solid contents ratio in the liquid developer through the removal of the surplus dispersion medium (carrier liquid).

In the heating portion 450, the vapor of the carrier liquid in the storage chamber 452, which is generated by being heated and evaporated by the heating roll 451, is introduced to the condensing portion 455 by the suction blade 454 in the carrier liquid recovering portion 453 and liquefied. The re-liquefied carrier liquid is guided to the recovering cartridge 456 and recovered.

In a transferring and fixing portion 460, the belt-like intermediate transfer member 401 that has passed the heating portion 450 and has a film-like (layer-like) image formed on the top thereof is transferred by heat and pressure to a transfer medium (for example, normal paper) that has been transported in time from a paper storage portion 490 in the lower portion of the apparatus, by the transferring and supporting roll 461 and transferring and fixing roll 462. In this manner, an image is formed on the transfer medium and discharged outside the apparatus by discharge rolls 491 and 492. In this transferring, the adhesive force of the image of a film that is formed on the belt-like intermediate transfer member 401 with respect to the belt-like intermediate transfer member 401 is weaker than the adhesive force of the image of a film with respect to the transfer medium. Since the image is transferred to the transfer medium by such a difference in the adhesive force, an electrostatic force is not imparted during transferring. Moreover, the binding force of the image of a film as a film is stronger than the adhesive force with respect to the transfer medium.

From the belt-like intermediate transfer member 401 having passed through the transferring and fixing portion 460, the solid contents that remain after the transferring and substances that are contained in the solid contents and hinder the function of the belt-like intermediate transfer member 401 are recovered and removed by the cleaning roll 470 and the cleaning web 471 having a heat source in the inside thereof. Thereafter, the belt-like intermediate transfer member 401 is used for the next image formation.

After the image is formed in the above-described manner, in the intermediate member unit 402, the vicinity of the supporting roll 441 moves upward integrally, based on the vicinity of the heating roll 451 as a supporting point. In this manner, the belt-like intermediate transfer member 401 is separated from the electrophotographic photoreceptors 410 of the respective image forming units. The transferring and fixing roll 462 is also separated from the belt-like intermediate transfer member 401 in the same manner.

When there is a request for image formation again, the intermediate member unit 402 operates such that the belt-like intermediate transfer member 401 contacts the electrophotographic photoreceptors 410 of the respective image forming units, and similarly, the transferring and fixing roll 462 also operates to contact the belt-like intermediate transfer member 401. The operation of the transferring and fixing roll 462 may be performed with timing in which the image is transferred to the recording medium.

The image forming apparatus using the liquid developer is not limited to the image forming apparatus 130 shown in FIG. 10. For example, the image forming apparatus may be the image forming apparatus shown in FIG. 12.

Figure 12:
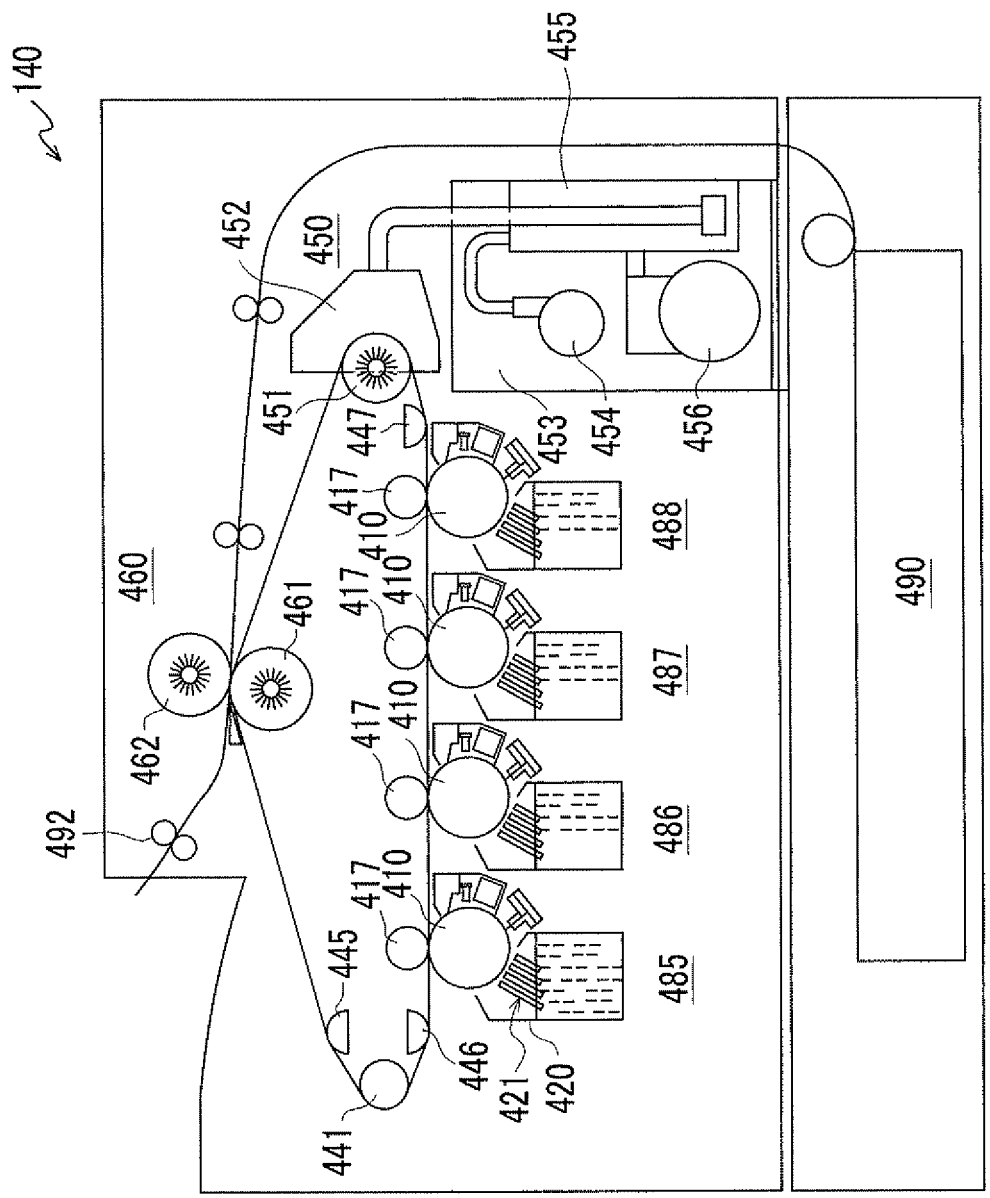
FIG. 12 is a schematic configuration view showing an image forming apparatus according to another exemplary embodiment.

FIG. 12 is a schematic configuration view showing an image forming apparatus according to another exemplary embodiment.

Similarly to the configuration of the image forming apparatus 130 shown in FIG. 10, an image forming apparatus 140 shown in FIG. 12 is mainly configured with the belt-like intermediate transfer member 401, image forming units 485, 486, 487, and 488 for each color, the heating portion 450, and the transferring and fixing portion 460.

The image forming apparatus 140 shown in FIG. 12 is different from the image forming apparatus 130 shown in FIG. 10 in that the belt-like intermediate transfer member 401 runs approximately in a triangle shape, and in the configuration of a developing device 420 in image forming units 485, 486, 487, and 488 for each color. The heating portion 450 and the transferring and fixing portion 460 are the same as those in the image forming apparatus 130 shown in FIG. 10. In addition, the cleaning roll 470 and the cleaning web 471 are omitted in the drawing.

While rotating and running, the belt-like intermediate transfer member 401 performs a bending operation. Since this bending operation affects the stabilized running and the life of the belt-like intermediate transfer member 401, the belt-like intermediate transfer member 401 is allowed to run approximately in a triangle shape so as to reduce the bending operation as much as possible.

In the developing device 420, recording heads 421 that selectively discharge and attach the liquid developer to the electrostatic latent image formed on the electrophotographic photoreceptor 410 are arranged in plural columns, instead of the developing roll, the liquid draining roll, and the like.

In each column of the recording heads 421, a large number of recording electrodes 422 are evenly arranged in the longitudinal direction of the electrophotographic photoreceptor 410, and a discharging electric field is formed between the potential of the electrostatic latent image formed on the electrophotographic photoreceptor 410 and the discharging bias potential applied to the recording electrodes 422. In addition, coloring solid contents with charges in the liquid developer supplied to the recording electrodes 422 move to the electrostatic latent image side to be an image portion on the electrophotographic photoreceptor 410 and develop the image.

Figure 13:
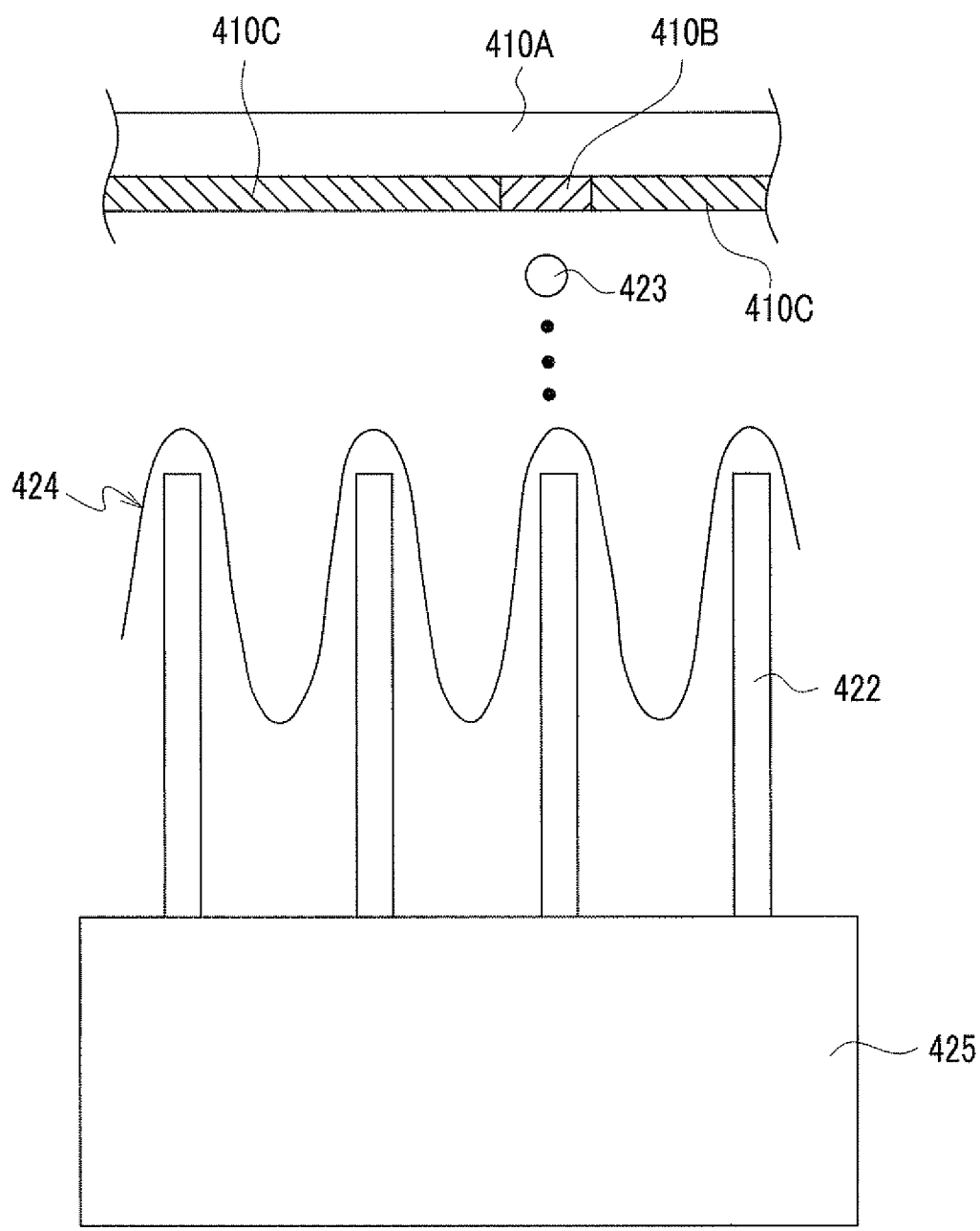
FIG. 13 is a schematic view showing a meniscus of a liquid developer that is formed around printing electrodes of the developing device and how the liquid moves to an image portion in the image forming apparatus shown in FIG. 12.

Around the recording electrodes 422, a meniscus (a liquid-holding form that is formed on a member or between members contacting a liquid due to the viscosity or surface tension of the liquid, and the surface energy of the surface of the contacting member) 424 of the liquid developer is formed. FIG. 13 is a view showing the state of the meniscus. On an electrophotographic photoreceptor 410A to which a liquid particle 423 of the liquid developer flies, an electrostatic latent image to be an image portion is formed. At this time, an electrostatic latent image potential of from 50 V to 100 V has been applied to an image portion 410B, and a potential of from 500 V to 600 V has been applied to a non-image portion 410C. At this time, when a discharging bias potential of about 1000 V is applied to the recording electrodes 422 via a bias potential supplying portion 425, due to electric field concentration, a liquid developer having a higher solid contents ratio compared to the supplied liquid developer, that is, a high concentration liquid developer is supplied to the tip of the recording electrodes 422. Moreover, due to a potential difference (a threshold of a potential difference required for from 700 V to 800 V to discharge) between the electrostatic latent image potential of the image portion 410C on the electrophotographic photoreceptor 410A and the discharging bias potential of the recording electrodes 422, the liquid particles 423 from the high concentration liquid developer discharge and are attached to the electrostatic latent image portion (image portion) of the electrophotographic photoreceptor 410A. In addition, in the developing device 420, the developing device itself plays a role of a developer cartridge.

The operation of the image forming apparatus 140 shown in FIG. 12 is the same as that of the image forming apparatus 130 shown in FIG. 10, except for the running pattern of the belt-like intermediate transfer member 401 and the operation of the developing device 420. Therefore, description thereof is omitted.

Figure 14:
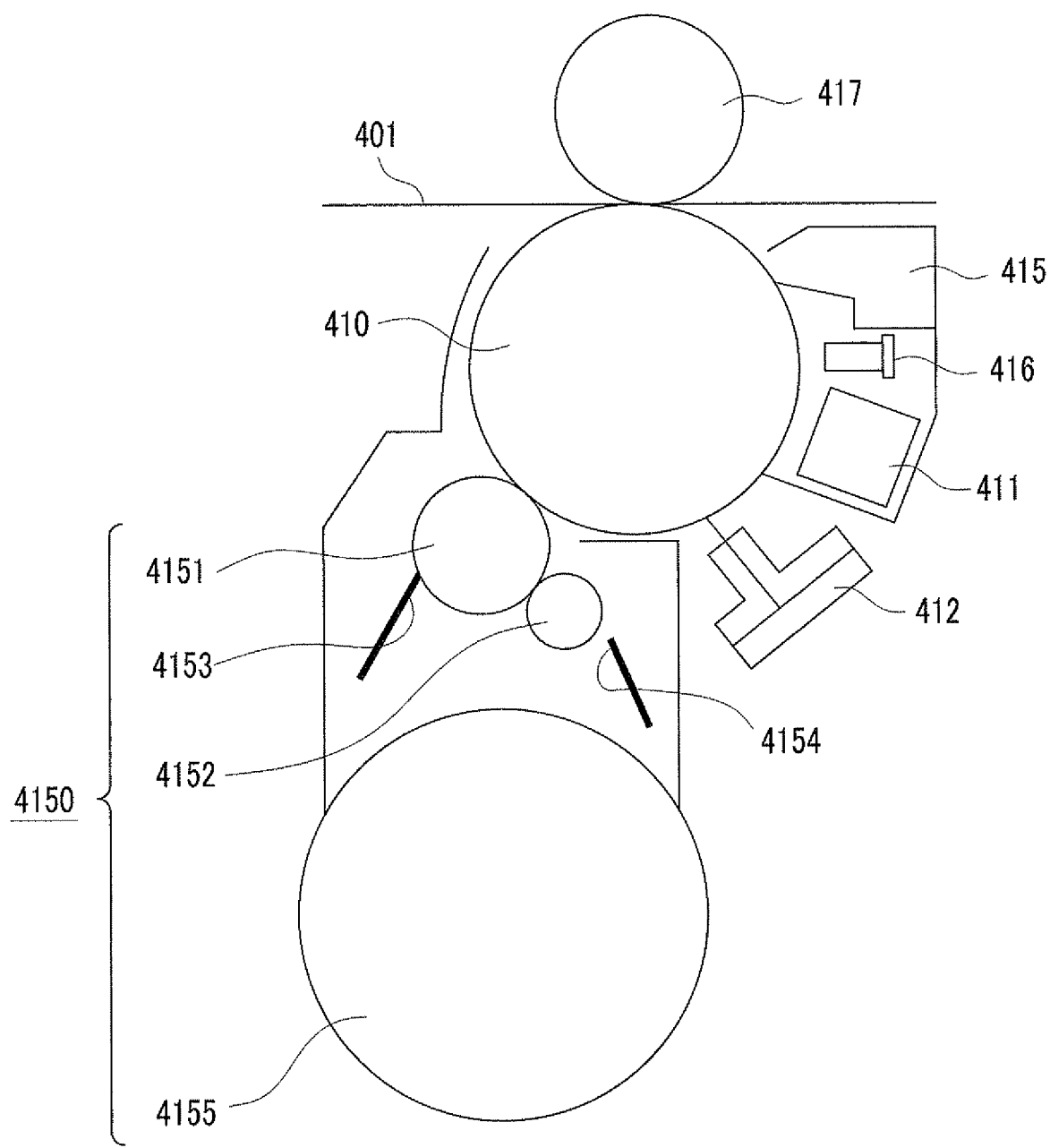
FIG. 14 is a schematic configuration view showing another developing device in the image forming apparatuses shown in FIGS. 10 and 13.

Herein, in the image forming apparatus using the liquid developer, the developing device is not limited to the above-described configuration, and the developing device may be, for example, the developing device shown in FIG. 14.

FIG. 14 is a schematic configuration view showing another developing device in the image forming apparatus shown in FIG. 10 or 12.

When the electrostatic latent image formed on the electrophotographic photoreceptor 410 is developed using a developing roll 4151 in the image forming apparatus 130 or 140 shown in FIG. 10 or 12, a developing device 4150 shown in FIG. 14 forms a liquid developer layer including a higher solid contents ratio compared to the liquid developer supplied from a developer cartridge 4155 on the developing roll 4151, and develops an image by using the liquid developer layer of which the concentration has been increased.

In order to form the liquid developer layer having an increased solid contents ratio on the developing roll 4151, an electric field is formed by creating a potential difference between a supplying roll 4152 and the developing roll 4151, whereby the liquid developer layer having a higher solid contents ratio compared to the proportion of solid contents in the liquid developer from the developer cartridge 4155 is formed on the developing roll 4151. For the developing roll 4151 and the supplying roll 4152, cleaning brushes 4153 and 4154 are arranged to clean the surface of the respective rolls.

In the exemplary embodiment described so far, a case has been described in which the novel reactive compound according to the exemplary embodiment is used for the uppermost surface layer of the electrophotographic photoreceptor, but the exemplary embodiment is not limited thereto. The cured film cured using the compound according to the exemplary embodiment is applied to, for example, photoelectric conversion devices such as an organic electroluminescence element, an organic solar cell, a memory device, and a wavelength conversion element.

EXAMPLES

The exemplary embodiment of the invention will be described in more detail based on the following examples, but the exemplary embodiment of the invention is not limited thereto.

Synthesis Example 1

Synthesis of Compound (I)-44

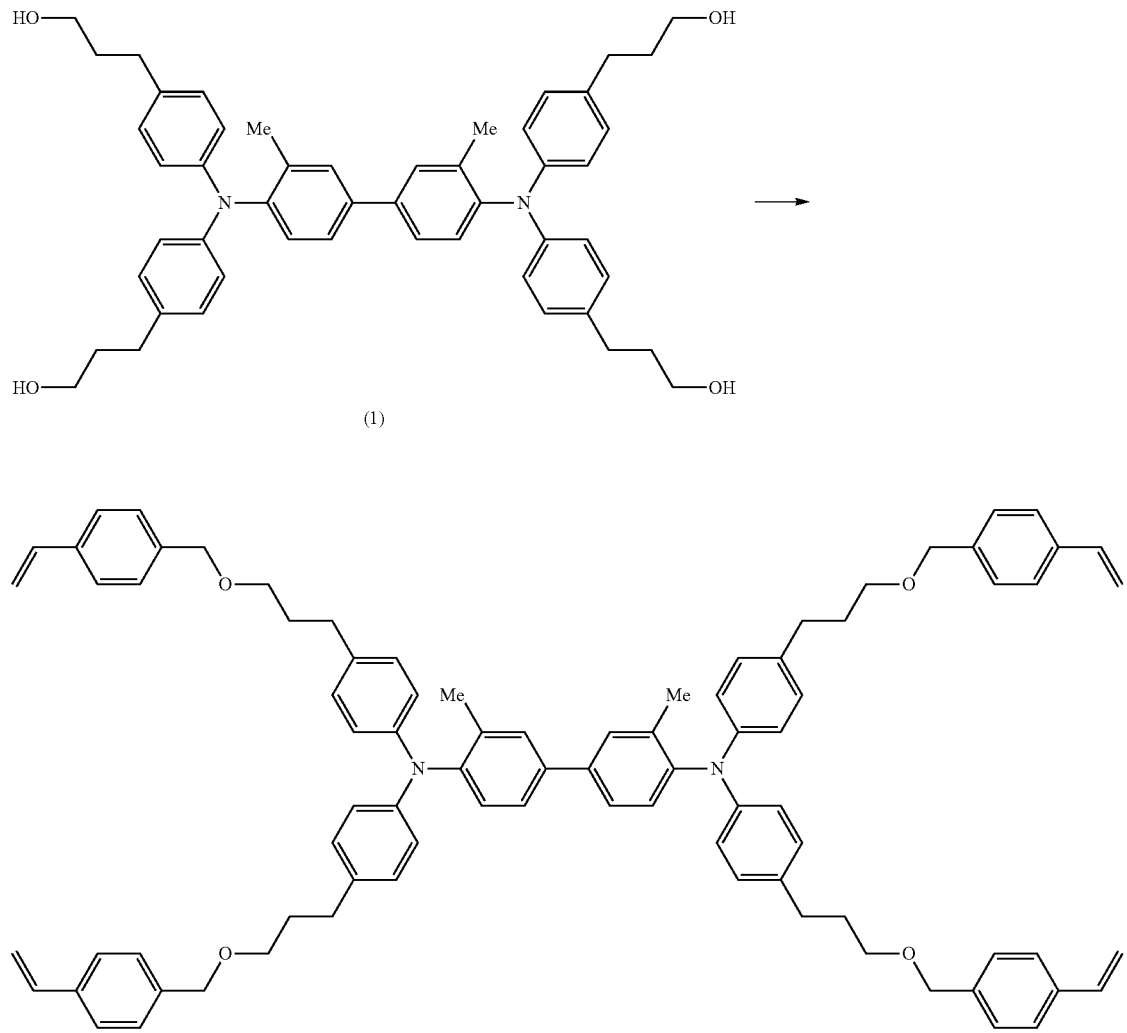 [SMILES: Cc1cc(-c2ccc(N(c3ccc(CCCO)cc3)c3ccc(CCCO)cc3)c(C)c2)ccc1N(c1ccc(CCCO)cc1)c1ccc(CCCO)cc1 ; C=Cc1ccc(COCCCc2ccc(N(c3ccc(CCCOCc4ccc(C=C)cc4)cc3)c3ccc(-c4ccc(N(c5ccc(CCCOCc6ccc(C=C)cc6)cc5)c5ccc(CCCOCc6ccc(C=C)cc6)cc5)c(C)c4)cc3C)cc2)cc1]

Figure 7:
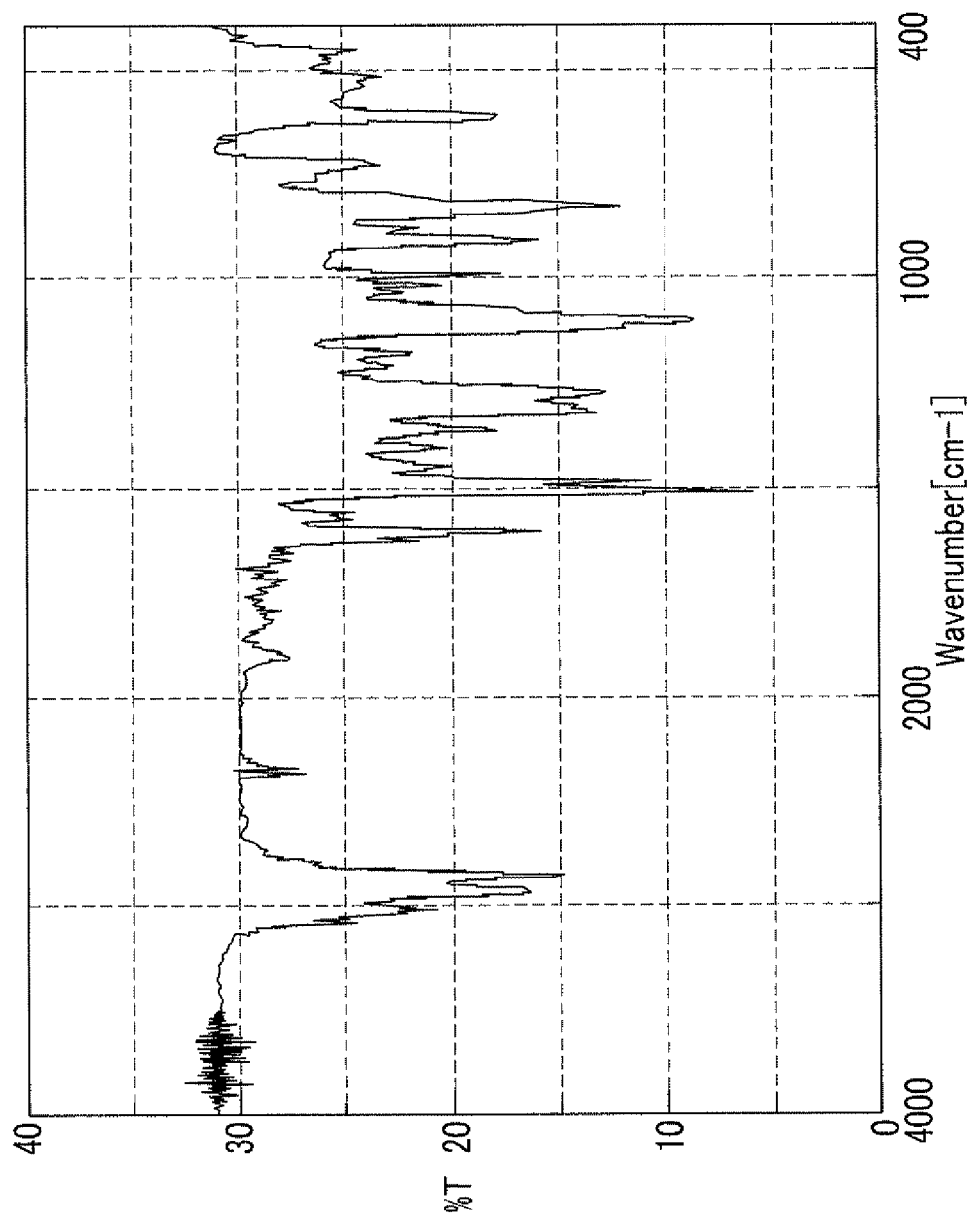
FIG. 7 is an IR spectrum of a compound (I)-44.

To a 500 ml flask, 10 g of the above compound (1), 7.2 g of t-butoxy potassium, 200 ml of tetrahydrofuran, and 0.2 g of nitrobenzene are added. While this mixture is stirred under a nitrogen gas flow, a solution obtained by dissolving 10 g of 4-chloromethyl styrene in 100 ml of tetrahydrofuran is slowly added dropwise thereto. After the completion of the dropwise addition, the resultant is heated and refluxed for 4 hours, followed by cooling, poured into water, and extracted with toluene. After the toluene layer is sufficiently washed with water, followed by concentration, the obtained oily substance is purified by silica gel column chromatography, thereby obtaining 12 g of oily (I)-44. The IR spectrum of the obtained compound (I)-44 is shown in FIG. 7.

Synthesis Example 2

Synthesis of Compound (I)-52

Figure 8:
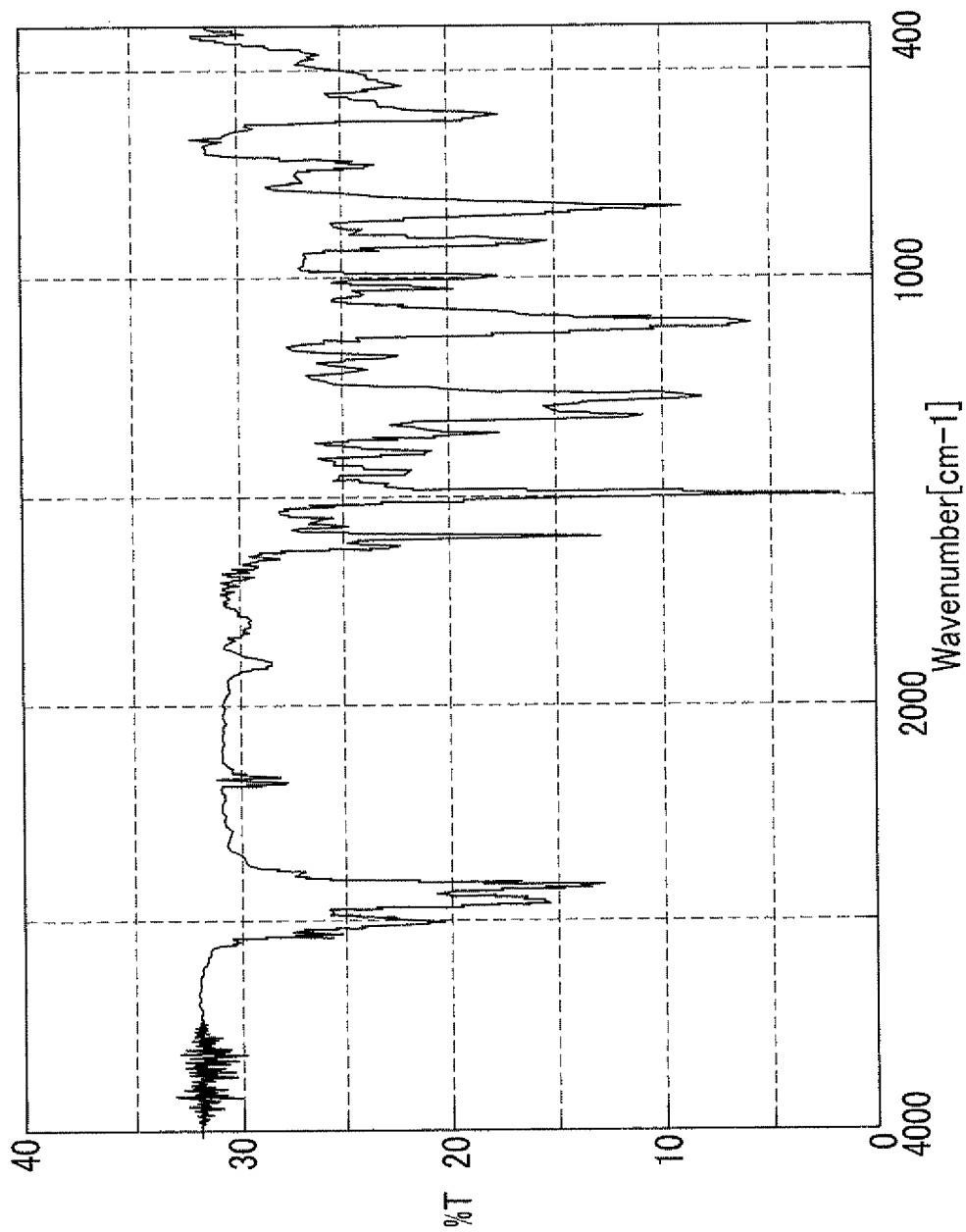
FIG. 8 is an IR spectrum of a compound (I)-52.

To a 500 ml flask, 22 g of the above compound (2), 33 g of t-butoxy potassium, 300 ml of tetrahydrofuran, and 0.2 g of nitrobenzene are added. While this mixture is stirred under a nitrogen gas flow, a solution obtained by dissolving 25 g of 4-chloromethyl styrene in 150 ml of tetrahydrofuran is slowly added dropwise thereto. After the completion of dropwise addition, the resultant is heated and refluxed for 4 hours, followed by cooling, poured into water, and extracted with toluene. After the toluene layer is sufficiently washed with water, followed by concentration, the obtained oily substance is purified by silica gel column chromatography, thereby obtaining 29 g of oily (I)-52. The IR spectrum of the obtained compound (I)-52 is shown in FIG. 8.

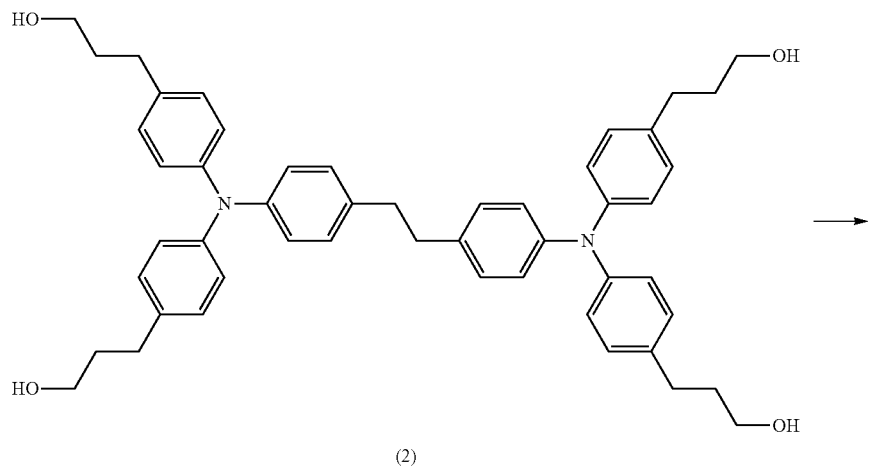

(2)

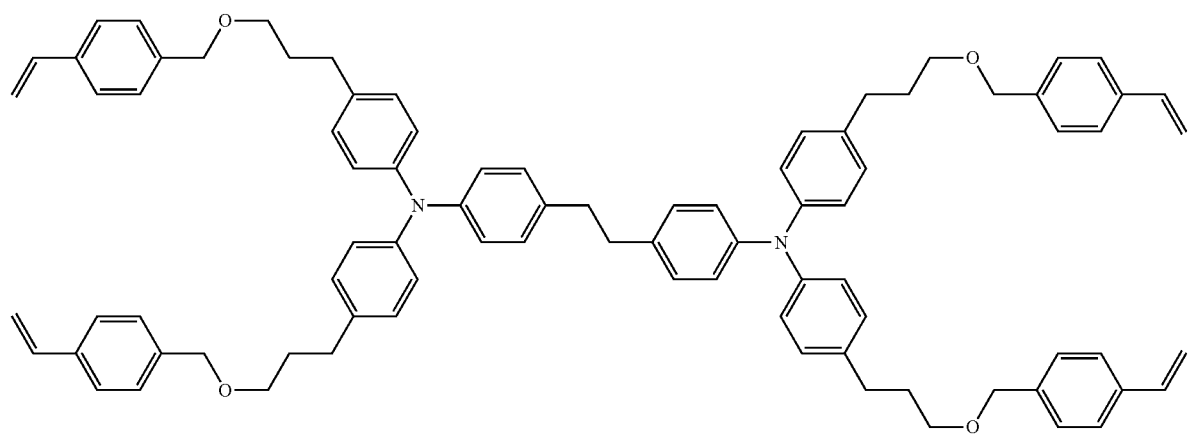

Synthesis Example 3

Synthesis of Compound (I)-28

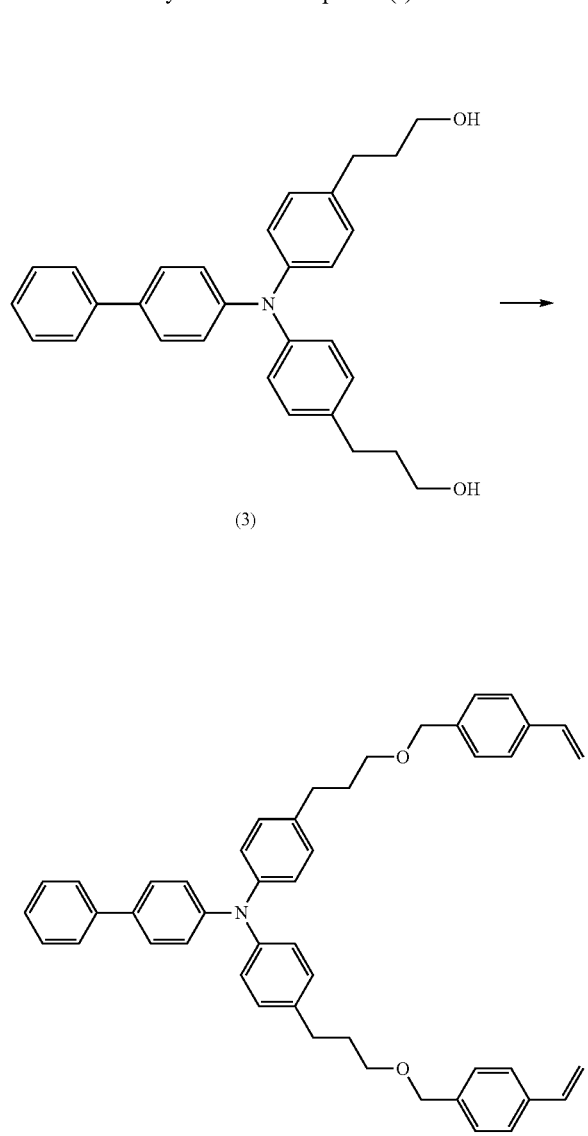

(3)

Figure 15:
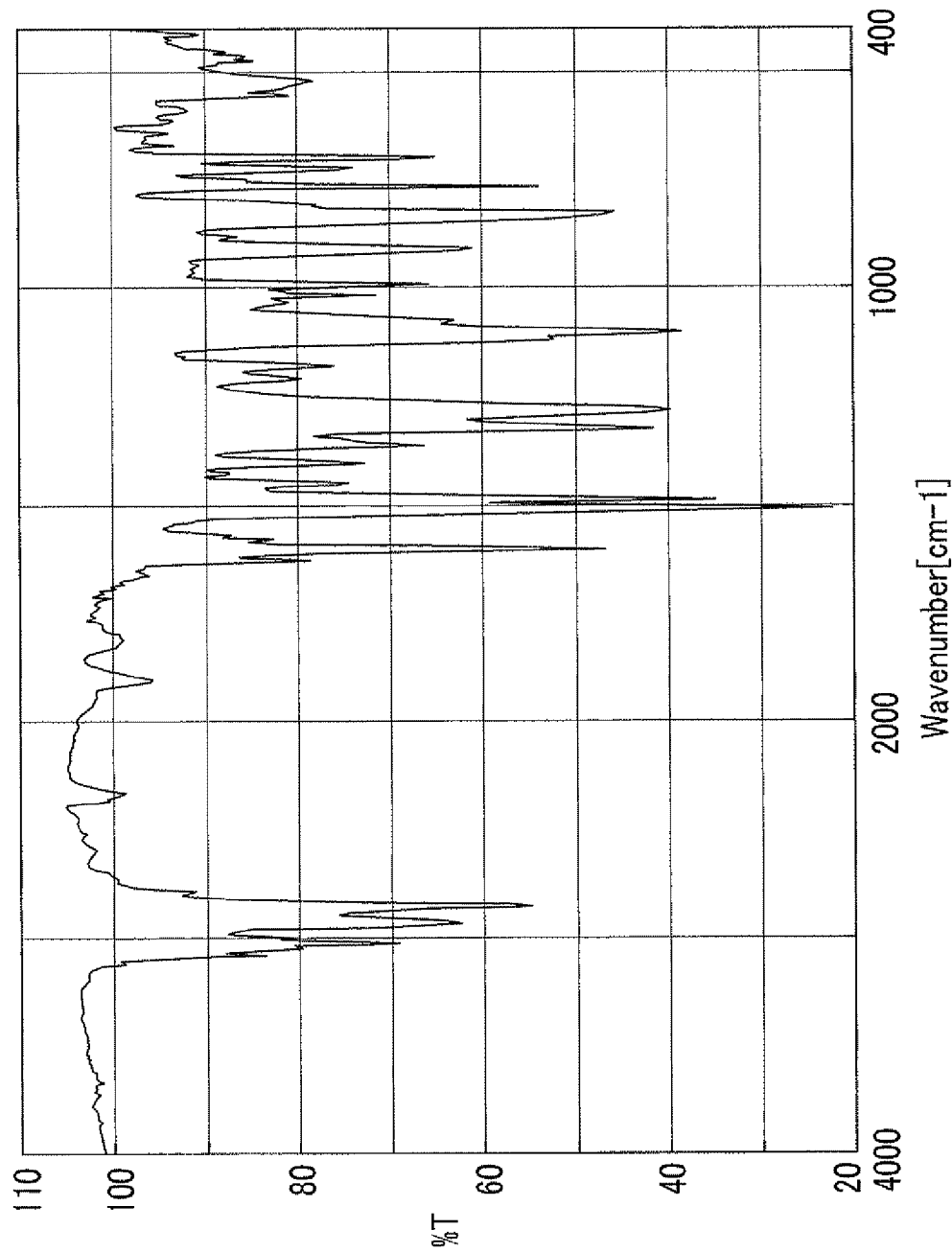
FIG. 15 is an IR spectrum of a compound (I)-28.

To a 500 ml flask, 50 g of the above compound (3), 30 g of t-butoxy potassium, 250 ml of tetrahydrofuran, and 0.2 g of nitrobenzene are added. While this mixture is stirred under a nitrogen gas flow, a solution obtained by dissolving 62 g of 4-iodomethyl styrene in 100 ml of tetrahydrofuran is slowly added dropwise thereto. After the completion of dropwise addition, the resultant is heated and refluxed for 4 hours, followed by cooling, poured into water, and extracted with toluene. After the toluene layer is sufficiently washed with water, followed by concentration, the obtained oily substance is purified by silica gel column chromatography, thereby obtaining 55 g of oily (I)-28. The IR spectrum of the obtained compound (I)-28 is shown in FIG. 15.

Synthesis Example 4

Synthesis of Compound (I)-61

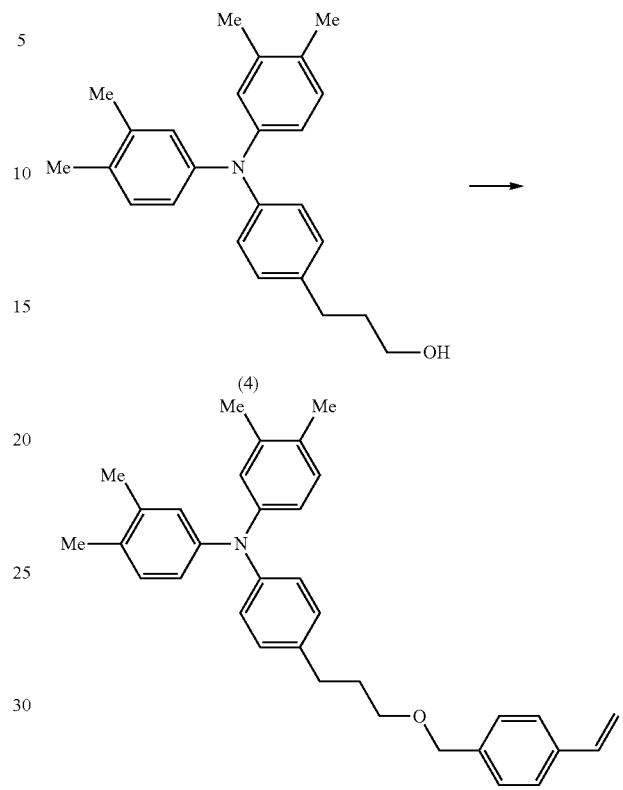

(4)

Figure 16:
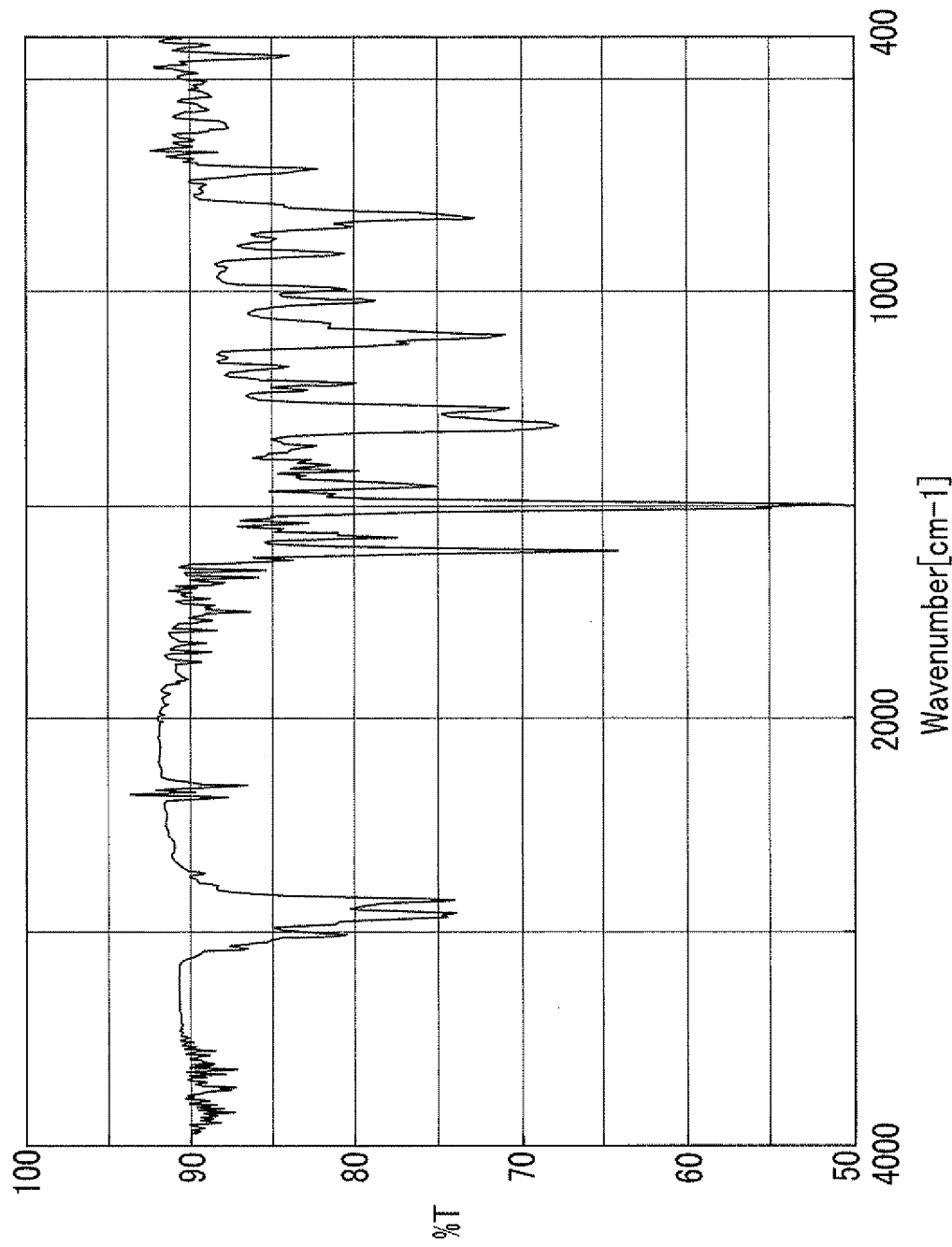
FIG. 16 is an IR spectrum of a compound (I)-61.

To a 500 ml flask, 70 g of the above compound (4), 26 g of t-butoxy potassium, 300 ml of tetrahydrofuran, and 0.2 g of nitrobenzene are added. While this mixture is stirred under a nitrogen gas flow, a solution obtained by dissolving 50 g of 4-chloromethyl styrene in 100 ml of tetrahydrofuran is slowly added dropwise thereto. After the completion of dropwise addition, the resultant is heated and refluxed for 4 hours, followed by cooling, poured into water, and extracted with toluene. After the toluene layer is sufficiently washed with water, followed by concentration, the obtained oily substance is purified by silica gel column chromatography, and then the substance is recrystallized from hexane, thereby obtaining 51 g of colorless crystalline (I)-61. The IR spectrum of the obtained compound (I)-61 is shown in FIG. 16.

Synthesis Example 5

Synthesis of Compound (I)-62

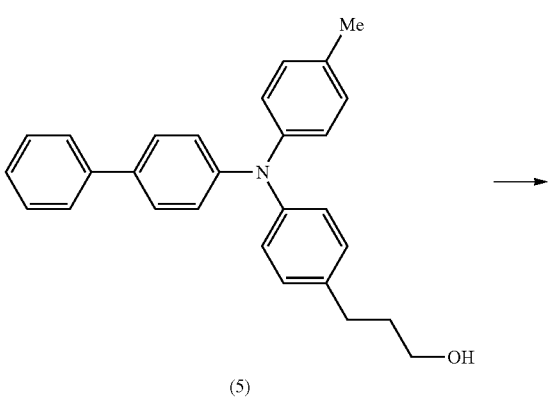

(5)

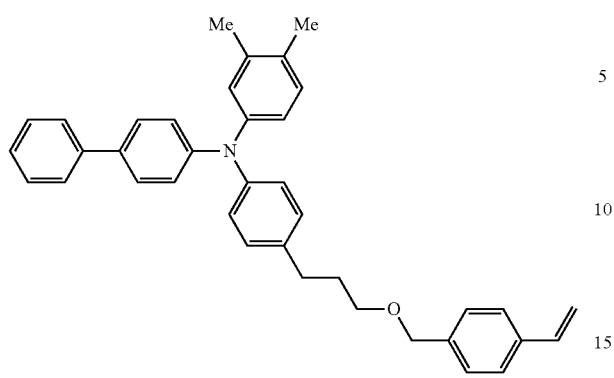

Figure 17:
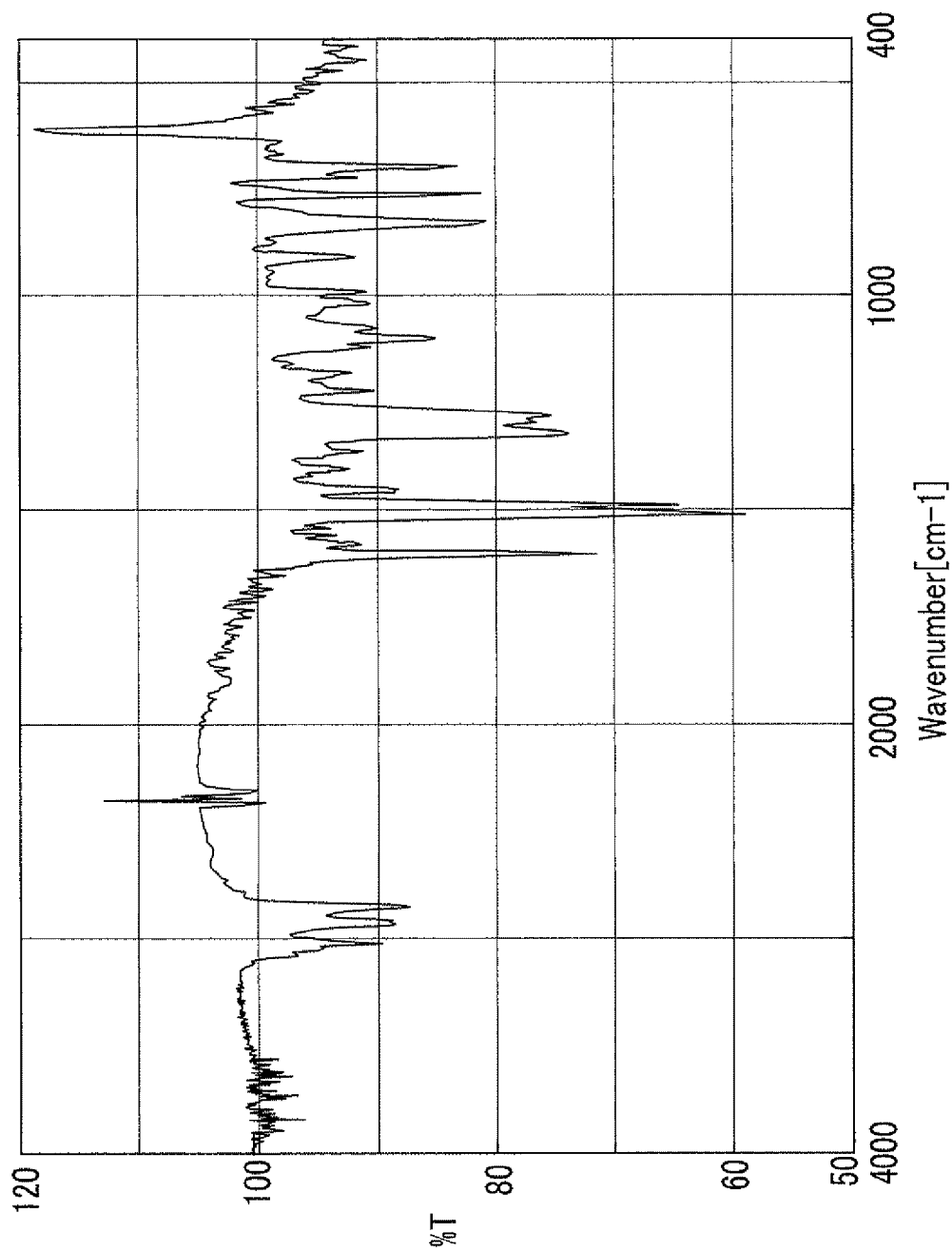
FIG. 17 is an IR spectrum of a compound (I)-62.

To a 500 ml flask, 50 g of the above compound (5), 19 g of t-butoxy potassium, 300 ml of tetrahydrofuran, and 0.2 g of nitrobenzene are added. While this mixture is stirred under a nitrogen gas flow, a solution obtained by dissolving 33 g of 4-chloromethyl styrene in 100 ml of tetrahydrofuran is slowly added dropwise thereto. After the completion of dropwise addition, the resultant is heated and refluxed for 4 hours, followed by cooling, poured into water, and extracted with toluene. After the toluene layer is sufficiently washed with water, followed by concentration, the obtained oily substance is purified by silica gel column chromatography, and then the substance is recrystallized from hexane, thereby obtaining 40 g of colorless crystalline (I)-62. The IR spectrum of the obtained compound (I)-62 is shown in FIG. 17.

Synthesis Example 6

Synthesis of Compound (I)-63

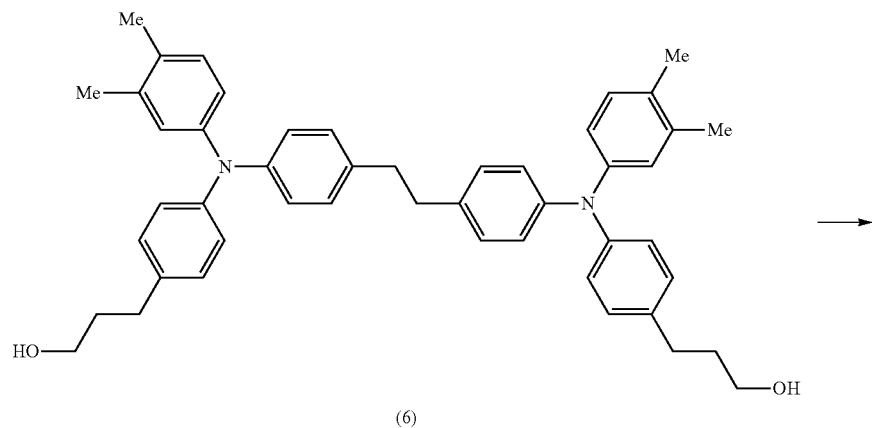

(6)

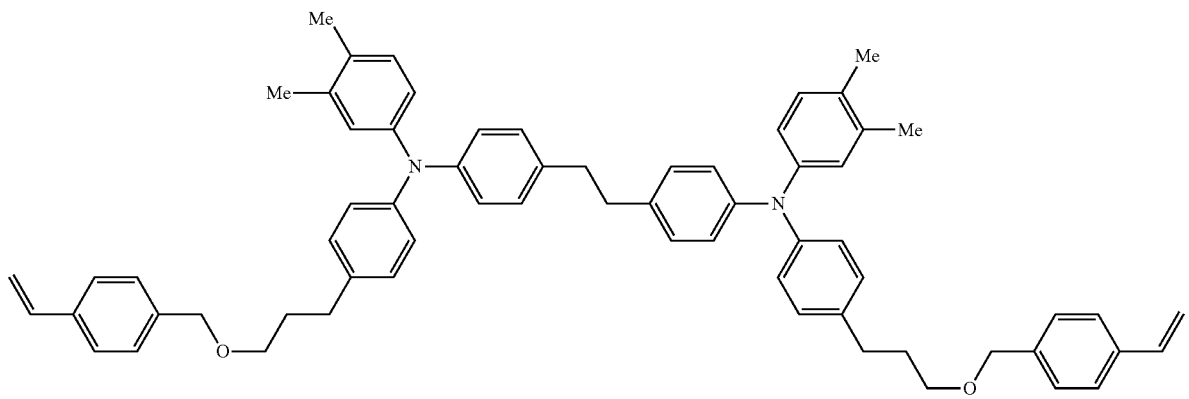

Figure 18:
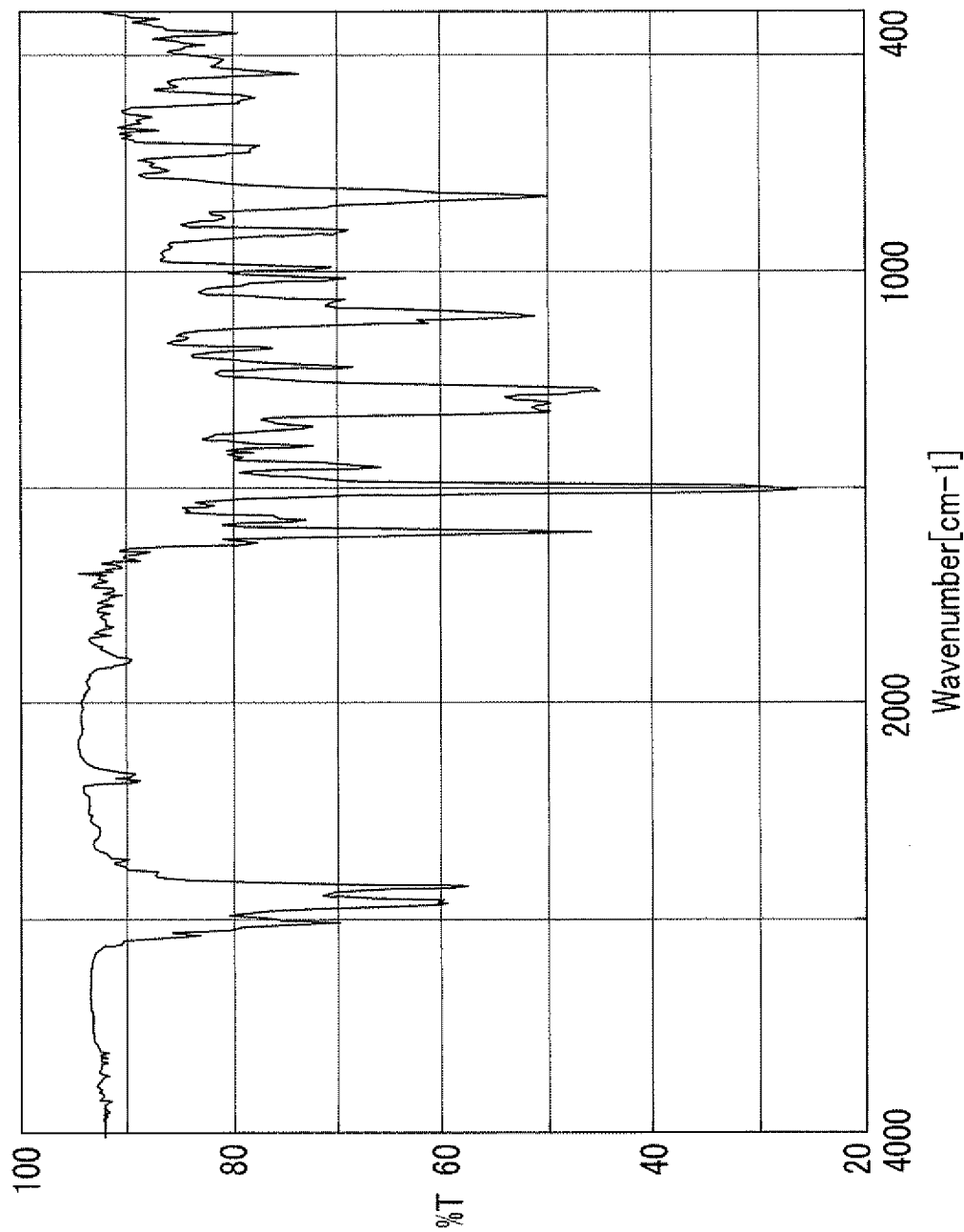
FIG. 18 is an IR spectrum of a compound (I)-63.

To a 1000 ml flask, 120 g of the above compound (6), 48 g of t-butoxy potassium, 500 ml of tetrahydrofuran, and 0.2 g of nitrobenzene are added. While this mixture is stirred under a nitrogen gas flow, a solution obtained by dissolving 100 g of 4-chloromethyl styrene in 150 ml of tetrahydrofuran is slowly added dropwise thereto. After the completion of dropwise addition, the resultant is heated and refluxed for 4 hours, followed by cooling, poured into water, and extracted with toluene. After the toluene layer is sufficiently washed with water, followed by concentration, the obtained oily substance is purified by silica gel column chromatography, and then the substance is recrystallized with ethyl acetate, thereby obtaining 45 g of colorless crystalline (I)-63. The IR spectrum of the obtained compound (I)-63 is shown in FIG. 18.

Synthesis Example 7

Synthesis of Compound (I)-64

Figure 19:
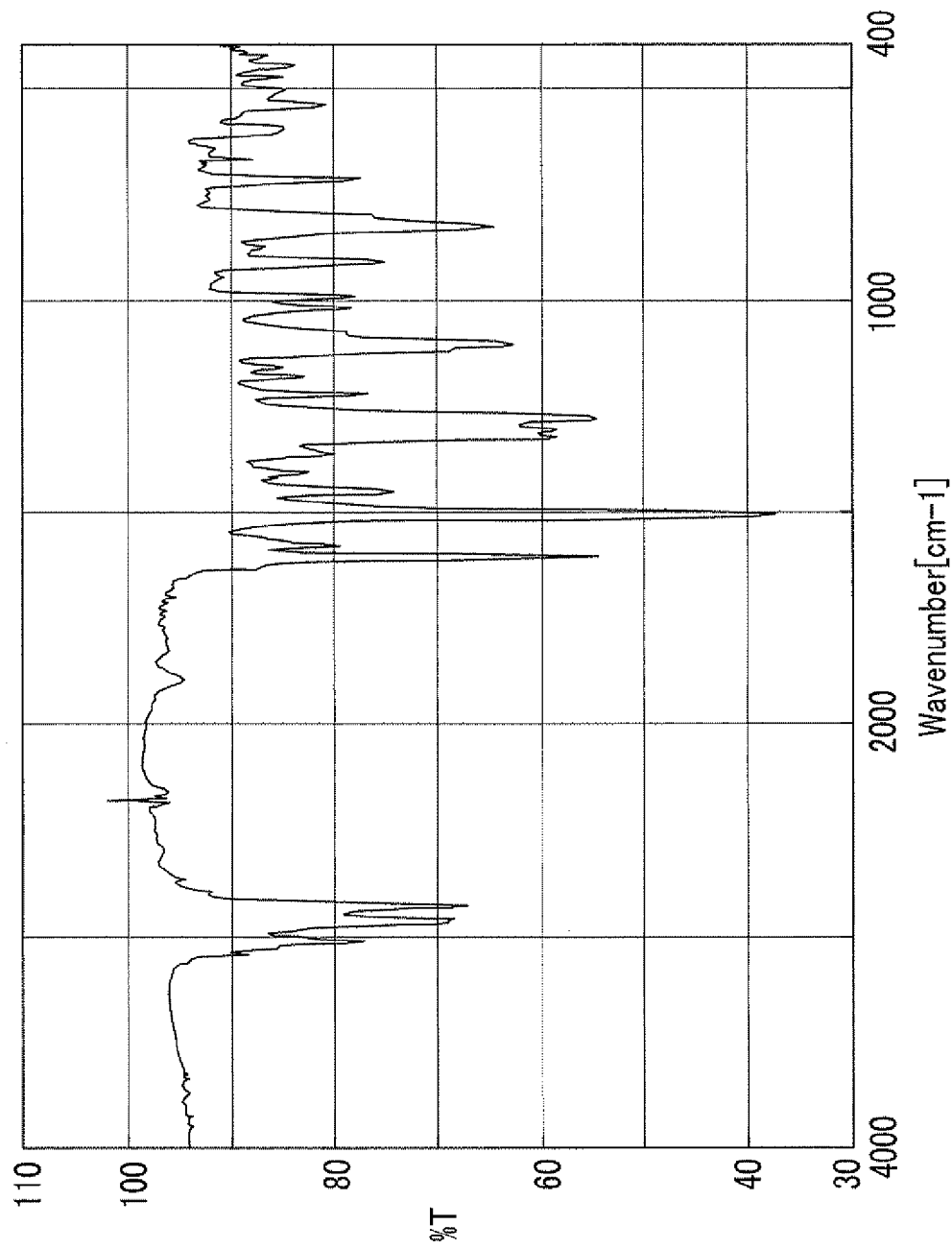
FIG. 19 is an IR spectrum of a compound (I)-64.

To a 500 ml flask, 50 g of the above compound (2), 20 g of t-butoxy potassium, 300 ml of tetrahydrofuran, and 0.2 g of nitrobenzene are added. While this mixture is stirred under a nitrogen gas flow, a solution obtained by dissolving 45 g of a mixture (manufactured by ABC SEIMI CHEMICAL Co., LTD.: CMS-P) in which 3-chloromethyl styrene and 4-chloromethyl styrene are mixed at a ratio of about 1:1 in 100 ml of tetrahydrofuran is slowly added dropwise thereto. After the completion of dropwise addition, the resultant is heated and refluxed for 4 hours, followed by cooling, poured into water, and extracted with toluene. After the toluene layer is sufficiently washed with water, followed by concentration, the obtained oily substance is purified by silica gel column chromatography, thereby obtaining 43 g of oily (I)-64. The IR spectrum of the obtained compound (I)-64 is shown in FIG. 19.

By using the m-isomer or a mixture of m-/p-isomer, the crystallization is decreased, whereby a film that exhibits excellent solubility in a solvent and uniformity is easily obtained.

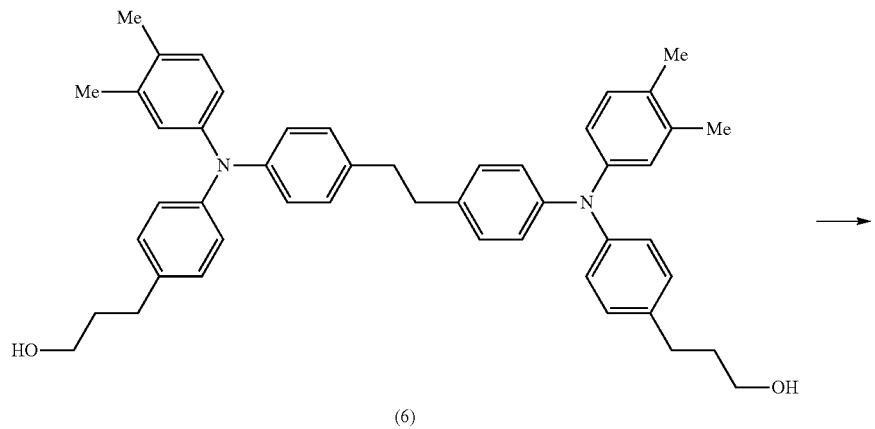

(6)

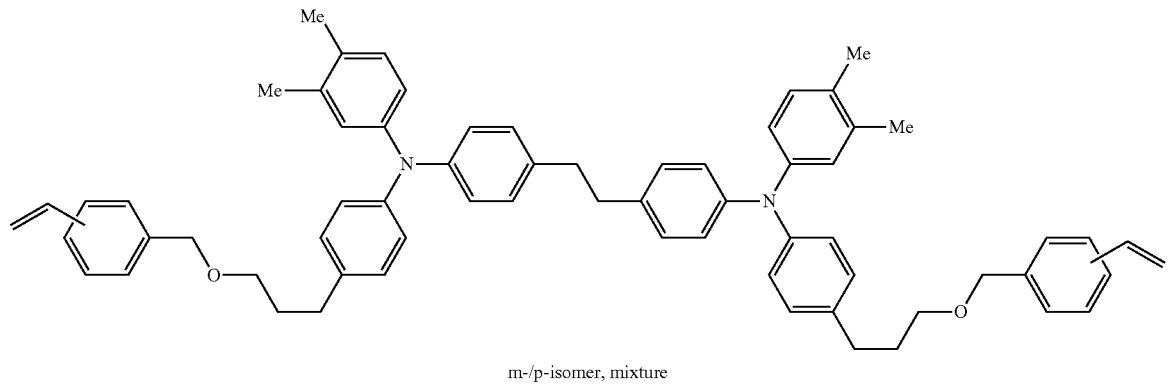

m-/p-isomer, mixture

Comparative Synthesis Example-1

Compound Disclosed in Japanese Patent No. 2546739: Synthesis of Compound E

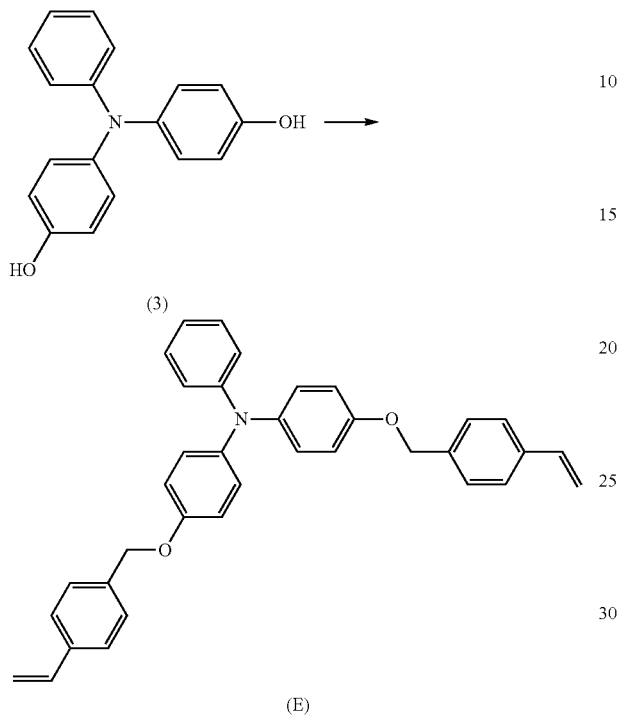

Figure 9:
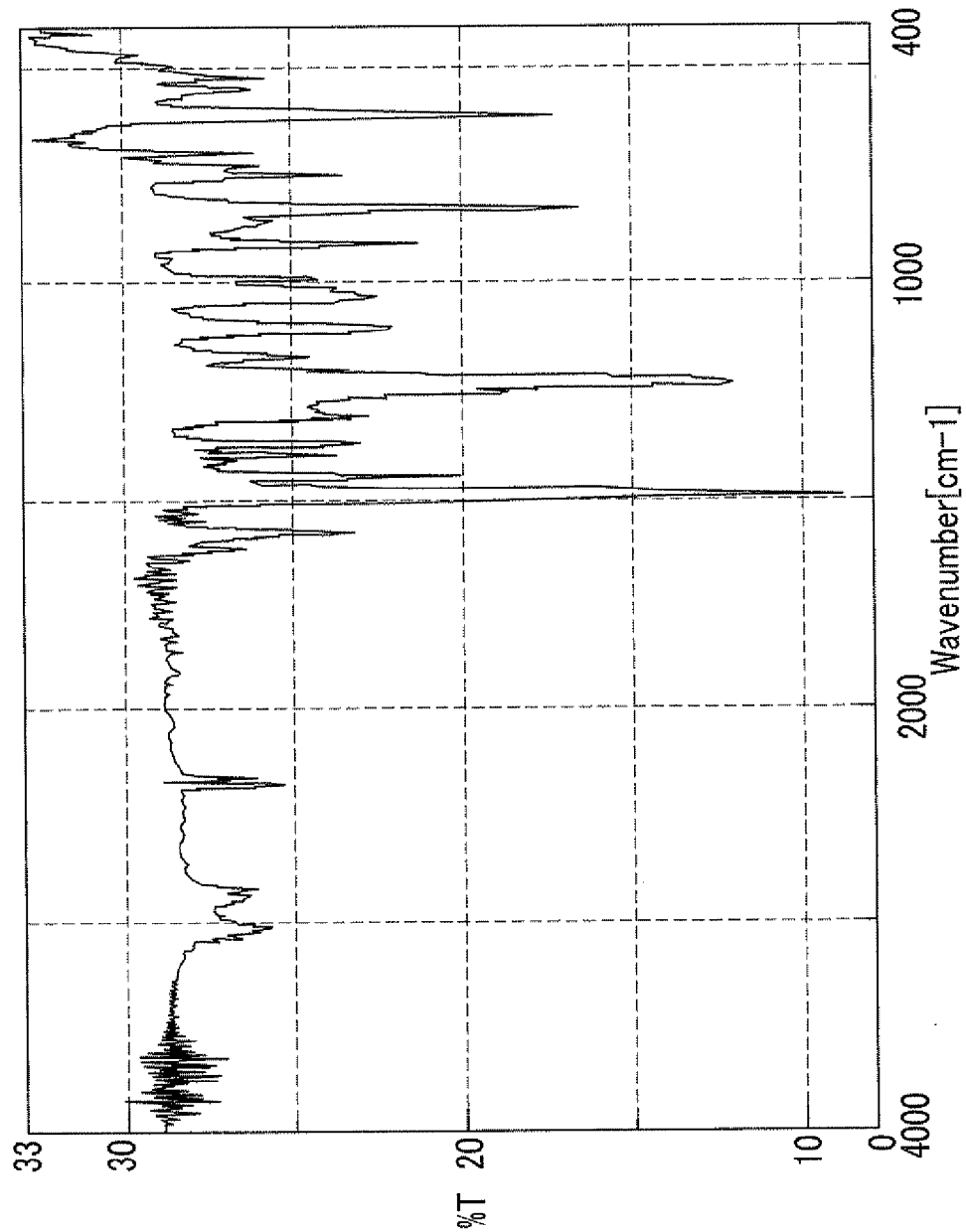
FIG. 9 is an IR spectrum of a comparative compound F.

To a 500 ml flask, 14 g of the above compound (3), 150 ml of N,N-dimethylformamide, 6.9 g of sodium hydride (about 60%), and 0.2 g of nitrobenzene are added. While this mixture is stirred under a nitrogen gas flow, a solution obtained by dissolving 18.5 g of 4-chloromethylstyrene in 100 ml of N,N-dimethylformamide is slowly added dropwise thereto. After the completion of the dropwise addition, the resultant is reacted for 3 hours at room temperature, poured into water, and extracted with toluene. The toluene layer is sufficiently washed with water, followed by concentration, and the obtained oily substance is purified by silica gel column chromatography. In addition, the purified resultant is recrystallized from a mixed solvent of toluene and hexane, thereby obtaining 22 g of a colorless crystalline compound E. The IR spectrum of the obtained Compound E is shown in FIG. 9.

The materials used for examples and comparative examples are shown below.

<Particles>
Colloidal silica (product name: PL-1, manufactured by FUSO CHEMICAL CO., LTD.)
Titanium oxide (tItone R-1T, manufactured by SAKAI CHEMICAL INDUSTRY CO., LTD)
PTFE (product name: Lubron L-2, manufactured by DAIKIN INDUSTRIES, LTD.)

<Polymers (c) and (d)>
Bispenol (Z) polycarbonate ((PC (Z), molecular weight of 40000, manufactured by MITSUBISHI GAS CHEMICAL COMPANY, INC.): polymer (c) unreactive with specific charge transport material (a))
Polymethyl methacrylate (PMMA, molecular weight of 20000): polymer (c) unreactive with specific charge transport material (a))
Polycarbonate having a carbon-carbon double bond disclosed in JP-A-5-323630 (R-resin, molecular weight of 20000): polymer (d) reacting with specific charge transport material (a)

<Curing Catalyst>
Azoisobutyronitrile (AIBN, manufactured by Otsuka Chemical Co., Ltd.)
Perbutyl C (PBC, manufactured by NOF CORPORATION)
$OT_{AZO}$-15 (OTA, manufactured by Otsuka Chemical Co., Ltd.)

<Monomer Reacting with Specific Charge Transport Material (a) and not Having Charge Transport Property: Curing Agent>
Isobutyl acrylate (IBA, manufactured by Wako Pure Chemical Industries, Ltd.)
Ethoxylated bisphenol diacrylate (ABE-300, manufactured by Shin-Nakamura Chemical Co., Ltd.)
Trimethylolpropane triacrylate (THE330, manufactured by NIPPON KAYAKU Co., Ltd.)

Example 1

Formation of Undercoat Layer 100 parts by mass of zinc oxide (average particle size of 70 nm: manufactured by TAYCA: specific surface area of 15 $m^2/g$) is mixed with 500 parts by mass of tetrahydrofuran under stirring, and 1.3 parts by mass of a silane coupling agent (KBM503: manufactured by Shin-Etsu Chemical Co., Ltd.) is added thereto, followed by stirring for 2 hours. Thereafter, toluene is distilled away through distillation under reduced pressure, and the resultant is baked at 102° C. for 3 hours, thereby obtaining zinc oxide surface-treated with the silane coupling agent.

110 parts by mass of the surface-treated zinc oxide is mixed with 500 parts by mass of tetrahydrofuran under stirring, and a solution obtained by dissolving 1.0 part by mass of a purpurin derivative in 50 parts by mass of tetrahydrofuran is added thereto, followed by stirring at 50° C. for 5 hours. Thereafter, the purpurin derivative-imparted zinc oxide is filtered by filtration under reduced pressure, followed by drying under reduced pressure at 60° C., thereby obtaining the purpurin derivative-imparted zinc oxide.

38 parts by mass of a liquid obtained by mixing 60 parts by mass of the purpurin derivative-imparted zinc oxide, 13.5 parts by mass of a curing agent (blocked isocyanate Sumidur 3175, manufactured by Sumika Bayer Urethane Co., Ltd.), and 15 parts by mass of a butyral resin (S-LEK BM-1, manufactured by SEKISUI CHEMICAL CO., LTD.) with 85 parts by mass of methyl ethyl ketone is mixed with 25 parts by mass of methyl ethyl ketone, and the resultant is dispersed with a sand mill for 2 hours by using glass beads having diameter of 1 mmφ, thereby obtaining a dispersion.

To the obtained dispersion, 0.005 part by mass of dioctyltin dilaurate and 40 parts by mass of silicone resin particles (Tospearl 145, manufactured by GE Toshiba Silicones, Co., Ltd.) are added as a catalyst, thereby obtaining a coating liquid for forming an undercoat layer. This coating liquid is coated onto an aluminum substrate having a diameter of 30 mm, a length of 340 mm, and a thickness of 1 mm by dip coating, followed by drying and curing at 170° C. for 40 minutes, thereby obtaining an undercoat layer having a thickness of 18 μm.

(Formation of Charge Generating Layer)
A mixture including 15 parts by mass of hydroxy gallium phthalocyanine as a charge generating material in which the Bragg angle (2±0.2°) of an X-ray diffraction spectrum using X-rays having CuKα characteristics has diffraction peaks at positions of at least 7.3°, 16.0°, 24.9°, and 28.0°, 10 parts by mass of a vinyl chloride-vinyl acetate copolymer resin (VMCH, manufactured by Nippon Unicar Co., Ltd.) as a binder resin, and 200 parts by mass of n-butyl acetate is dispersed with a sand mill for 4 hours by using glass beads having a diameter of 1 mmφ. To the obtained dispersion, 175 parts by mass of n-butyl acetate and 180 parts by mass of methyl ethyl ketone are added, followed by stirring, thereby obtaining a coating liquid for forming a charge generating layer. This coating liquid for forming a charge generating layer is coated by dip-coating onto the undercoat layer, followed by drying at room temperature (25° C.), thereby forming a charge generating layer having a film thickness of 0.2 p.m.

(Formation of Charge Transporting Layer)

45 parts by mass of N,N'-diphenyl-N,N'-bis(3-methylphenyl)-[1,1']biphenyl-4,4'-diamine and 55 parts by mass of a bisphenol Z polycarbonate resin (viscosity average molecular weight: 50000) are added to 800 parts by mass of chlorobenzene, followed by dissolving, thereby obtaining a coating liquid for forming a charge transporting layer. This coating liquid is coated onto the charge generating layer, followed by drying at 130° C. for 45 minutes, thereby forming a charge transporting layer (charge transporting layer 1) having a film thickness of 15 μm.

(Formation of Protective Layer)

30 parts by mass of a charge transport material ((I)-48), 0.2 part by mass of colloidal silica (product name: PL-1, manufactured by FUSO CHEMICAL CO., LTD.), 15 parts by mass of cyclopentanol, 15 parts by mass of cyclopentyl methyl ether, 0.1 part by mass of 3,5-di-t-butyl-4-hydroxytoluene (BHT), and 0.2 part by mass of azoisobutyronitrile (AIBN) are mixed, thereby preparing a coating liquid for forming a protective layer. This coating liquid is coated onto the charge transporting layer by spray coating, followed by air drying at room temperature for 30 minutes. Thereafter, the resultant is heated up to 150° C. from room temperature for 30 minutes under a nitrogen gas flow having an oxygen concentration of 200 ppm or less, and then cured by being heated again at 150° C. for 30 minutes, thereby forming a protective layer having a film thickness of 5 μm. During the coating, drying, and curing of the protective layer, the charge transporting layer is not dissolved, the materials forming the protective layer are not separated, and a uniform protective layer is obtained.

In the above-described manner, an electrophotographic photoreceptor is obtained. This photoreceptor is named a photoreceptor 1.

The configurations of the surface layer of the photoreceptors prepared in examples and comparative examples are organized in Table 3.

TABLE 3

| Photo-receptor | Charge transporting layer | | Surface layer | | | | | |
|---|---|---|---|---|---|---|---|---|
| | Number | Film thickness (μm) | Charge transport material (a) | | Unsaturated bond-containing compound | | Additive | |
| Photo-receptor-1 | Charge transporting layer 1 | 15 | (I)-48 | 30 parts by mass | — | — | PL-1 | 0.2 part by mass |
| Photo-receptor-2 | Charge transporting layer 1 | 15 | (I)-48 | 30 parts by mass | — | — | PL-1 | 0.2 part by mass |
| Photo-receptor-3 | Charge transporting layer 1 | 15 | (I)-52 | 30 parts by mass | — | — | PL-1 | 0.2 part by mass |
| Photo-receptor-4 | Charge transporting layer 1 | 15 | (I)-58 | 30 parts by mass | — | — | PL-1 | 0.2 part by mass |
| Photo-receptor-5 | Charge transporting layer 1 | 15 | (I)-60 | 30 parts by mass | — | — | — | 0.2 part by mass |
| Photo-receptor-6 | Charge transporting layer 1 | 15 | (I)-15 | 30 parts by mass | — | — | PL-1 | 0.2 part by mass |
| Photo-receptor-7 | Charge transporting layer 1 | 15 | (I)-16 | 30 parts by mass | — | — | Lubron L2 | 2 parts by mass |
| Photo-receptor-8 | Charge transporting layer 1 | 15 | (I)-23 | 30 parts by mass | — | — | Lubron L2 | 2 parts by mass |
| Photo-receptor-9 | Charge transporting layer 1 | 15 | (I)-26 | 30 parts by mass | — | — | Lubron L2 | 2 parts by mass |
| Photo-receptor-10 | Charge transporting layer 1 | 15 | (I)-28 | 30 parts by mass | — | — | Lubron L2 | 2 parts by mass |
| Photo-receptor-11 | Charge transporting layer 1 | 15 | (I)-34 | 30 parts by mass | — | — | Lubron L2 | 2 parts by mass |
| Photo-receptor-12 | Charge transporting layer 1 | 15 | (I)-39 | 30 parts by mass | — | — | Lubron L2 | 5 parts by mass |

TABLE 3-continued

| | | | | | | | | |
|---|---|---|---|---|---|---|---|---|
| Photo-receptor-13 | Charge transporting layer 1 | 15 | (I)-52 (I)-3 | 20 parts by mass 10 parts by mass | — | — | PL-1 | 0.4 part by mass |
| Photo-receptor-14 | Charge transporting layer 1 | 15 | (I)-60 (I)-7 | 20 parts by mass 10 parts by mass | — | — | PL-1 | 0.4 part by mass |
| Photo-receptor-15 | Charge transporting layer 1 | 15 | (I)-58 (I)-9 | 20 parts by mass 10 parts by mass | — | — | PL-1 | 0.4 part by mass |
| Photo-receptor-16 | Charge transporting layer 1 | 15 | (I)-58 (I)-26 | 20 parts by mass 10 parts by mass | — | — | Lubron L2 | 5 parts by mass |
| Photo-receptor-17 | Charge transporting layer 2 | 15 | (I)-48 | 30 parts by mass | — | — | PL-1 | 0.2 part by mass |
| Photo-receptor-18 | Charge transporting layer 2 | 15 | (I)-48 | 30 parts by mass | — | — | PL-1 | 0.2 part by mass |
| Photo-receptor-19 | Charge transporting layer 2 | 15 | (I)-52 | 30 parts by mass | — | — | PL-1 | 0.2 part by mass |
| Photo-receptor-20 | Charge transporting layer 2 | 15 | (I)-58 | 30 parts by mass | — | — | PL-1 | 0.2 part by mass |
| Photo-receptor-21 | Charge transporting layer 2 | 15 | (I)-60 | 30 parts by mass | — | — | PL-1 | 0.2 part by mass |
| Photo-receptor-22 | Charge transporting layer 2 | 15 | (I)-15 | 30 parts by mass | — | — | PL-1 | 0.2 part by mass |
| Photo-receptor-23 | Charge transporting layer 2 | 15 | (I)-16 | 30 parts by mass | — | — | Lubron L2 | 2 part by mass |
| Photo-receptor-24 | Charge transporting layer 2 | 15 | (I)-23 | 30 parts by mass | — | — | Lubron L2 | 2 part by mass |
| Photo-receptor-25 | Charge transporting layer 2 | 15 | (I)-26 | 30 parts by mass | — | — | Lubron L2 | 2 part by mass |
| Photo-receptor-26 | Charge transporting layer 3 | 17 | (I)-48 | 30 parts by mass | — | — | PL-1 | 0.2 part by mass |
| Photo-receptor-27 | Charge transporting layer 4 | 15 | (I)-48 | 30 parts by mass | — | — | PL-1 | 0.2 part by mass |
| Photo-receptor-28 | Charge transporting layer 5 | 15 | (I)-48 | 30 parts by mass | — | — | PL-1 | 0.2 part by mass |
| Photo-receptor-29 | — | — | (I)-52 | 30 parts by mass | — | — | Compound (b) | 10 parts by mass |
| Photo-receptor-30 | — | — | (I)-52 | 30 parts by mass | — | — | Compound (c) PC(Z) | 10 parts by mass 5 parts by mass |
| Photo-receptor-31 | Charge transporting layer 1 | 15 | (I)-52 | 30 parts by mass | — | — | — | 0.2 part by mass |
| Photo-receptor-32 | Charge transporting layer 1 | 15 | (I)-52 | 30 parts by mass | — | — | — | 0.2 part by mass |
| Photo-receptor-33 | Charge transporting layer 1 | 15 | (I)-52 | 30 parts by mass | Reactive polymer (d) | 10 parts by mass | PL-1 | 0.2 part by mass |
| Photo-receptor-34 | Charge transporting layer 1 | 15 | (I)-52 | 30 parts by mass | THE330 | 10 parts by mass | PL-1 | 0.2 part by mass |
| Photo-receptor-35 | Charge transporting layer 1 | 15 | (I)-52 | 30 parts by mass | ABE-300 | 10 parts by mass | R-1T | 0.2 part by mass |
| Photo-receptor-36 | Charge transporting layer 1 | 15 | (I)-58 | 30 parts by mass | ABE-300 | 10 parts by mass | R-1T | 0.2 part by mass |
| Photo-receptor-37 | Charge transporting layer 1 | 15 | (I)-58 (I)-61 | 20 parts by weight 10 parts by weight | — | — | PL-1 | 0.4 part by mass |

TABLE 3-continued

| | | | | | | | | |
|---|---|---|---|---|---|---|---|---|
| Photo-receptor-38 | Charge transporting layer 1 | 15 | (I)-52 (I)-62 | 20 parts by weight 10 parts by weight | — | — | Lubron L2 | 5 parts by mass |
| Photo-receptor-39 | Charge transporting layer 1 | 15 | (I)-52 (I)-63 | 10 parts by weight 20 parts by weight | — | — | Lubron L2 | 5-parts by mass |
| Photo-receptor-40 | Charge transporting layer 1 | 15 | (I)-63 | 30 parts by weight | — | — | PL-1 | 5 parts by mass |
| Comparative photo-receptor-1 | Charge transporting layer 1 | | Compound (E) | 30 parts by mass | — | — | PL-1 | 0.2 part by mass |
| Comparative photo-receptor-2 | Charge transporting layer 1 | | Compound (F) | 30 parts by mass | — | — | PL-1 | 0.2 part by mass |
| Comparative photo-receptor-3 | Charge transporting layer 1 | | Compound (G) | 30 parts by mass | — | — | PL-1 | 0.2 part by mass |
| Comparative photo-receptor-4 | — | | Compound (E) | 30 parts by mass | — | — | Compound (b) | 10 parts by mass |
| Comparative photo-receptor-5 | — | | Compound (F) | 30 parts by mass | — | — | Compound (b) | 10 parts by mass |
| Comparative photo-receptor-6 | — | | Compound (G) | 30 parts by mass | — | — | Compound (b) | 10 parts by mass |
| Comparative photo-receptor-7 | Charge transporting layer 1 | | — | — | — | — | — | — |
| Comparative photo-receptor-8 | Charge transporting layer 1 | | Compound (H) | 30 parts by mass | — | — | PL-1 | 0.2 part by mass |
| Comparative photo-receptor-9 | Charge transporting layer 1 | | Compound (I) | 30 parts by mass | — | — | PL-1 | 0.2 part by mass |

| | | Surface layer | | | |
|---|---|---|---|---|---|
| Photo-receptor | Additive | | Polymerization initiator | | Film thickness of surface layer (μm) | Curing method |
| Photo-receptor-1 | BHT | 0.1 part by mass | AIBN | 0.2 part by mass | 5 | Thermal curing |
| Photo-receptor-2 | BHT | 0.1 part by mass | OTA | 0.2 part by mass | 5 | Thermal curing |
| Photo-receptor-3 | BHT | 0.1 part by mass | OTA | 0.2 part by mass | 5 | Thermal curing |
| Photo-receptor-4 | BHT | 0.1 part by mass | OTA | 0.2 part by mass | 5 | Thermal curing |
| Photo-receptor-5 | BHT | 0.1 part by mass | AIBN | 0.2 part by mass | 5 | Thermal curing |
| Photo-receptor-6 | BHT | 0.1 part by mass | AIBN | 0.2 part by mass | 7 | Thermal curing |
| Photo-receptor-7 | BHT | 0.1 part by mass | PBC | 0.2 part by mass | 7 | Thermal curing |
| Photo-receptor-8 | BHT | 0.1 part by mass | PBC | 0.2 part by mass | 7 | Thermal curing |
| Photo-receptor-9 | BHT | 0.1 part by mass | PBC | 0.2 part by mass | 7 | Thermal curing |
| Photo-receptor-10 | BHT | 0.1 part by mass | OTA | 0.2 part by mass | 7 | Thermal curing |
| Photo-receptor-11 | — | — | OTA | 0.2 part by mass | 5 | Thermal curing |
| Photo-receptor-12 | BHT | 0.1 part by mass | OTA | 0.2 part by mass | 5 | Thermal curing |
| Photo-receptor-13 | BHT | 0.1 part by mass | OTA | 0.2 part by mass | 8 | Thermal curing |
| Photo-receptor-14 | BHT | 0.1 part by mass | OTA | 0.2 part by mass | 8 | Thermal curing |
| Photo-receptor-15 | BHT | 0.1 part by mass | OTA | 0.2 part by mass | 8 | Thermal curing |
| Photo-receptor-16 | BHT | 0.1 part by mass | OTA | 0.2 part by mass | 8 | Thermal curing |
| Photo-receptor-17 | BHT | 0.1 part by mass | AIBN | 0.2 part by mass | 5 | Thermal curing |

TABLE 3-continued

| | | | | | | |
|---|---|---|---|---|---|---|
| Photoreceptor-18 | BHT | 0.1 part by mass | OTA | 0.2 part by mass | 5 | Thermal curing |
| Photoreceptor-19 | BHT | 0.1 part by mass | OTA | 0.2 part by mass | 5 | Thermal curing |
| Photoreceptor-20 | BHT | 0.1 part by mass | OTA | 0.2 part by mass | 5 | Thermal curing |
| Photoreceptor-21 | BHT | 0.1 part by mass | AIBN | 0.2 part by mass | 3 | Thermal curing |
| Photoreceptor-22 | BHT | 0.1 part by mass | AIBN | 0.2 part by mass | 7 | Thermal curing |
| Photoreceptor-23 | BHT | 0.1 part by mass | PBC | 0.2 part by mass | 7 | Thermal curing |
| Photoreceptor-24 | BHT | 0.1 part by mass | PBC | 0.2 part by mass | 7 | Thermal curing |
| Photoreceptor-25 | BHT | 0.1 part by mass | PBC | 0.2 part by mass | 7 | Thermal curing |
| Photoreceptor-26 | BHT | 0.1 part by mass | AIBN | 0.2 part by mass | 5 | Thermal curing |
| Photoreceptor-27 | BHT | 0.1 part by mass | AIBN | 0.2 part by mass | 5 | Thermal curing |
| Photoreceptor-28 | BHT | 0.1 part by mass | AIBN | 0.2 part by mass | 5 | Thermal curing |
| Photoreceptor-29 | BHT | 0.1 part by mass | OTA | 0.2 part by mass | 20 | Thermal curing |
| Photoreceptor-30 | BHT | 0.1 part by mass | AIBN | 0.2 part by mass | 20 | Thermal curing |
| Photoreceptor-31 | BHT | 0.1 part by mass | Irgacure 184 | 0.2 part by mass | 4 | Photocuring |
| Photoreceptor-32 | BHT | 0.1 part by mass | — | — | 4 | Electron beam curing |
| Photoreceptor-33 | BHT | 0.1 part by mass | — | — | 4 | Electron beam curing |
| Photoreceptor-34 | BHT | 0.1 part by mass | — | — | 4 | Electron beam curing |
| Photoreceptor-35 | BHT | 0.1 part by mass | — | — | 4 | Electron beam curing |
| Photoreceptor-36 | BHT | 0.1 part by mass | — | — | 4 | Electron beam curing |
| Photoreceptor-37 | BHT | 0.1 part by mass | OTA | 0.2 part by mass | 8 | Thermal curing |
| Photoreceptor-38 | BHT | 0.1 part by mass | OTA | 0.2 part by mass | 8 | Thermal curing |
| Photoreceptor-39 | BHT | 0.1 part by mass | OTA | 0.2 part by mass | 8 | Thermal curing |
| Photoreceptor-40 | BHT | 0.1 part by mass | OTA | 0.2 part by mass | 8 | Thermal curing |
| Comparative photoreceptor-1 | BHT | 0.1 part by mass | AIBN | 0.2 part by mass | Not obtained | Thermal curing |
| Comparative photoreceptor-2 | BHT | 0.1 part by mass | AIBN | 0.2 part by mass | 5 | Thermal curing |
| Comparative photoreceptor-3 | BHT | 0.1 part by mass | AIBN | 0.2 part by mass | 5 | Thermal curing |
| Comparative photoreceptor-4 | BHT | 0.1 part by mass | OTA | 0.2 part by mass | 20 | Thermal curing |
| Comparative photoreceptor-5 | BHT | 0.1 part by mass | OTA | 0.2 part by mass | 20 | Thermal curing |
| Comparative photoreceptor-6 | BHT | 0.1 part by mass | OTA | 0.2 part by mass | 20 | Thermal curing |
| Comparative photoreceptor-7 | — | — | — | — | — | — |
| Comparative photoreceptor-8 | BHT | 0.1 part by mass | AIBN | 0.2 part by mass | 5 | Thermal curing |
| Comparative photoreceptor-9 | BHT | 0.1 part by mass | AIBN | 0.2 part by mass | 5 | Thermal curing |

[Evaluation]
—Image Quality Evaluation—

Electrophotographic photoreceptors prepared in the above manner are mounted on a DocuCentre Color 400CP manufactured by Fuji Xerox Co., Ltd., and the following evaluations are consecutively performed at a low temperature and low humidity (8° C., 20% RH) and a high temperature and high humidity (28° C., 85% RH).

That is, first, 3000 sheets of image formation tests are produced in a low temperature and low humidity (8° C., 20% RH) environment, and the quality of the image of the 3000$^{th}$ sheet and the quality of an image obtained firstly after the image forming apparatus has been left for 24 hours in the low temperature and low humidity (8° C., 20% RH) environment after the 3000 sheets of image formation tests are produced are evaluated in terms of the following image quality uniformity, fogging, streaks, and image deletion.

The evaluation results are shown in Table 4.

Subsequently, after the image forming test and image quality evaluation in the low temperature low humidity environment, 3000 sheets of image forming tests are produced in a high temperature and high humidity (28° C., 85% RH) environment. Moreover, the quality of the image of the 3000$^{th}$ sheet and the quality of an image obtained firstly after the image forming apparatus has been left for 24 hours in the high temperature and high humidity (28° C., 85% RH) environment after the 3000 sheets of image formation tests are produced are evaluated in terms of the following image quality uniformity, fogging, streaks, and image deletion.

The evaluation results are shown in Table 5.

For the image forming test, P paper (A4 size, fed in the transverse direction) manufactured by Fuji Xerox Co., Ltd. is used, and for the 3000 sheets of image forming tests, images created by dividing A4 paper into cyan, magenta, yellow, and black in the transverse direction is used.

<Evaluation of Image Quality Uniformity>

Figure 6:
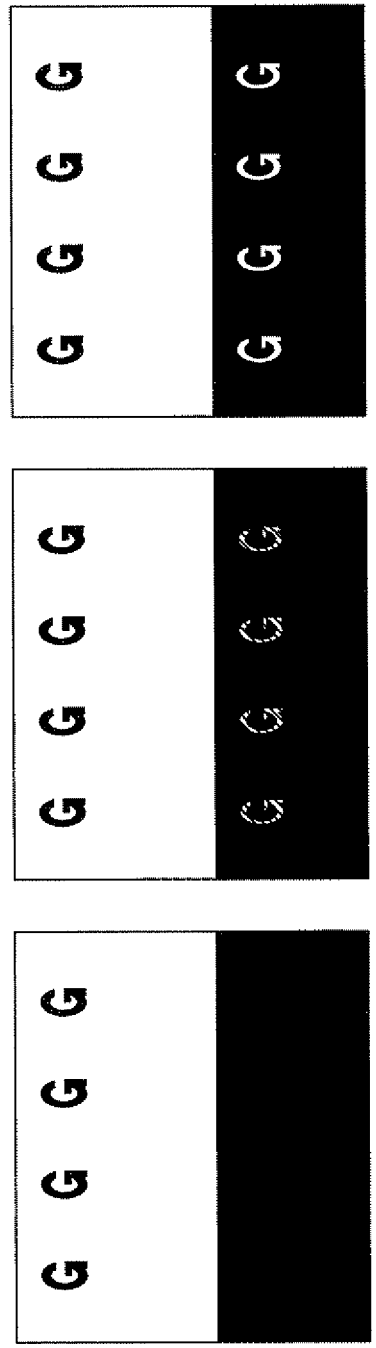
FIGS. 6A to 6C are views showing image patterns used for image evaluation.

For evaluating the image quality uniformity, a chart of a pattern including characters and a black area (image density of 30%), which is shown in FIG. 6A, is printed, and density variation in the black area portion having a density of 30% is visually observed and evaluated.

A: Density variation is excellent or minor.
B: Density variation is slightly noticeable.
C: Density variation is clearly observed.

<Evaluation of Fogging>

For judging fogging, the same sample as that used for the evaluation of image quality uniformity described above is used, and the degree in which the toner is attached to a white portion of the paper is visually observed.

A: Excellent
B: Slight fogging is observed
C: Fogging causing a problem in image quality is observed <Evaluation of Streaks>

Streaks are visually observed and judged by using the same sample as that used for the evaluation of image quality uniformity described above.

A: Excellent
B: Streaks are observed partially.
C: Streaks causing a problem in image quality are observed.

<Evaluation of Image Deletion>

Image deletion is judged by visually observing blurring of straight lines in the black area having a density of 30%, by using the same sample as that used for the evaluation of image quality uniformity described above.

A: Excellent
B: Though not problematic during consecutive printing tests, blurring occurs after the image forming apparatus is left for a day (24 hours).
C: Blurring occurs even during the consecutive printing tests.

<Evaluation of Ghost>

Ghost is evaluated by printing a chart of a pattern including characters (G) and a black area (image density of 50%), which is shown in FIG. 6A, and visually observing how the characters (G) appear in the portion of the 50% of black area.

A: Ghost is excellent or minor as shown in FIG. 6A.
B: Ghost is slightly noticeable as shown in FIG. 6B.
C: Ghost is clearly observed as shown in FIG. 6C.

—Evaluation of Protective Layer (Uppermost Surface Layer)—

The adhesiveness and abrasion loss of the protective layer (uppermost surface layer) are evaluated in the following manner.

<Evaluation of Adhesiveness of Protective Layer>

To evaluate the adhesiveness of the protective layer, 5×5 2 mm square cuts are made with a cutter knife in the photoreceptor that has performed about 6000 sheets in total of image formation tests at a low temperature and low humidity and at a high temperature and high humidity, and amending tape manufactured by 3M is attached thereto. The tape is peeled off, and the adhesiveness of the protective layer is evaluated based on the number of cuts remaining after the peeling.

It is understood that the greater the number of remaining cuts, the more excellent the adhesiveness with respect to the charge transporting layer below the protective layer.

A: 21 or more cuts remain.
B: From 11 to 20 cuts remain.
C: 10 or less cuts remain.

The evaluation results are shown in Table 4.

<Measurement of Abrasion Loss of Uppermost Surface Layer>

For measuring the abrasion loss of the uppermost surface layer, the abrasion loss of the photoreceptor that has performed about 6000 sheets in total of image formation tests at a low temperature and low humidity and at a high temperature and high humidity is measured.

It is understood that the smaller the abrasion loss, the higher the mechanical strength of the uppermost surface layer.

The evaluation results are shown in Table 4.

Examples 2 to 16

Photoreceptors 2 to 16 are prepared in the same manner as that in Example 1, except that the types and mixing amount of the specific charge transport material (a), other charge transport materials, and various additives (particles, polymers, curing agents, antioxidants, and curing catalysts) are changed according to Table 3, and the prepared photoreceptors are evaluated. The film thickness of the protective layer is adjusted to a film thickness in which appropriate potentials are obtained in DocuCentre Color 400CP.

The evaluation results are shown in Tables 4 and 5.

Examples 17 to 25

Photoreceptors 17 to 25 are prepared in the same manner as that in Example 1 to Example 9 respectively, except that the binder resin used for forming the charge transporting layer is changed to a bisphenol Z polycarbonate resin (viscosity average molecular weight: 55000) (charge transporting layer 2), and the prepared photoreceptors are evaluated in the same manner as that in Example 1. The film thickness of the protective layer is adjusted to a film thickness in which appropriate potentials are obtained in DocuCentre Color 400CP.

The evaluation results are shown in Tables 4 and 5.

Example 26

A photoreceptor 26 is prepared in the same manner as that in Example 1, except that the formation method of a charge transporting layer is changed as below, and the photoreceptor 26 is evaluated. The evaluation results are shown in Tables 4 and 5.

(Formation of Charge Transporting Layer)

45 parts by mass of a compound (a) having the following structure and 55 parts by mass of a bisphenol Z polycarbonate resin (viscosity average molecular weight: 40000) are added to 800 parts by mass of chlorobenzene, followed by dissolution, thereby obtaining a coating liquid for forming a charge transporting layer. This coating liquid is coated onto the charge generating layer, followed by drying at 130° C. for 45 minutes, thereby forming a charge transporting layer (charge transporting layer 3) having a film thickness of 17 μm.

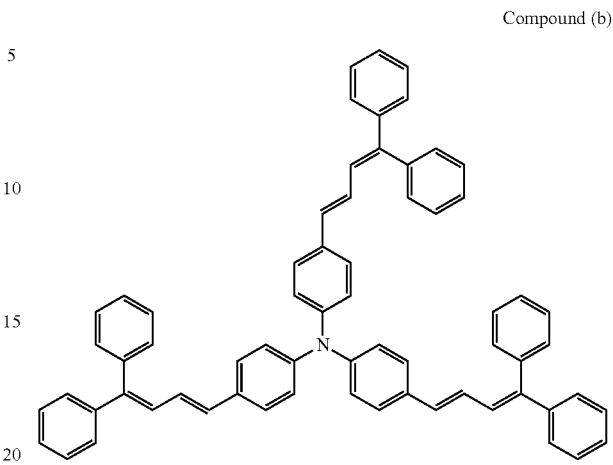

Compound (b)

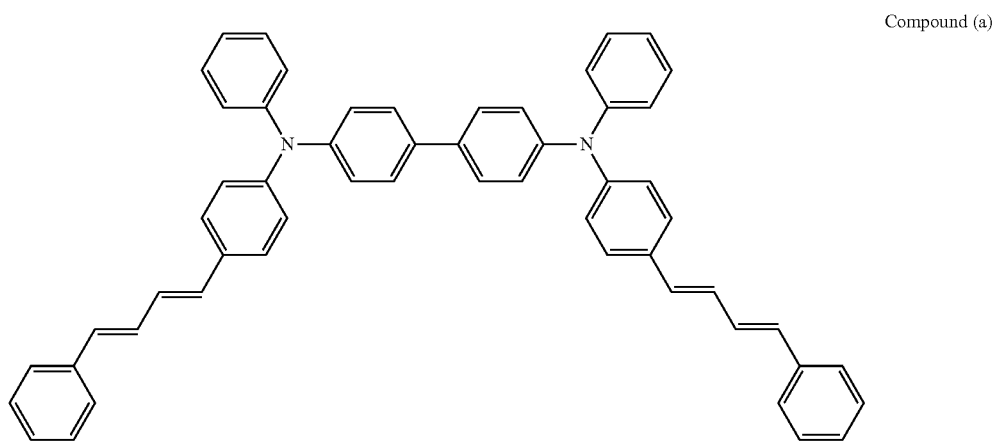 [SMILES: C(/C=C/c1ccc(N(c2ccccc2)c2ccc(-c3ccc(N(c4ccccc4)c4ccc(/C=C/C=C/c5ccccc5)cc4)cc3)cc2)cc1)=C\c1ccccc1]

Compound (a)

Example 27

A photoreceptor 27 is prepared in the same manner as that in Example 1, except that the formation method of a charge transporting layer is changed as below, and the photoreceptor 27 is evaluated. The evaluation results are shown in Table 4.

(Formation of Charge Transporting Layer)

50 parts by mass of a compound (b) having the following structure and 50 parts by mass of a bisphenol Z polycarbonate resin (viscosity average molecular weight: 50000) are added to 800 parts by mass of chlorobenzene, followed by dissolution, thereby obtaining a coating liquid for forming a charge transporting layer. This coating liquid is coated onto the charge generating layer, followed by drying at 130° C. for 45 minutes, thereby forming a charge transporting layer (charge transporting layer 4) having a film thickness of 15 μm.

Example 28

A photoreceptor 28 is prepared in the same manner as that in Example 1, except that the formation method of the charge transporting layer is changed as below, and the photoreceptor 28 is evaluated. The evaluation results are shown in Tables 4 and 5.

(Formation of Charge Transporting Layer)

50 parts by mass of a compound (c) having the following structure and 50 parts by mass of a bisphenol Z. polycarbonate resin (viscosity average molecular weight: 80000) are added to 800 parts by mass of chlorobenzene, followed by dissolution, thereby obtaining a coating liquid for forming a charge transporting layer. This coating liquid is coated onto the charge generating layer, followed by drying at 130° C. for 45 minutes, thereby forming a charge transporting layer (charge transporting layer 5) having a film thickness of 15 μm.

Compound (c)

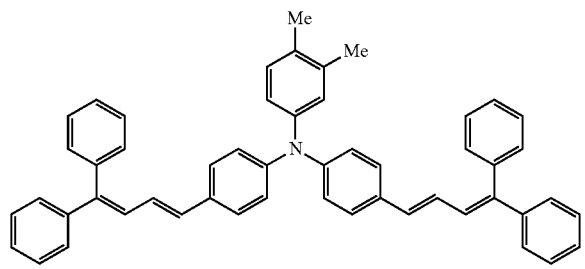

Example 29

The same manner as that in Example 1 is applied until the charge generating layer is formed. Thereafter, as an uppermost surface layer, a charge transporting layer is formed in the following manner to prepare a photoreceptor 29, and the photoreceptor 29 is evaluated in the same manner as that in Example 1. The evaluation results are shown in Tables 4 and 5.

(Formation of Charge Transporting Layer)

30 parts by mass of a charge transport material ((I)-52), 10 parts by mass of the compound (b), 30 parts by mass of toluene, 0.1 part by mass of 3,5-di-t-butyl-4-hydroxytoluene (BHT), and 0.2 part by mass of OTA are mixed, thereby preparing a coating liquid for forming a charge transporting layer. This coating liquid is coated onto the charge generating layer by dip coating, followed by air drying at room temperature for 30 minutes, and is heated up to 150° C. from room temperature for 30 minutes. The resultant is cured by being further heated at 150° C. for 30 minutes to form a charge transporting layer having a film thickness of 20 μm, thereby preparing a photoreceptor of Example 29.

Regarding the photoreceptors in which the charge transporting layer becomes the uppermost surface layer, the configuration of the charge transporting layer in Table 3 is disclosed not in the column of the charge transporting layer but in the column of the surface layer.

Example 30

The same manner as that in Example 1 is applied until the charge generating layer is formed. Thereafter, as an uppermost surface layer, a charge transporting layer is formed in the following manner to prepare a photoreceptor 30, and the photoreceptor 30 is evaluated in the same manner as that in Example 1. The evaluation results are shown in Tables 4 and 5.

(Formation of Charge Transporting Layer)

30 parts by mass of a specific charge transport material ((I)-52), 10 parts by mass of the compound (c), 5 parts by mass of PC(Z), 30 parts by mass of toluene, 0.1 part by mass of 3,5-di-t-butyl-4-hydroxytoluene (BET), and 0.2 part by mass of azoisobutyronitrile are mixed, thereby preparing a coating liquid for forming a charge transporting layer. This coating liquid is coated onto the charge generating layer by dip coating, followed by air drying at room temperature for 30 minutes, and is heated up to 150° C. from room temperature for 30 minutes in a nitrogen atmosphere having an oxygen concentration of 200 ppm or less. The resultant is cured by being further heated at 150° C. for 30 minutes to form a charge transporting layer having a film thickness of 20 μm, thereby preparing a photoreceptor of Example 30.

Example 31

The same manner as that in Example 1 is applied until the charge transporting layer is formed. Thereafter, a protective layer is formed in the following manner to prepare a photoreceptor 31, and the photoreceptor 31 is evaluated in the same manner as that in Example 1. The evaluation results are shown in Tables 4 and 5.

(Formation of Protective Layer)

30 parts by mass of a charge transport material ((I)-52), 0.2 part by mass of colloidal silica (product name: PL-1, manufactured by FUSO CHEMICAL CO., LTD.), 30 parts by mass of toluene, 0.1 part by mass of 3,5-di-t-butyl-4-hydroxytoluene (BHT), and 0.2 part by mass of Irgacure 184 (photocuring catalyst) are mixed, thereby preparing a coating liquid for forming a protective layer. This coating liquid is coated onto the charge transporting layer by spray coating, followed by air drying at room temperature for 30 minutes. Thereafter, the resultant is subjected to photopolymerization curing by being irradiated with light of a metal halide lamp in a condition of irradiation intensity: 500 mW/cm$^2$ and irradiation time: 300 seconds in a nitrogen atmosphere having an oxygen concentration of 100 ppm or less. In this manner, a protective layer having a film thickness of 4 μm is formed to prepare a photoreceptor of Example 31.

Example 32

The same manner as that in Example 1 is applied until the charge transporting layer is formed. Thereafter, a protective layer is formed in the following manner to prepare a photoreceptor 32, and the photoreceptor 32 is evaluated in the same manner as that in Example 1. The evaluation results are shown in Tables 4 and 5.

(Formation of Protective Layer)

30 parts by mass of a charge transport material ((I)-52), 0.2 part by mass of colloidal silica (product name: PL-1, manufactured by FUSO CHEMICAL CO., LTD.), 30 parts by mass of toluene, 0.1 part by mass of 3,5-di-t-butyl-4-hydroxytoluene (BHT) are mixed, thereby preparing a coating liquid for forming a protective layer. This coating liquid is coated onto the charge transporting layer by spray coating, followed by air drying at room temperature for 30 minutes. Thereafter, the resultant is cured with electron beams by using an electron beam emitting device in a nitrogen atmosphere having an oxygen concentration of 20 ppm or less. In this manner, a protective layer having a film thickness of 4 μm is formed to prepare a photoreceptor of Example 32.

Examples 33 to 36

The same manner as that in Example 1 is applied until the charge transporting layer is formed. Thereafter, a protective layer is formed in the following manner to prepare photoreceptors 33 to 36, and the photoreceptors 33 to 36 are evaluated in the same manner as that in Example 1. The evaluation results are shown in Tables 4 and 5.

[Photoreceptors 37 to 40]

The same manner as that in Example 1 is applied until the charge transporting layer is formed. Thereafter, protective layer is formed with the composition shown in Table 7, thereby preparing photoreceptors 37 to 40.

Examples 37 to 40

The photoreceptors 37 to 40 are evaluated in the same manner as that in Example 1. The evaluation results are shown in Tables 4 and 5.

(Formation of Protective Layer)

The electron beam curing is performed using the electron beam emitting device in the same manner as that in Example 32, except that the composition of the coating liquid for forming a protective layer is changed as Table 3. In this manner, a protective layer having a film thickness of 4 μm is formed to prepare photoreceptors of Examples 33 to 36.

Comparative Example 1

A comparative photoreceptor 1 is prepared in the same manner as that in Example 1, except that 30 parts by mass of a compound (E) of Comparative Synthesis Example 1 is used instead of the charge transport material ((I)-48) used for the protective layer, and that 30 parts by mass of tetrahydrofuran is used instead of 15 parts by mass of cyclopentanol and 15 parts by mass of cyclopentyl methyl ether. However, since the compound (E) is crystallized, a uniform protective layer fails to be obtained. Moreover, the compound (E) fails to be dissolved in 15 parts by mass of cyclopentanol and 15 parts by mass of cyclopentyl methyl ether.

Comparative Examples 2 and 3

A protective layer is formed in the same manner as that in Comparative Example 1 to prepare Comparative photoreceptors 2 and 3, except that 30 parts by mass of the following compound (F) or 30 parts by mass of compound (G) is used respectively as the charge transport material used for the protective layer instead of the compound (E). In both the photoreceptors 2 and 3, a portion of the charge transporting layer is shown to be dissolved. However, the surface thereof is uniform, and severe unevenness is not observed. The obtained photoreceptors are evaluated in the same manner as that in Example 1. In addition, both the compounds (F) and (G) show insufficient solubility with respect to 15 parts by mass of cyclopentanol and 15 parts by mass of cyclopentyl methyl ether, and result in separation during drying and curing. Consequently, tetrahydrofuran is used as a solvent.

The evaluation results are shown in Tables 4 and 5.

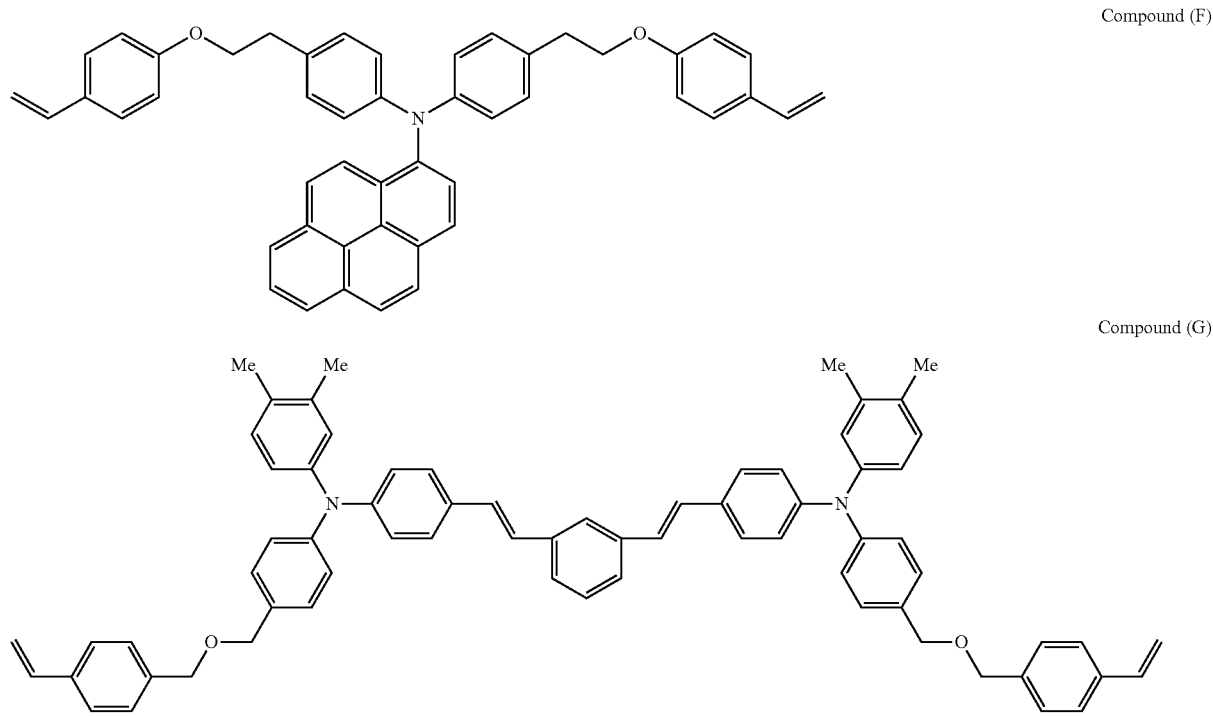

Compound (F)

Compound (G)

Comparative Examples 4 to 6

Comparative photoreceptors 4 to 6 of Comparative Examples 7 to 9 are obtained in the same manner as that in Example 29, except that the compounds (E), (F), and (G) are used instead of the charge transport material ((I)-52), and that the solvent is changed to tetrahydrofuran. The obtained comparative photoreceptors 4 to 6 are evaluated in the same manner as that in Example 1. The evaluation results are shown in Tables 4 and 5.

Comparative Example 7

The photoreceptor of Example 1 in which the undercoat layer, charge generating layer, and charge transporting layer are formed is obtained as a comparative photoreceptor 7 of Comparative Example 7. The obtained comparative photoreceptor 7 is evaluated in the same manner as that in Example 1. The evaluation results are shown in Tables 4 and 5.

Comparative Examples 8 to 9

A protective layer is formed in the same manner as that in Comparative Example 1 to prepare comparative photoreceptors 8 and 9, except that 30 parts by mass of the following compound (H) or 30 parts by mass of compound (I) is used respectively as the charge transport material ((I)-48) used for the protective layer. In both the comparative photoreceptors 8 and 9, a portion of the charge transporting layer is shown to be dissolved. However, the surface thereof is uniform, and severe unevenness is not observed. The obtained photoreceptors are evaluated in the same manner as that in Example 1. In addition, since both the compounds (F) and (G) show insufficient solubility with respect to 15 parts by mass of cyclopentanol and 15 parts by mass of cyclopentyl methyl ether, 15 parts by mass of cyclopentanol and 15 parts by mass of tetrahydrofuran are used as a mixed solvent.

The evaluation results are shown in Tables 4 to 5.

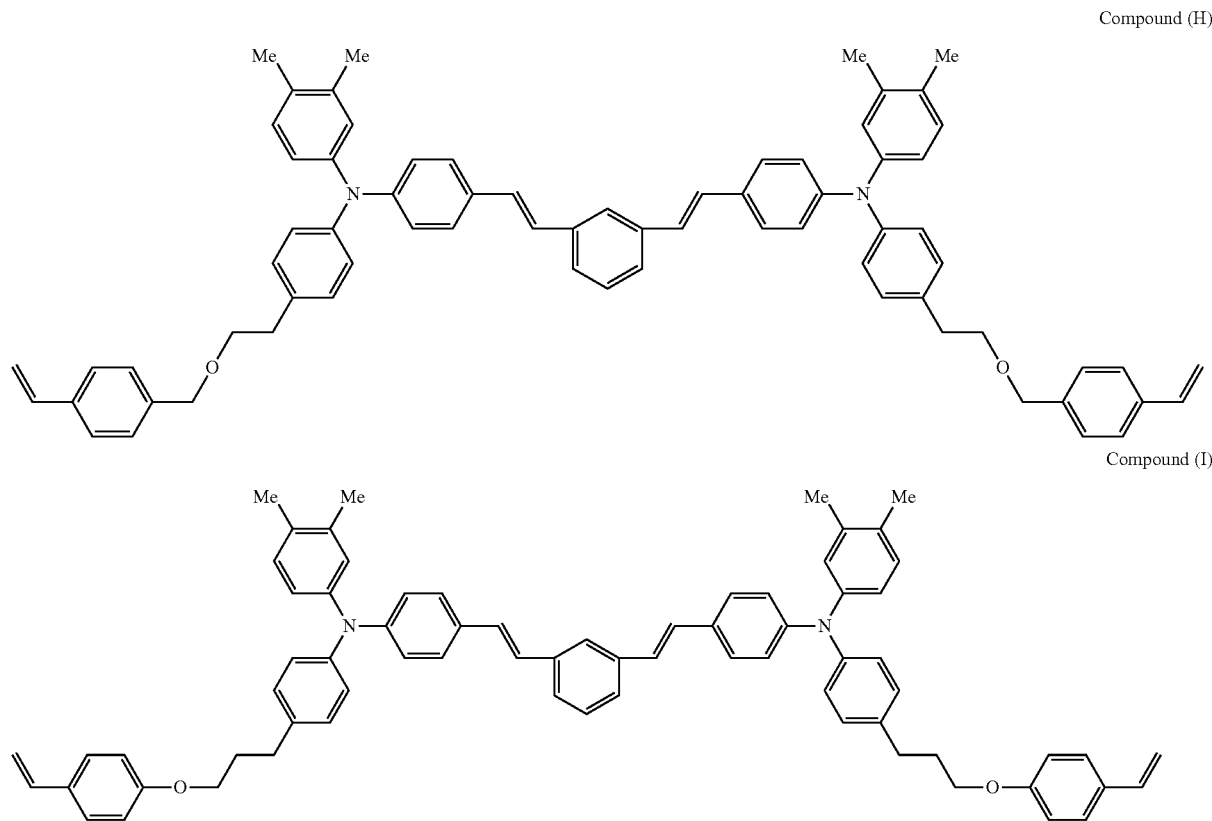

Compound (H)

Compound (I)

TABLE 4

| | | | | Low temperature and low humidity (8° C., 20% RH) | | | | | | | | | |
|---|---|---|---|---|---|---|---|---|---|---|---|---|---|
| | | | | After 3000-sheet test at low temperature and low humidity | | | | | After being left for 24 hours at low temperature and low humidity | | | | |
| Example | Photoreceptor | Adhesiveness | Abrasion loss (μm) | Image quality uniformity | Ghost | Fogging | Streaks | Image deletion | Image quality uniformity | Ghost | Fogging | Streaks | Image deletion |
| Example-1 | Photoreceptor-1 | A | 0.10 | A | A | B | B | A | A | A | B | B | A |
| Example-2 | Photoreceptor-2 | A | 0.11 | A | A | B | B | A | A | A | B | B | A |
| Example-3 | Photoreceptor-3 | A | 0.11 | A | A | B | B | A | A | A | B | B | A |
| Example-4 | Photoreceptor-4 | A | 0.12 | A | A | B | A | A | A | A | B | A | A |
| Example-5 | Photoreceptor-5 | A | 0.11 | A | A | B | B | A | A | A | B | B | A |
| Example-6 | Photoreceptor-6 | A | 0.25 | A | A | A | A | A | A | A | A | A | A |
| Example-7 | Photoreceptor-7 | A | 0.23 | A | A | A | B | A | A | A | A | B | A |
| Example-8 | Photoreceptor-8 | A | 0.25 | A | A | A | A | A | A | A | A | A | A |
| Example-9 | Photoreceptor-9 | A | 0.27 | A | A | A | B | A | A | A | A | B | A |
| Example-10 | Photoreceptor-10 | A | 0.24 | A | A | A | A | A | A | A | A | A | A |
| Example-11 | Photoreceptor-11 | A | 0.19 | A | A | B | B | A | A | A | B | B | A |
| Example-12 | Photoreceptor-12 | A | 0.17 | A | A | B | A | A | A | A | B | A | A |
| Example-13 | Photoreceptor-13 | A | 0.20 | A | A | B | B | A | A | A | B | B | A |
| Example-14 | Photoreceptor-14 | A | 0.11 | A | B | B | A | A | A | B | B | A | A |
| Example-15 | Photoreceptor-15 | A | 0.22 | A | A | B | A | A | A | A | B | A | A |
| Example-16 | Photoreceptor-16 | A | 0.23 | A | A | B | A | A | A | A | B | A | A |
| Example-17 | Photoreceptor-17 | A | 0.10 | A | A | B | A | A | A | A | B | A | A |
| Example-18 | Photoreceptor-18 | A | 0.09 | A | A | B | A | A | A | A | B | A | A |
| Example-19 | Photoreceptor-19 | A | 0.08 | A | A | B | A | A | A | A | B | A | A |
| Example-20 | Photoreceptor-20 | A | 0.10 | A | A | B | A | A | A | A | B | A | A |

TABLE 4-continued

|  |  |  |  | Low temperature and low humidity (8° C., 20% RH) | | | | | | | | | |
| --- | --- | --- | --- | --- | --- | --- | --- | --- | --- | --- | --- | --- | --- |
|  |  |  |  | After 3000-sheet test at low temperature and low humidity | | | | | After being left for 24 hours at low temperature and low humidity | | | | |
| Example | Photoreceptor | Ad-hesive-ness | Abrasion loss (μm) | Image quality uniformity | Ghost | Fogging | Streaks | Image deletion | Image quality uniformity | Ghost | Fogging | Streaks | Image deletion |
| Example-21 | Photoreceptor-21 | A | 0.06 | A | B | B | A | A | A | B | B | A | A |
| Example-22 | Photoreceptor-22 | A | 0.26 | A | A | A | B | A | A | A | A | B | A |
| Example-23 | Photoreceptor-23 | A | 0.25 | A | A | A | A | A | A | A | A | A | A |
| Example-24 | Photoreceptor-24 | A | 0.26 | A | A | A | B | A | A | A | A | B | A |
| Example-25 | Photoreceptor-25 | A | 0.29 | A | A | A | A | A | A | A | A | A | A |
| Example-26 | Photoreceptor-26 | A | 0.11 | A | A | A | A | A | A | A | A | A | A |
| Example-27 | Photoreceptor-27 | A | 0.12 | A | A | A | A | A | A | A | A | A | A |
| Example-28 | Photoreceptor-28 | A | 0.11 | A | A | A | A | A | A | A | A | A | A |
| Example-29 | Photoreceptor-29 | — | 0.19 | A | A | A | A | A | A | A | A | A | A |
| Example-30 | Photoreceptor-30 | — | 0.18 | A | A | A | A | A | A | A | A | A | A |
| Example-31 | Photoreceptor-31 | A | 0.15 | A | A | A | A | A | A | A | A | A | A |
| Example-32 | Photoreceptor-32 | A | 0.16 | A | A | A | A | A | A | A | A | A | A |
| Example-33 | Photoreceptor-33 | A | 0.16 | A | A | A | A | A | A | A | A | A | A |
| Example-34 | Photoreceptor-34 | A | 0.09 | A | A | A | A | A | A | A | A | A | A |
| Example-35 | Photoreceptor-35 | A | 0.10 | A | A | A | A | A | A | A | A | A | A |
| Example-36 | Photoreceptor-36 | A | 0.11 | A | A | A | B | A | A | A | A | B | A |
| Example-37 | Photoreceptor-37 | A | 0.20 | A | B | B | A | A | A | B | B | A | A |
| Example-38 | Photoreceptor-38 | A | 0.18 | A | B | B | A | A | A | B | B | A | A |
| Example-39 | Photoreceptor-39 | A | 0.22 | A | A | B | A | A | A | A | B | A | A |
| Example-40 | Photoreceptor-40 | A | 0.25 | A | A | A | A | A | A | A | A | A | A |
| Comparative Example-1 | Not obtained | — | — | — | — | — | — | — | — | — | — | — | — |
| Comparative Example-2 | Comparative photoreceptor-2 | A | 0.49 | A | B | A | B | A | A | B | A | B | A |
| Comparative Example-3 | Comparative photoreceptor-3 | A | 0.55 | A | B | A | B | A | A | B | A | B | A |
| Comparative Example-4 | Comparative photoreceptor-4 | — | 0.68 | C | C | A | B | A | C | C | A | B | A |
| Comparative Example-5 | Comparative photoreceptor-5 | — | 0.44 | A | B | A | B | A | A | B | A | B | A |
| Comparative Example-6 | Comparative photoreceptor-6 | — | 0.60 | A | B | A | B | A | A | B | A | B | A |
| Comparative Example-7 | Comparative photoreceptor-7 | — | 0.83 | A | A | A | B | A | A | A | A | B | A |
| Comparative Example-8 | Comparative photoreceptor-8 | A | 0.63 | A | B | A | B | A | A | B | A | B | A |
| Comparative Example-9 | Comparative photoreceptor-9 | A | 0.74 | A | B | A | B | A | A | B | A | C | A |

TABLE 5

|  | High temperature and high humidity (28° C., 85% RH) | | | | | | | | | |
| --- | --- | --- | --- | --- | --- | --- | --- | --- | --- | --- |
|  | After 3000-sheet test at high temperature and high humidity | | | | | After being left for a day at high temperature and high humidity | | | | |
| Example | Image quality uniformity | Ghost | Fogging | Photoreceptor surface attachment | Image deletion | Image quality uniformity | Ghost | Fogging | Photoreceptor surface attachment | Image deletion |
| Example-1 | A | B | B | B | B | A | A | B | B | B |
| Example-2 | A | B | B | B | B | A | A | B | B | B |
| Example-3 | A | B | B | B | B | A | A | B | B | B |
| Example-4 | A | B | B | A | A | A | A | B | A | A |
| Example-5 | A | B | B | B | B | A | A | B | B | B |
| Example-6 | A | B | B | A | A | A | A | B | A | A |
| Example-7 | A | B | B | B | B | A | A | B | B | B |
| Example-8 | A | B | B | A | A | A | A | B | A | A |
| Example-9 | A | B | B | B | B | A | A | B | B | B |
| Example-10 | A | B | B | A | A | A | A | B | A | A |
| Example-11 | A | B | B | B | B | A | A | B | B | B |
| Example-12 | A | B | B | A | A | A | A | B | A | A |
| Example-13 | A | B | B | B | B | A | A | B | B | B |
| Example-14 | A | B | B | A | A | A | A | B | A | A |
| Example-15 | A | B | B | A | A | A | A | B | A | A |
| Example-16 | A | B | B | A | A | A | A | B | A | A |
| Example-17 | A | B | B | A | A | A | A | B | A | A |
| Example-18 | A | B | B | A | A | A | A | B | A | A |

TABLE 5-continued

| | High temperature and high humidity (28° C., 85% RH) | | | | | | | | | |
|---|---|---|---|---|---|---|---|---|---|---|
| | After 3000-sheet test at high temperature and high humidity | | | | | After being left for a day at high temperature and high humidity | | | | |
| Example | Image quality uniformity | Ghost | Fogging | Photoreceptor surface attachment | Image deletion | Image quality uniformity | Ghost | Fogging | Photoreceptor surface attachment | Image deletion |
| Example-19 | A | B | B | A | A | A | A | B | A | A |
| Example-20 | A | B | B | A | A | A | A | B | A | A |
| Example-21 | A | B | B | A | A | A | A | B | A | A |
| Example-22 | A | A | A | B | B | A | A | A | B | B |
| Example-23 | A | A | A | A | A | A | A | A | A | A |
| Example-24 | A | A | A | B | B | A | A | A | B | B |
| Example-25 | A | A | A | A | A | A | A | A | A | A |
| Example-26 | A | A | A | A | A | A | A | A | A | A |
| Example-27 | A | A | A | A | A | A | A | A | A | A |
| Example-28 | A | A | A | A | A | A | A | A | A | A |
| Example-29 | A | A | A | A | A | A | A | A | A | A |
| Example-30 | A | A | A | A | A | A | A | A | A | A |
| Example-31 | A | A | A | A | A | A | A | A | A | A |
| Example-32 | A | A | A | A | A | A | A | A | A | A |
| Example-33 | A | A | A | A | A | A | A | A | A | A |
| Example-34 | A | A | A | A | A | A | A | A | A | A |
| Example-35 | A | A | A | A | A | A | A | A | A | A |
| Example-36 | A | A | A | B | B | A | A | A | B | B |
| Example-37 | A | B | B | A | A | A | A | B | A | A |
| Example-38 | A | B | B | A | A | A | A | B | A | A |
| Example-39 | A | B | B | A | A | A | A | B | A | A |
| Example-40 | A | B | B | A | A | A | A | B | A | A |
| Comparative Example-1 | — | — | — | — | — | — | — | — | — | — |
| Comparative Example-2 | B | A | C | A | B | B | A | C | A | C |
| Comparative Example-3 | B | A | C | A | B | B | A | C | A | C |
| Comparative Example-4 | B | A | C | A | C | C | A | C | A | C |
| Comparative Example-5 | B | A | C | B | A | B | A | C | B | A |
| Comparative Example-6 | B | A | C | B | A | B | A | C | B | A |
| Comparative Example-7 | C | A | A | A | A | C | A | A | A | A |
| Comparative Example-8 | B | A | C | A | B | B | A | C | A | C |
| Comparative Example-9 | B | A | C | A | B | B | A | C | A | C |

As shown in Tables 4 and 5, in examples, the abrasion resistance is higher than that in comparative examples, and any of the image quality uniformity, fogging, streaks, and image deletion is excellent.

In addition, when the electrophotographic photoreceptors of comparative examples are used, the evaluation results of the image forming tests performed at a high temperature and high humidity are worse than the evaluation results of the image forming tests performed at a low temperature and low humidity. Presumably, this is because the surface of the photoreceptor adsorbs moisture in the air, and the electrostatic latent image is deleted in the lateral direction and messed up. It is also presumed that this is because how an electrophotographic photoreceptor is affected by such a phenomenon varies depending on the constitutional materials of the photoreceptor.

Examples 1A to 10A, Comparative Examples 1A to 5A

According to Table 3, the photoreceptors and comparative photoreceptors prepared in the above examples and comparative examples are mounted on an image forming apparatus (test model in Fuji Xerox Co., Ltd.) that has the same configuration as that in FIG. 10 and uses a liquid developer, and the following evaluations are performed. The results are shown in Table 6.

<Image Forming Apparatus>

An image forming apparatus having the configuration shown in FIGS. 10 and 11 is used.

<Liquid Developer>

20 parts by mass of lecithin containing 90% by mass of phosphatidylserine is mixed with 80 parts of Isopar M, thereby obtaining a charge-controlling agent. 1 part by mass of carbon black, 20 parts by mass of an ethylene-vinyl acetate copolymer, and 75 parts by mass of Isopar M are dispersed for 10 hours by using a sand mill, and the resultant is diluted with Isopar M so as to yield 3 parts by mass of solid contents ratio, thereby obtaining a liquid toner. 100 parts by mass of the liquid toner is mixed with 1 part by mass of the charge-controlling agent, thereby obtaining a liquid developer.

By using a phthalocyanine pigment (cyan toner), a yellow azo pigment (yellow toner), and a quinacridone pigment (magenta toner) instead of carbon black, liquid cyan, yellow, and magenta developers are obtained.

Comparative Example 6A

The photoreceptor of Example 1 in which the undercoat layer, charge generating layer, and charge transporting layer are formed is used as a comparative photoreceptor 7, and this photoreceptor is mounted on an image forming apparatus (test model in Fuji Xerox Co., Ltd.) that has the same configuration as that in FIG. 10 and uses a liquid developer, and the following evaluations are performed. The results are shown in Table 6.

<Evaluation of Cracking on the Photoreceptor Surface>

This evaluation is performed in the following manner. The existence of cracks on the photoreceptor having performed 10000 times of printing is visually observed. The evaluation criteria are as follows.

A: No cracks on the photoreceptor surface
B: Fine cracks are shown on the photoreceptor surface, but there is no defect in image quality.
C: Cracks on the photoreceptor surface appear as an image.
D: The photoreceptor surface is markedly deteriorated, and tests fail to be consecutively performed during the printing test.

<Evaluation of Cleaning Damage on Photoreceptor Surface>

This evaluation is performed by visually observing the photoreceptor surface after the printing test. The evaluation criteria are as follows.

A: No damage on the photoreceptor surface
B: Minor damage is shown on the photoreceptor surface, but there is no defect in image quality.
C: Damage on the photoreceptor surface is observed, and the damage appears as an image.
D: The photoreceptor surface is markedly deteriorated, and tests fail to be consecutively performed during the printing test.

<Evaluation of Electrical Characteristics of Photoreceptor>

This evaluation is performed in the following manner. By using the same chart as that in Example 1, sheets of A4 paper (P paper, manufactured by Fuji Xerox Co., Ltd.) are fed in the transverse direction, and printing is performed 10000 times. The change in print density of black images having 40% density is evaluated as an index of electrical characteristics by using SpectroEyeLT manufactured by Sakata Inx Engineering Co., Ltd. The evaluation criteria are as follows.

A: |Difference in image density before and after printing|<1
B: 1≤|Difference in image density before and after printing|<1.5
C: 1.5≤|Difference in image density before and after printing|<2
D: 2≤|Difference in image density before and after printing|

TABLE 6

| | Applied photoreceptor | Cracking on photoreceptor surface | Cleaning damage on photoreceptor surface | Electrical characteristics of photoreceptor |
|---|---|---|---|---|
| Example 1A | Photoreceptor 2 | A | A | A |
| Example 2A | Photoreceptor 3 | A | A | A |
| Example 3A | Photoreceptor 13 | A | A | A |
| Example 4A | Photoreceptor 15 | A | A | A |
| Example 5A | Photoreceptor 16 | A | A | A |
| Example 6A | Photoreceptor 26 | A | A | A |
| Example 7A | Photoreceptor 27 | A | A | A |
| Example 8A | Photoreceptor 29 | A | A | A |
| Example 9A | Photoreceptor 31 | A | A | A |
| Example 10A | Photoreceptor 34 | A | A | A |
| Comparative Example 1A | Comparative photoreceptor 2 | A | B | B |
| Comparative Example 2A | Comparative photoreceptor 3 | A | B | B |
| Comparative Example 3A | Comparative photoreceptor 4 | B | D | D |
| Comparative Example 4A | Comparative photoreceptor 5 | B | C | C |
| Comparative Example 5A | Comparative photoreceptor 6 | B | C | C |
| Comparative Example 6A | Comparative photoreceptor 7 | D | D | D |

From the above results, it is understood that in the present examples, the results for any of the cracking on the photoreceptor surface, cleaning damage, and electrical characteristics are more excellent compared to comparative examples, even in the image forming apparatus using the liquid developer.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A compound represented by the following Formula (II):

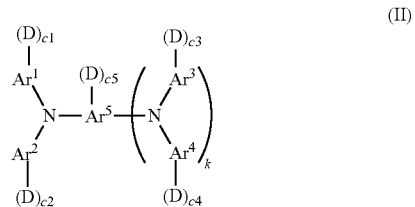

wherein in Formula (II),
each of $Ar^1$ to $Ar^4$ independently represents a substituted or unsubstituted aryl group,
$Ar^5$ represents a substituted or unsubstituted aryl group or a substituted or unsubstituted arylene group,
each of c1 to c5 represents an integer of from 0 to 2 and a sum of c1 to c5 is an integer of from 1 to 8,
k represents 1, and
D is a group represented by the following Formula (III):

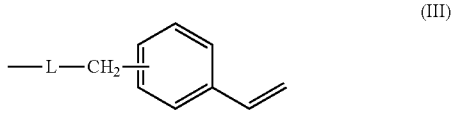

(III)

wherein in Formula (III),
L represents a divalent linking group that includes a $-(CH_2)_n-O-$ group directly linked to the aryl group of $Ar^1$ to $Ar^4$ and the aryl group or arylene group of $Ar^5$, and
n represents an integer of from 3 to 6.

2. The compound according to claim 1, wherein the sum of c1 to c5 in Formula (II) is an integer of from 3 to 8.

3. A charge transporting film comprising the compound according to claim 1 or a structure derived therefrom.

4. A charge transporting film, comprising:
a cured material that is obtained by curing a composition containing the compound according to claim 1.

5. A photoelectric conversion device comprising the charge transporting film according to claim 3.

6. An electrophotographic photoreceptor comprising:
a conductive substrate; and
a photosensitive layer provided on the conductive substrate,
wherein an uppermost surface layer of the electrophotographic photoreceptor contains the compound according to claim 1 or a structure derived therefrom.

7. The electrophotographic photoreceptor according to claim 6, wherein the uppermost surface layer is a cured film of a composition containing the compound represented by the Formula (II).

8. The electrophotographic photoreceptor according to claim 7, wherein the composition contains a second compound reacting with the compound represented by the Formula (II).

9. The electrophotographic photoreceptor according to claim 7, wherein the composition contains a polymer not reacting with the compound represented by the Formula (II).

10. The electrophotographic photoreceptor according to claim 8, wherein the second compound reacting with the compound represented by the Formula (II) is a monomer or oligomer that does not have a charge transport property.

11. The electrophotographic photoreceptor according to claim 8, wherein the second compound reacting with the compound represented by the Formula (II) is a charge transporting compound that has a charge transport property.

12. The electrophotographic photoreceptor according to claim 7, wherein the cured film is obtained by curing the composition with heat, light or electron beams.

13. The electrophotographic photoreceptor according to claim 6, wherein the uppermost surface layer contains particles.

14. The electrophotographic photoreceptor according to claim 6, wherein the uppermost surface layer is a protective layer.

15. The electrophotographic photoreceptor according to claim 6, further comprising an adjacent layer that is adjacent to the uppermost surface layer between the conductive substrate and the uppermost surface layer,
wherein the adjacent layer contains a resin having a viscosity average molecular weight of 50000 or more.

16. A method of producing an electrophotographic photoreceptor, comprising:
forming a coating film by coating a coating liquid containing a composition that contains the compound according to claim 1 on a surface to be coated; and then
curing the coating film by heating in a condition of from 100° C. to 170° C.

17. A process cartridge that is detachable from an image forming apparatus, comprising the electrophotographic photoreceptor according to claim 6.

18. The process cartridge according to claim 17, further comprising a developing unit that develops an electrostatic latent image formed on the electrophotographic photoreceptor by using a liquid developer containing a toner.

19. An image forming apparatus comprising:
the electrophotographic photoreceptor according to claim 6;
a charging unit that charges the electrophotographic photoreceptor;
an electrostatic latent image forming unit that forms an electrostatic latent image on a charged electrophotographic photoreceptor;
a developing unit that develops the electrostatic latent image formed on the electrophotographic photoreceptor by using a developer containing a toner to form a toner image; and
a transfer unit that transfers the toner image to a transfer medium.

20. The image forming apparatus according to claim 19, wherein the developer is a liquid developer.

21. An image forming apparatus comprising:
the electrophotographic photoreceptor according to claim 6;
a charging unit that charges the electrophotographic photoreceptor;
an electrostatic latent image forming unit that forms an electrostatic latent image on a charged electrophotographic photoreceptor;
a developing unit that develops the electrostatic latent image formed on the electrophotographic photoreceptor by using the developer to be a layer to form an image developed by a liquid developer;
an intermediate transfer member to which the image developed by the liquid developer that is formed on the electrophotographic photoreceptor is transferred;
a primary transfer unit that transfers the image developed by the liquid developer that is formed on the electrophotographic photoreceptor to the intermediate transfer member;
a film forming unit that forms the image developed by the liquid developer that is formed on the electrophotographic photoreceptor into a film; and
a secondary transfer unit that transfers the image developed by the liquid developer having become a film to a transfer medium from the intermediate transfer member.

* * * * *